(12) United States Patent
Wollowick et al.

(10) Patent No.: US 10,758,198 B2
(45) Date of Patent: *Sep. 1, 2020

(54) SYSTEMS AND METHODS FOR INTRA-OPERATIVE IMAGE ANALYSIS

(71) Applicant: DePuy Synthes Products, Inc., Raynham, MA (US)

(72) Inventors: Noah D. Wollowick, Stamford, CT (US); Andrew J. Cooper, Largo, FL (US); Xiu Jiang, Rego Park, NY (US); Cameron Albert, Powhatan, VA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 830 days.

This patent is subject to a terminal disclaimer.

(21) Appl. No.: 14/630,300

(22) Filed: Feb. 24, 2015

(65) Prior Publication Data

US 2015/0238271 A1  Aug. 27, 2015

Related U.S. Application Data

(60) Provisional application No. 62/105,183, filed on Jan. 19, 2015, provisional application No. 62/080,953, (Continued)

(51) Int. Cl.
*A61B 6/00* (2006.01)
*A61B 6/12* (2006.01)

(52) U.S. Cl.
CPC ............... *A61B 6/505* (2013.01); *A61B 6/12* (2013.01); *G06T 2207/10116* (2013.01); *G06T 2207/30008* (2013.01); *G06T 2207/30052* (2013.01)

(58) Field of Classification Search
None
See application file for complete search history.

(56) References Cited

U.S. PATENT DOCUMENTS

| 5,715,836 A | 2/1998 | Kliegis et al. |
| 6,205,411 B1 | 3/2001 | DiGioia, III et al. |

(Continued)

FOREIGN PATENT DOCUMENTS

| EP | 15755633 | 9/2017 |
| JP | 2005130928 A | 5/2005 |

(Continued)

OTHER PUBLICATIONS

Baumgaertner et al., the Value of the Tip-Apex Distance in Predicting Failure of Fixation of Peritrochanteric Fractures of the Hip, J. Bone and Joint Surg., 1995, pp. 1058-1064, vol. 77-A.

(Continued)

*Primary Examiner* — Pascal M Bui Pho
*Assistant Examiner* — Farouk A Bruce
(74) *Attorney, Agent, or Firm* — Venkatesh Krishnamoorthy; Silicon Valley Patent Group, LLP

(57) ABSTRACT

A system and method for analyzing images to optimize orthopaedic functionality at a site within a patient, including obtaining at least a first, reference image of the site, or a corresponding contralateral site, the first image including at least a first anatomical region or a corresponding anatomical region. At least a second, intra-operative results image of the site is obtained. At least one stationary base with at least two base points is selected to serve as a reference for both images during analysis including at least one of scaling, calculations, and image comparisons.

9 Claims, 76 Drawing Sheets

Related U.S. Application Data filed on Nov. 17, 2014, provisional application No. 62/051,238, filed on Sep. 16, 2014, provisional application No. 62/016,483, filed on Jun. 24, 2014, provisional application No. 61/980,659, filed on Apr. 17, 2014, provisional application No. 61/948,534, filed on Mar. 5, 2014, provisional application No. 61/944,520, filed on Feb. 25, 2014.

(56) References Cited

U.S. PATENT DOCUMENTS

| | | |
|---|---|---|
| 6,614,453 B1 | 9/2003 | Suri et al. |
| 8,249,318 B2 | 8/2012 | Schmitt et al. |
| 8,311,791 B1 | 11/2012 | Avisar |
| 8,484,001 B2 | 7/2013 | Glozman et al. |
| 8,635,082 B2 | 1/2014 | Woods et al. |
| 8,831,324 B2 | 9/2014 | Penenberg |
| 8,917,290 B2 | 12/2014 | Beck |
| 2004/0171924 A1* | 9/2004 | Mire ............... A61B 34/20 600/407 |
| 2005/0015005 A1 | 6/2005 | Kockro |
| 2006/0293614 A1 | 12/2006 | Radinsky |
| 2007/0015999 A1 | 1/2007 | Heldreth et al. |
| 2007/0066917 A1 | 3/2007 | Hodorek et al. |
| 2007/0078678 A1 | 4/2007 | DiSilvestro et al. |
| 2008/0021299 A1 | 1/2008 | Meulink |
| 2008/0075348 A1 | 3/2008 | Rappaport et al. |
| 2008/0120262 A1 | 5/2008 | Habets et al. |
| 2008/0161680 A1 | 7/2008 | von Jako et al. |
| 2009/0089034 A1 | 4/2009 | Penney et al. |
| 2010/0249507 A1 | 9/2010 | Prisco et al. |
| 2010/0250571 A1 | 9/2010 | Pierce et al. |
| 2010/0256479 A1* | 10/2010 | Park ............... A61B 5/055 600/410 |
| 2011/0082367 A1 | 4/2011 | Regazzoni |
| 2011/0268325 A1 | 11/2011 | Teichman et al. |
| 2011/0313424 A1* | 12/2011 | Bono ............... A61B 17/1746 606/91 |
| 2011/0319941 A1* | 12/2011 | Bar ............... A61B 17/1671 606/279 |
| 2012/0016269 A1* | 1/2012 | Moctezuma de la Barrera .......... G06F 19/321 600/595 |
| 2012/0157887 A1 | 6/2012 | Fanson |
| 2012/0194505 A1 | 8/2012 | Beck |
| 2012/0194666 A1 | 8/2012 | Jackson |
| 2013/0060146 A1 | 3/2013 | Yang et al. |
| 2013/0072821 A1 | 3/2013 | Odermatt |
| 2013/0135721 A1 | 5/2013 | An et al. |
| 2013/0197687 A1 | 8/2013 | Pavlovskaia et al. |
| 2014/0003700 A1* | 1/2014 | Hermosillo Valadez .......... G06T 11/003 382/131 |
| 2014/0062863 A1 | 3/2014 | Yu et al. |
| 2014/0073907 A1 | 3/2014 | Kumar et al. |
| 2014/0303938 A1* | 10/2014 | Schoenefeld ......... A61B 19/50 703/1 |
| 2014/0378828 A1 | 12/2014 | Penenberg et al. |
| 2015/0150523 A1 | 6/2015 | Sirpad et al. |
| 2015/0238271 A1 | 8/2015 | Wollowick |
| 2016/0225192 A1 | 8/2016 | Jones et al. |

FOREIGN PATENT DOCUMENTS

| | | |
|---|---|---|
| JP | 2012020133 A | 2/2012 |
| WO | WO-2007-009263 A1 | 1/2007 |
| WO | WO-2013-175471 A1 | 11/2013 |
| WO | 2014008613 A1 | 1/2014 |
| WO | WO2014-127354 A1 | 8/2014 |
| WO | PCT-US2015-017603 | 9/2015 |
| WO | WO-2015-130848 A1 | 9/2015 |

OTHER PUBLICATIONS

Mann et al., Radiographic Evaluation of the Wrist: What Does the Hand Surgeon Want to Know?, Radiology, 1992, pp. 15-24, vol. 184.

Matta et al., Single-incision Anterior Approach for Total Hip Arthroplasty on an Orthopaedic Table, Clin. Ortho. and Related Research, 2005, pp. 115-124, vol. 441, Lippincott Williams & Wilkins.

Liaw et al., A New Tool for Measuring Cup Orientation in Total Hip Arthroplasties from Plain Radiographs, Clin. Ortho. and Related Research, 2006, pp. 134-139, vol. 451, Lippincott Wiliams & Wilkins.

De Bruijn et al., Reliability of Predictors for Screw Cutout in Intertrochanteric Hip Fractures, J. Bone Joint Surg. Am., 2012, pp. 1266-1272, vol. 94, http://dx.doi.org/10.2106/JBJS.K.00357.

Branislav, Jaramaz et al., CupAlign: Computer-Assisted Postoperative Radiographic Measurement of Acetabular Components Following Total Hip Arthroplasty, Jan. 1, 2006, pp. 876-882, Medical Image Computing and Computer Assisted Intervention 1999, 2nd Int'l Conf., Cambridge, UK, Sep. 19-22, 1999, [Lecture Notes in Computer Science 1679], Springer, Berlin, DE (XP019036244, ISBN: 978-3-540-66503-8).

Japanese office action and translation for Application No. 2016-570943 Examiner's Notice Date of Dec. 27, 2018, dated Jan. 1, 2019, pp. 1-13.

2005130928 abstract translation.

2012020133 abstract translation.

Extended European Search Report for EP Application No. EP16876926, dated Oct. 23, 2019, pp. 1-8, issued by European Patent Office 80298 Munich, Germany.

International Preliminary Report on Patentability for PCT/US2016/067587 dated Jun. 19, 2018.

International Search Report or PCT/US2016/067587 dated May 25, 2017.

Supplementary European Search Report for EP 17739110 dated Jun. 25, 2019.

* cited by examiner

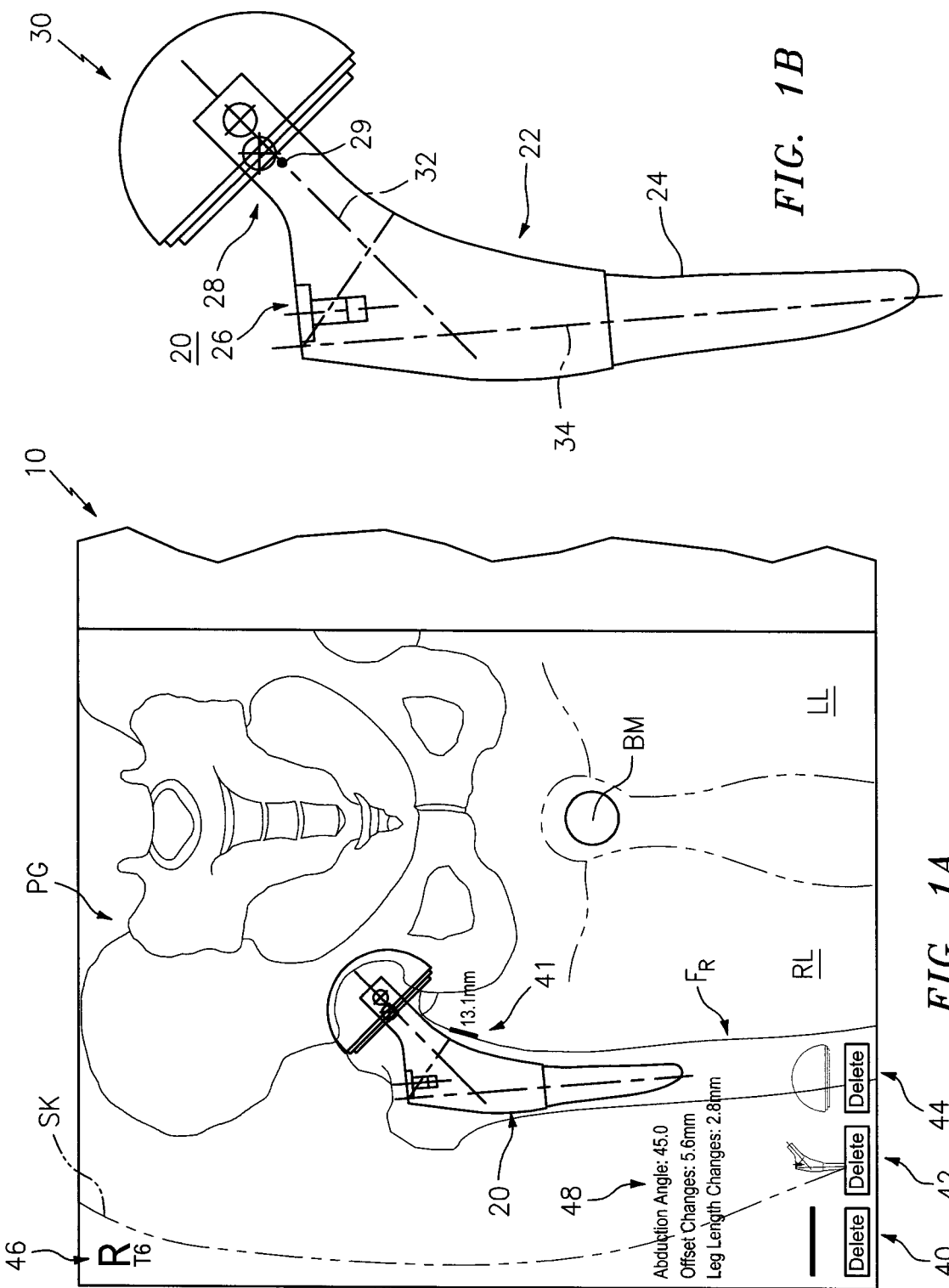

SYSTEMS AND METHODS FOR INTRA-OPERATIVE IMAGE ANALYSIS

CROSS-REFERENCE TO RELATED APPLICATION

This application claims priority to U.S. Provisional Application No. 61/944,520 filed 25 Feb. 2014, U.S. Provisional Application No. 61/948,534 filed 5 Mar. 2014, U.S. Provisional Application No. 61/980,659 filed 17 Apr. 2014, U.S. Provisional Application No. 62/016,483 filed 24 Jun. 2014, U.S. Provisional Application No. 62/051,238 filed 16 Sep. 2014, U.S. Provisional Application No. 62/080,953 filed 17 Nov. 2014, and U.S. Provisional Application No. 62/105,183 filed 19 Jan. 2015 which are incorporated by reference herein in their entireties.

FIELD OF THE INVENTION

The invention relates to analysis of images of features within a patient and more particularly to accurately scaling and/or analyzing such images during surgery.

BACKGROUND OF THE INVENTION

Orthopaedic surgeons and other healthcare professionals commonly rely on surgical guidance techniques that can be broadly classified in two categories: pre-operative digital templating or training systems that enable pre-surgical planning, and computer-assisted navigation systems providing intra-operative guidance for placement and movement of surgical instruments within a patient. There are benefits to both of these technologies, but each has respective limitations.

Preoperative digital templating techniques enable preoperative surgical planning by utilizing digital or hard copy radiographic images or similar X-ray-type, scaled according to an object of known size. Commonly, a spherical ball marker of known size is placed between the legs or next to the hip of a patient undergoing hip surgery so that it appears in the image; the ball marker is then utilized as a reference feature for image scaling. This preoperative scaling technique has inherent limitations to accuracy because it assumes that the bones within a patient and the surface ball marker will magnify at the same ratio. Commonly, the surgeon will realize during the surgery that this scale factor is inaccurate, due to deviations in magnification ratios, rendering the preoperative template ineffective for intraoperative decision making. For emergency cases such as hip fractures, preoperative digital templating often cannot be utilized, because the X-ray images are taken in a hospital setting without utilizing a ball marker or other scaling device.

Surgeons also have the option of utilizing computer-assisted navigation systems which provide intraoperative guidance. The purported benefits of computer navigation include reduction of outliers and adverse outcomes related to intraoperative positioning of surgical hardware. For example, computer navigation is utilized in hip replacement surgery to add precision to implant positioning by providing data on functional parameters such as leg length and offset changes during surgery.

Despite obvious clinical benefit, these systems have had limited adoption due to their expense, the learning curve and training requirements for surgeons and, for some systems, the additional procedure and time associated with hardware insertion into the patient. These adoption barriers have limited the use of computer assisted navigation to an extremely small percentage of overall hip arthroplasty surgeries. The surgeons that do not use these systems are limited to traditional techniques that are generally based on visual analysis and surgeon experience. However, these techniques are inconsistent, often leading to outliers in functional parameters which may affect patient satisfaction and implant longevity.

Details of one such technique, specifically used in a minimally invasive hip arthroplasty technique referred to as the direct anterior approach, are mentioned in the description of a total hip arthroplasty surgery, by Matta et al. in "Single-incision Anterior Approach for Total hip Arthroplasty on an Orthopaedic Table", Clinical Ortho. And Related Res. 441, pp. 115-124 (2005). The intra-operative technique described by Matta et al. is time-consuming and has a high risk of inaccuracy due to differences in rotation, magnification and/or scaling of various images. The high risk of inaccurate interpretation using this technique has limited its utility in guiding surgical decision making.

What appears to be a software implementation of this technique is described by Penenberg et al. in U.S. Patent Publication No. 2014/0378828, which is a continuation-in-part application of U.S. Pat. No. 8,831,324 by Penenberg. While the use of a computer system may facilitate some aspects of this technique, the underlying challenges to the technique are consistent with the challenges to Malta's approach, and limit the system's potential utility.

There are various other examples of where intra-operative guidance systems could improve quality of patient care in orthopaedics through the reduction of outliers. One such example is in the treatment of peritrochanteric hip fractures. The selection of the proper implant and associated neck-shaft angle is often incompletely evaluated by the surgeon and implant representative utilizing conventional techniques. Furthermore, variations in placement of screws and other fixation devices and implants can significantly alter patient outcomes in treatment of these fractures. These variations and resulting outcomes are analyzed by Baumgaertner et al. in "The Value of the Tip-Apex Distance in Predicting Failure of Fixation of Peritrochanteric Fractures of the Hip", J. Bone Joint Surg. 77-A No. 7, pp. 1058-1064 (1995). Other techniques relating to femoral fractures, including measurement of tip apex distance and screw position, are discussed by Bruijin et al. in "Reliability of Predictors for Screw Cutout in Intertrochanteric Hip Fractures", J. Bone Joint Surg. Am. 94, pp. 1266-72 (2012).

Proper reduction of fractures, that is, proper alignment of bones during surgery, often leads to more consistent patient outcomes, and intraoperative analysis of such reductions is incompletely evaluated currently because of the lack of non-invasive technologies that enable intraoperative analysis. One example is in the treatment of distal radius fractures. As referenced by Mann et al, "Radiographic evaluation of the wrist: what does the hand surgeon want to know?" Radiology, 184(1), pp 15-24 (1992), accurate restoration of certain parameters, such as radial inclination, radial length and Palmar Slope or Tilt, during the treatment of distal radius fractures is important. Currently, intraoperative images are utilized by surgeons, but there is no ability to readily analyse these parameters and form comparative analysis to normal anatomy.

Given the inherent scaling limitations of preoperative surgical planning and adoption barriers of current intraoperative computer navigation systems, an opportunity exists for a system and method that provides accurate intraoperative guidance and data, but without the barriers to adoption and invasive hardware requirements of traditional computer-assisted navigation.

It is therefore desirable to have a system and method to effectively scale and adjust images intra-operatively using comparative anatomical features, to enhance patient quality of care by providing accurate intra-operative guidance and data.

SUMMARY OF THE INVENTION

An object of the present invention is to provide a system and method to accurately and effectively scale, adjust and/or perform calculations on images of anatomical features and/or implants such as prosthetic devices during surgery.

Another object of the present invention is to provide image analysis and feedback information to enable more accurate planning, better fracture reduction, and/or optimal implant selection during the surgery.

Yet another object of the present invention is to capture and preserve a digital record of patient results for data collection and quality improvements in surgical procedures.

A still further object of the present invention is to improve the outcome of bone repositioning, fracture repair, and/or fixation within a patient.

This invention results from the realization that intraoperative scaling and other analysis of a primary image and at least one secondary image can be more accurately accomplished based on an object of known dimension which, along with at least two points that are consistent in those images, can facilitate precise scaling and other analysis of the secondary image in addition to the primary image as needed. At least one of the primary image and the secondary image is a results image taken during a surgical procedure on a portion of a patient. Further, at least another of the primary and secondary images is a reference image including (i) a preoperative ipsilateral image and/or (ii) a contralateral image, taken before or during surgery, of a comparable portion of the patient.

This invention features a system to analyze images at a surgical site within a patient, including an image selection module to acquire (i) at least a first, reference image including one of a preoperative image of the surgical site and a contralateral image on an opposite side of the patient from the surgical site, and (ii) at least a second, results image of the site. The system further includes a data input module that receives the first and second images and generates at least two points to establish a first stationary base and a second stationary base on at least one anatomical feature that is present in each of the first and second images, respectively, and an analysis module that utilizes the stationary base in each image to provide at least one of (a) overlaying the first and second images and comparing at least one of bone alignment, scaling and implant alignment within the images and (b) analyzing at least one of image rotation, image alignment, scaling, offset, abduction angle, length differential and orientation of at least one of a bone and an implant within the images.

In some embodiments, the first and second images are provided by the image selection module to the data input module in a digitized format. At least one dimension of each of the first and second stationary bases is retrievably stored in at least one storage medium as a count of pixels for that dimension, and the analysis module utilizes the pixel count for that dimension. In certain embodiments, the analysis module utilizes the stationary base in a selected one of the first and second images to provide at least relative scaling of the other of the first and second images to the match the scaling of the selected one of the first and second images. In one embodiment, the analysis module utilizes at least one object of known dimension in at least one of the first and second images to provide absolute scaling, that is, objective scaling according to a measurement system, to at least that image. In an embodiment, the analysis module rotates at least one of the first and second images relative to the other of the first and second images so that both images are aligned according to their respective stationary bases.

In a number of embodiments, the data input module generates at least one landmark point for each image that is spaced from the stationary base in that image, and the analysis module utilizes the landmark points to assist alignment of the first and second images relative to each other. In other embodiments, the analysis module utilizes the landmark points to position a digital template on at least one of the first and second images. In certain embodiments, the system further includes a template input module that provides at least one digital template that is superimposed over at least one feature in at least one of the first and second images. In some embodiments, the at least one digital template is matched to at least one feature in each of the first and second images. In one embodiment, at least one digital template is matched to an implant in the second, results image and then the digital template is superimposed on the first, reference image to analyze at least one parameter such as abduction angle, offset, and/or length differential of at least one bone of the patient. Preferably, the system further includes a display to provide at least visual guidance to a user of the system.

In one embodiment, the first image is a contralateral image that is flipped and overlaid on the second image and, in another embodiment, the first image is a contralateral image, the data input module generates a common stitching line in each image, typically separate from the stationary base established in each image, and the first and second images are stitched together to form a unitary view of both sides of the patient. In some embodiments, scaling or rescaling of at least one of the images is accomplished by measuring a portion of an anatomical feature during surgery, such as a femoral head, and comparing the measured feature to an initial, preoperative image which includes that feature. In other embodiments, scaling or rescaling is accomplished by identifying at least one known dimension of an implant with an intraoperative image including that implant and then scaling according to that known dimension.

This invention further features a system and method for analyzing images to optimize the restoration of orthopaedic functionality, while minimizing failures and patient discomfort, by providing intraoperative comparison including calculations, scaling and/or rescaling for at least one operative, results image of a site within a patient taken during surgery. The operative or results image is compared with at least one reference image of (i) a preoperative ipsilateral image and/or (ii) a contralateral image, taken before or during surgery, of comparable portions of a patient. At least one stationary base is selected in each image to serve as a reference during the image comparisons and/or scaling.

In certain embodiments, the system and method include optimizing the sizing and placement of an implant at the site within the patient. The step of analyzing includes estimating an optimally-configured implant, and the method further includes selecting a final implant based on the optimally-configured implant. Certain embodiments further include generating an estimated measurement of the first anatomical feature utilizing the first image, and scaling the first image includes calculating a difference between the estimated measurement and the direct measurement. In some embodiments, an initial scaling is re-scaled based on the direct measurement.

In a number of embodiments, the step of analyzing the placement includes comparing the second image with the accurately scaled first image on a mobile computing device. In one embodiment, the step of analyzing includes comparing the first anatomical feature with a corresponding contralateral anatomical feature of the patient, such as a joint on the opposite side of the patient. In certain embodiments, the first anatomical feature is located on a portion of a bony part of the patient to be replaced, such as a femoral head, and obtaining the direct measurement includes excising the bony part from the patient, and measuring the first anatomical feature substantially along the first viewing angle. In some embodiments, a guidance system is provided to adjust the viewing area of one image on a screen to track actions made by a user to another image on the screen, such as to focus or zoom in on selected landmarks in each image. In certain embodiments, at least one of abduction angle and anteversion is calculated. In certain embodiments, error analysis and/or correction is provided for at least one image, such as providing a confidence score or other normalized numeric error analysis, and/or a visual representation of at least one error value or error factor, such as relative alignment of one or more geometric shapes or symbols in two or more images.

This invention also features a system and method for analyzing images to optimize the restoration of orthopaedic functionality at a surgical site within a patient, including at least one of capturing, acquiring, selecting and receiving to provide: (i) at least a first, reference image along at least a first viewing angle including one of a preoperative image of the surgical site and a contralateral image on an opposite side of the patient from the surgical site; and (ii) at least a second, results image of the site along the first viewing angle after a surgical procedure has been performed at the site. The system and method further include generating on each of the first and second images at least two points to establish a stationary base on a stable portion of the surgical site and identifying at least one landmark on another portion of the surgical site spaced from the stationary base, and providing at least one of (a) an overlay of the first and second images to enable comparison of at least one of bone and implant alignment within the images, (b) matching of at least one digital template to at least one feature in each of the first and second images, and (c) a numerical analysis of at least one difference between points of interest, such as at least one of offset, length differential and orientation of at least one of a bone and an implant within the images.

BRIEF DESCRIPTION OF THE DRAWINGS

In what follows, preferred embodiments of the invention are explained in more detail with reference to the drawings, in which:

FIG. 1A is a schematic image viewable on a display screen by a user of a system and method according to the present invention, depicting a template image of a prosthesis superimposed over the upper portion of a femur in an X-ray image of the hip region of a patient;

FIG. 1B is an enlargement of the digital template image of FIG. 1A;

Figure 1:
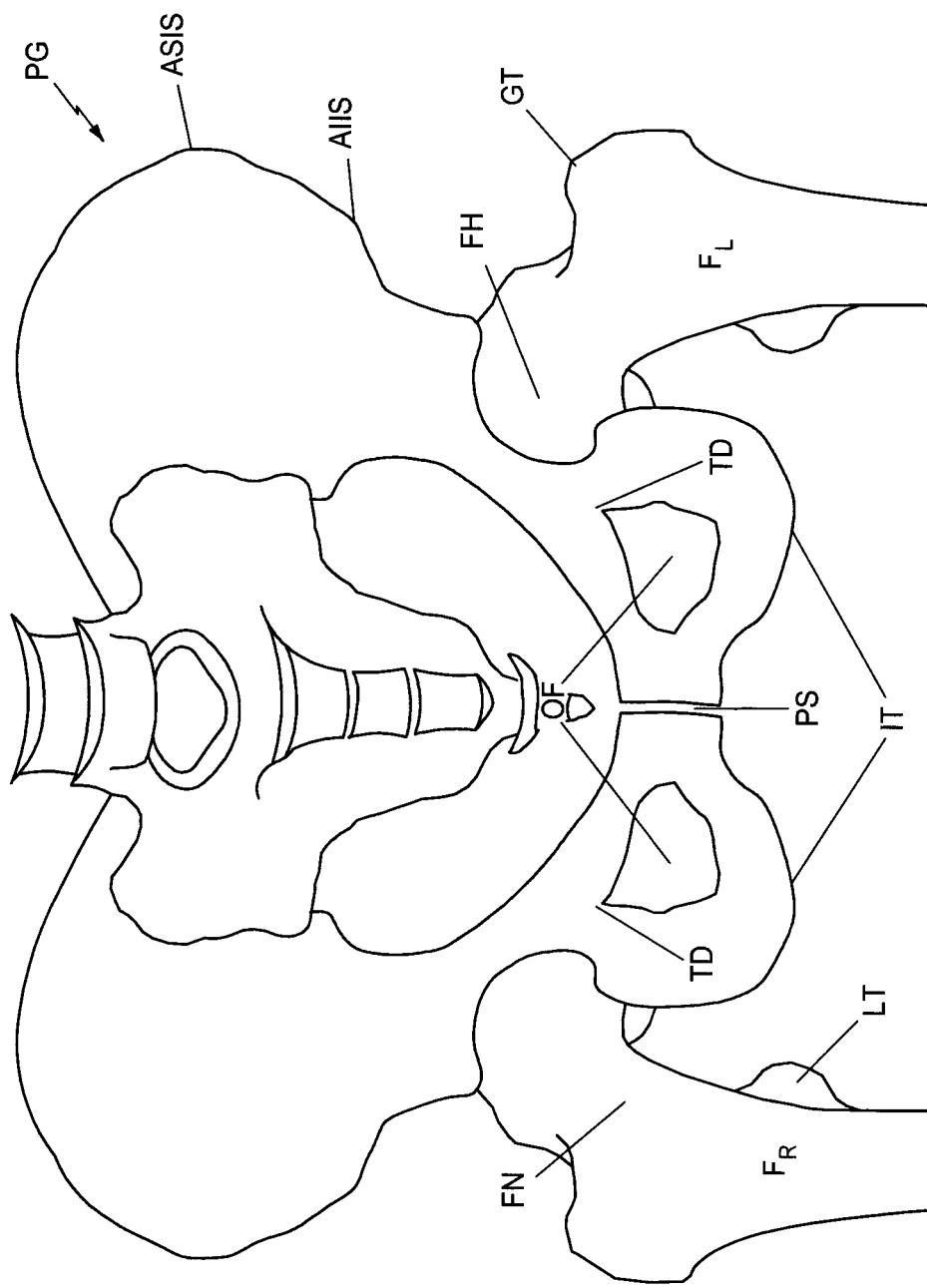
FIG. 1 is a schematic image of a frontal, X-ray-type view of a pelvic girdle of a patient illustrating various anatomical features.

DETAILED DESCRIPTION OF THE
PRESENTLY PREFERRED EMBODIMENTS

This invention may be accomplished by a system and method that provides intraoperative guidance via analysis including at least one of scaling, calculations, comparisons, and alignment for operative images taken during surgery by comparing them with preoperative ipsilateral images and/or contralateral images, taken before or during surgery, of comparable portions of a patient. At least one stationary base is selected in each image to serve as a reference during the image analysis. Broadly, some techniques according to the present invention, referred to by the present inventors as "Image Overlay", place one image over another image during analysis to generate a combined overlapped image, while certain other techniques according to the present invention, referred to by the present inventors as "Reverse Templating" or "Templating Technique", place a digital template first on a properly-scaled intra-operative image and then on a scaled pre-operative image during analysis.

In general, accurate analysis of two images of a patient is directly related not only to how similar the two images are, but also how similarly the images are aligned with respect to scale, rotation, and translation. Using conventional techniques, a user would have to manually adjust the images and/or retake multiple images to achieve this goal, something that would be difficult to do reliably and accurately. Utilizing two or more points as a stationary base according to the present invention in each image enables accurate analysis of the two images. Furthermore, the present Image Overlay technique can analyze how "similar" these images are to give the user feedback as to how accurate the results are, that is, to provide a confidence interval.

To obtain useful information, the images (the "intraop" intra-operative image and a "preop" pre-operative image, for example) must be scaled similarly and preferably rotated similarly. If the scale is off, this will lead to error unless re-scaled properly. If the rotation is off, the user is likely to spend significant time "eyeballing" to manually align the digital template on the preop image to match the intraop position during Reverse Templating according to the present invention. Use of one or more landmarks, such as the teardrop of the pelvis and/or the greater trochanter of the femur for hip-related surgery, according to the present invention aids in automated and accurate superimposing of a template onto the preop image to match the intraop position of an implant and superimposed digital template during Reverse Templating. For example, the teardrop helps accurately place the acetabular template and the greater trochanter helps place the femoral template at the right level on each image. As compared to the present Image Overlay technique, the present Reverse Templating technique is less sensitive to how similar the images are, and therefore has a wider breadth of use as images can be taken in different settings, such as comparing a preop image taken in a physician's office with an intraop image taken during hip surgery involving a posterior approach or other surgical procedure.

In some implementations, a system and method according to the present invention analyzes images to provide guidance to optimize the restoration of orthopaedic functionality at a surgical site within a patient, including capturing, selecting or receiving: (i) at least a first, reference image along at least a first viewing angle including one of a preoperative image of the surgical site and a contralateral image on an opposite side of the patient from the surgical site; and (ii) at least a second, results image of the site, preferably also along the first viewing angle, after a surgical procedure has been performed at the site. The system and method further include generating on each of the first and second images at least two points to establish a stationary base on a stable portion of the surgical site and identifying at least one landmark on another portion of the surgical site spaced from the stationary base, and providing at least one of (a) an overlay of the first and second images to enable comparison of at least one of bone and implant alignment within the images, (b) matching of at least one digital template to at least one feature in each of the first and second images, and (b) a numerical analysis of at least one difference between points of interest, such as an analysis of at least one of offset, length differential and orientation of at least one of a bone and an implant within the images.

Figure 70:
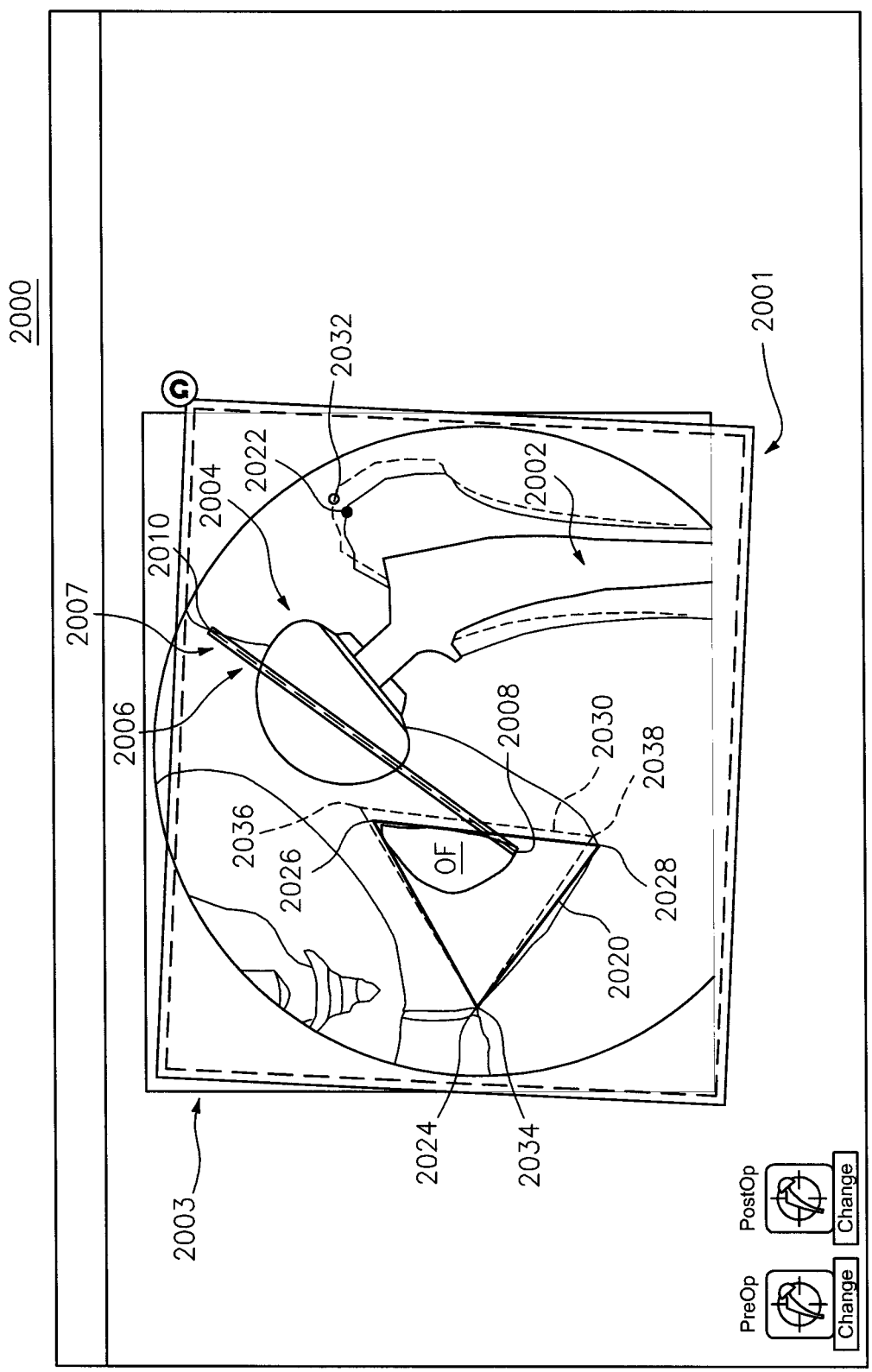
FIG. 70 is an image of a trial implant in a hip with the acetabular component transacted by a stationary base line and with two error analysis triangles.

Establishing at least three points for the stationary base, such as described below in relation to FIG. 70, is especially useful for determining rotational differences between images. One or more points may be shared with points establishing a scaling line. Preferably, at least one landmark is selected that is spaced from the stationary base points to increase accuracy of overlaying and/or comparing images.

In some constructions, scaling, which includes rescaling in some implementations, of at least one of the images is accomplished by measuring an anatomical feature during surgery, and comparing the measured feature to an initial, preoperative image which includes that feature. In other constructions, scaling or rescaling is accomplished by comparing an intraoperative image with at least one known dimension of (i) an implant feature, such as the diameter of an acetabular cup or a screw, or (ii) a temporarily-positioned object such as a ball marker or a tool such as a reamer. Typically, scaling or rescaling is accomplished by establishing two points on a feature, generating a line between the two points, and determining the correct length for the line.

In certain constructions utilizing implants, especially prostheses, the combination of accurately scaled templating, together with an innovative approach of combining a software-driven system according to the present invention with intra-operative medical imaging such as digital X-ray images, dramatically improves the accuracy of various surgeries, especially difficult-to-see anterior approach surgery for total hip replacement. The present invention enables a surgeon to compensate for unintended variations such as how a reamer or other tool interacts with a bone during preparation of the surgical site before or during insertion of the implant. In some constructions, the surgeon or other user is able to compare a pre-operative or intra-operative X-ray-type image of a patient's anatomy with an initial intra-operative X-ray-type image of a trial prosthesis, and deduce changes of offset and/or leg length to help guide surgical decision making. This unique process will greatly improve patient satisfaction by increasing the accuracy of direct anterior surgery and other types of surgeries, and greatly increase surgeon comfort in performing these less-invasive procedures.

In some implementations, a system and method according to the present invention includes an inventive alternative "Reverse Templating" methodology for analyzing parameters such as abduction angle, intraoperative leg length and offset changes using a different application of the stationary base, intraoperative scaling and anatomical landmark identification techniques. For Reverse Templating implementations, the system and method combines the use of intraoperative data, gathered from intraoperative image analysis, with intraoperative templating on a preoperative ipsilateral image. The method can be applied in a wider range of hip arthroplasty surgeries because it is less sensitive to inconsistencies in preoperative and intraoperative image acquisition, allowing the user to apply this system and method during arthroplasty in the lateral position (i.e. posterior approach). This alternative system and method also enables a user to precisely analyze, intraoperatively, how a potential change in implant selection would affect parameters such as abduction angle, offset and/or leg length. In this approach, described below in relation to FIGS. 60-69, the user will analyze the preoperative ipsilateral and intraoperative images 'side by side', without the need to overlap the images themselves. The system will scale and align these images relative to one another using at least intraoperative data, and then analyze offset and leg length changes by combining intraoperative data with a unique utilization of digital prosthetic templates.

For image analysis according to the present invention, preferably at least one stationary base and at least one anatomical landmark are selected. The term "stationary base", also referred to herein as a "stable base", means a collection of two or more points, which may be depicted as a line or other geometric shape, drawn on each of two or more images that includes at least one anatomical feature that is present in the two or more images of a region of a patient. For example, different images of a pelvic girdle PG of a patient, FIG. 1, typically show one or both obturator foramen OF and a central pubic symphysis PS, which the present inventors have recognized as suitable reference points or features for use as part of a stationary base according to the present invention. Other useful anatomical features, especially to serve as landmarks utilized according to the present invention, include femoral neck FN and lesser trochanter LT, shown on right femur $F_R$, and femoral head FH and greater trochanter GT shown on left femur $F_L$, for example. Femoral head FH engages the left acetabulum of the pelvic girdle PG. Also shown in FIG. 1 are ischial tuberosities IT at the bottom of the ischium, a "tear drop" TD relating to a bony ridge along the floor of the acetabular fossa, and the anterior superior iliac spine ASIS and the anterior inferior iliac spine AIIS of the ileum. As described below, carpal bones serve as a stationary base in images for radial bone fixation and other wrist-related procedures. In general, having a "non-movable" anatomical feature associated with the trunk of a patient is preferred for a stationary base, rather than a jointed limb that can be positioned differently among two or more images.

In general, a longer stationary base is preferred over a shorter stationary base, because the longer base, especially if it is a line, will contain more pixels in images thereof and will increase accuracy of overlays and scaling according to the present invention. However, the further the stationary base is from the area of anatomical interest, the greater the risk of parallax-induced error. For example, if the area of interest is the hip joint, then the ideal stationary base will be near the hip. In some procedures involving hip surgery, for example, a stationary base line begins at the pubic symphysis PS, touches or intersects at least a portion of an obturator foramen OF, and extends to (i) the "tear drop" TD, or (ii) the anterior interior iliac spine AIIS. Of course, only two points are needed to define a line, so only two reliable anatomical features, or two locations on a single anatomical feature, are needed to establish a stationary base utilized according to the present invention. More complex, non-linear stationary bases may utilize additional identifiable points to establish such non-linear bases.

Additionally, at least one identifiable anatomic "landmark", or a set of landmarks, is selected to be separate from the stationary base; the one or more landmarks are utilized in certain constructions to analyze the accuracy of the overlay process. This additional "landmark" preferably is part of the stationary anatomy being anatomically compared. For example, the inferior portion of the ischial tuberosity IT can be identified as an additional landmark. This landmark, in conjunction with the stationary base, will depict any differences or errors in pelvic anatomy or the overlay which will enable the physician to validate, or to have more confidence in, the output of the present system.

The term "trial hip prosthetic" is utilized herein to designate an initial implant selected by a surgeon as a first medical device to insert at the surgical site, which is either the right side or the left side of a patient's hip in this construction. In some techniques, the trial prosthetic is selected based on initial digital templating similar to the procedure described below for FIGS. 1A-3, for example.

One technique for accomplishing the present invention is described in relation to FIGS. 1A-3, which illustrate successive views or "screenshots" visible to a user of a system and method according to the present invention utilized for hip surgery. FIG. 1A is a schematic representation of a screen view 10 depicting a digital template image 20 of a prosthesis superimposed over the upper portion of a right femur $F_R$. In some techniques a digitized X-ray image of the hip region of a patient along a frontal or anterior-to-posterior viewing angle is utilized for screen view 10 and, in other techniques, a digital photograph "secondary" image of a "primary" X-ray image of the hip region of a patient along a frontal or anterior-to-posterior viewing angle is utilized for screen view 10. In one construction, screen view 10 is shown on a computer monitor and, in another construction, is shown on the screen or viewing region of a tablet or other mobile computing device, as described in more detail below. Dashed line SK represents skin of the patient and provides an outline of soft tissues for this viewing angle. Pelvic Girdle PG may also be referred to as a pelvis or hip.

Ball marker BM represents a spherical metal reference object of known dimension placed between right leg RL and left leg LL, as traditionally utilized to scale many types of medical images including X-ray images. Use of a ball marker or other non-anatomical feature is optional in techniques according to the present invention, as described in more detail below. In particular, the present invention is useful for unplanned trauma surgery, where direct measurement of an anatomical feature, such as caliper measurements of an extracted femoral head during emergency hip surgery, can be utilized by the present invention to intraoperatively guide such surgery.

Template image 20 is shown in greater detail in FIG. 1B with a body component 22 including a stem 24, a fastener recess 26, and a support 28 with a trunion 29, and an acetabular component 30 carried by support 28. Dashed line 32 indicates the longitudinal axis of support 28 and dashed line 34 indicates a longitudinal body axis for template image 20 to be aligned relative to a longitudinal axis of the femur F, as described in more detail below.

Additional icons and reference elements are provided in this construction, such as a reference line delete icon 40 for line 41, FIG. 1A, a template body delete icon 42 and an acetabular component delete icon 44 for body component 22 and acetabular component 30, FIG. 1B, respectively. One or more of these "virtual" items can be removed or added to view 10 by a user as desired by highlighting, touching or clicking the "soft keys" or "soft buttons" represented by the icons. In certain embodiments, one or more of the icons 40, 42 and/or 44 serves as a toggle to provide "on-off" activation or de-activation of that feature. Characters or other indicia 46, FIG. 1A, can be utilized to designate image number and other identifying information. Other useful information 48 can be shown such as Abduction Angle, Offset Changes and Leg Length Changes, as discussed in more detail below.

Figure 2:
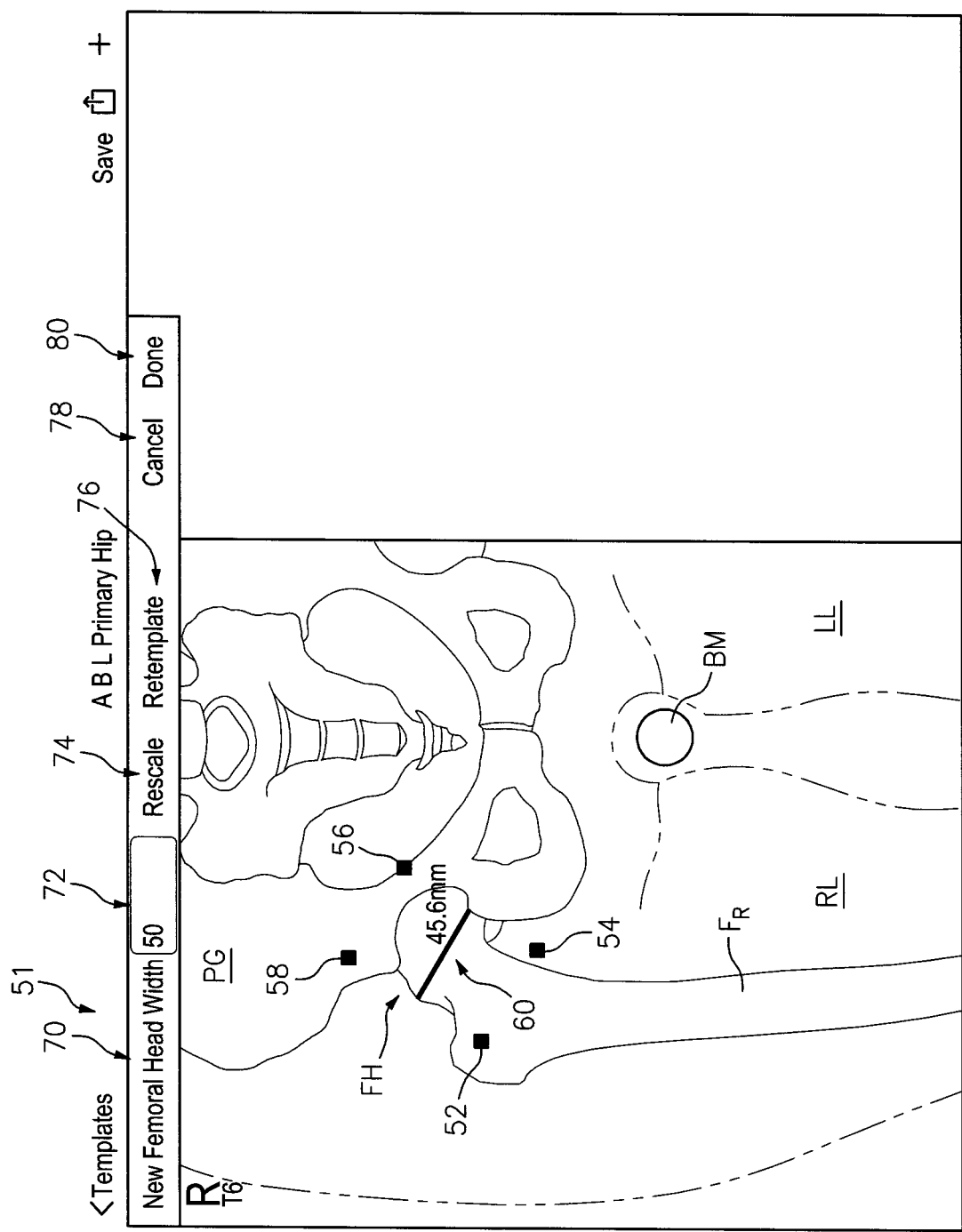
FIG. 2 is a image rendering similar to FIG. 1A after the digital template has been removed, illustrating measurement of a portion of the femoral head utilizing a reference line.

Screen view 51, FIG. 2, is similar to view 10 of FIG. 1A after the digital template 20 has been removed, illustrating measurement of a portion of the femoral head FH of femur $F_R$ utilizing a reference line 60. Four indicator squares 52, 54, 56 and 58, also referred to as reference squares, navigation handles, or navigation points, are provided in this construction to guide a user to draw the reference line 60 in the viewing plane of screen view 51. In some constructions, a user touches one of the squares 52-58 with a finger or a mouse cursor, and utilizes the square, such as by 'dragging' it, to move a marker to a desired location. This enables manipulation without blocking the location of interest.

Characters 70 such as "New Femoral Head Width" invite a user to enter a direct measurement into field 72, such as "50" to represent an actual 50 mm caliper measurement for the dimension represented by line 60, as described in more detail below. In this example, an initial scaling of image 51 had generated an estimated measurement of "45.6 mm" for line 60. Other functional "soft buttons" are "Rescale" 74, "Retemplate" 76, "Cancel" 78 and "Done" 80. In other constructions, as described in more detail below, intraoperative rescaling is conducted separately from a hip replacement process, and the direct measurement value, if needed, is utilized for intraoperative rescaling, for adjusting the template size, for comparing drawn lines, and other uses.

Direct measurement of the femoral head, such as with calipers, typically is conducted before a trial implant is inserted. The femoral head measurement enables (i) rescaling of the preoperative template or (ii) accurate scaling for the first time, especially where a preoperative template has not been utilized. During overlay analysis, however, scaling is accomplished in some constructions by measuring or looking up a dimension of an implant, such as the radius or width of the acetabular component of a hip prosthesis, for example.

Figure 3:
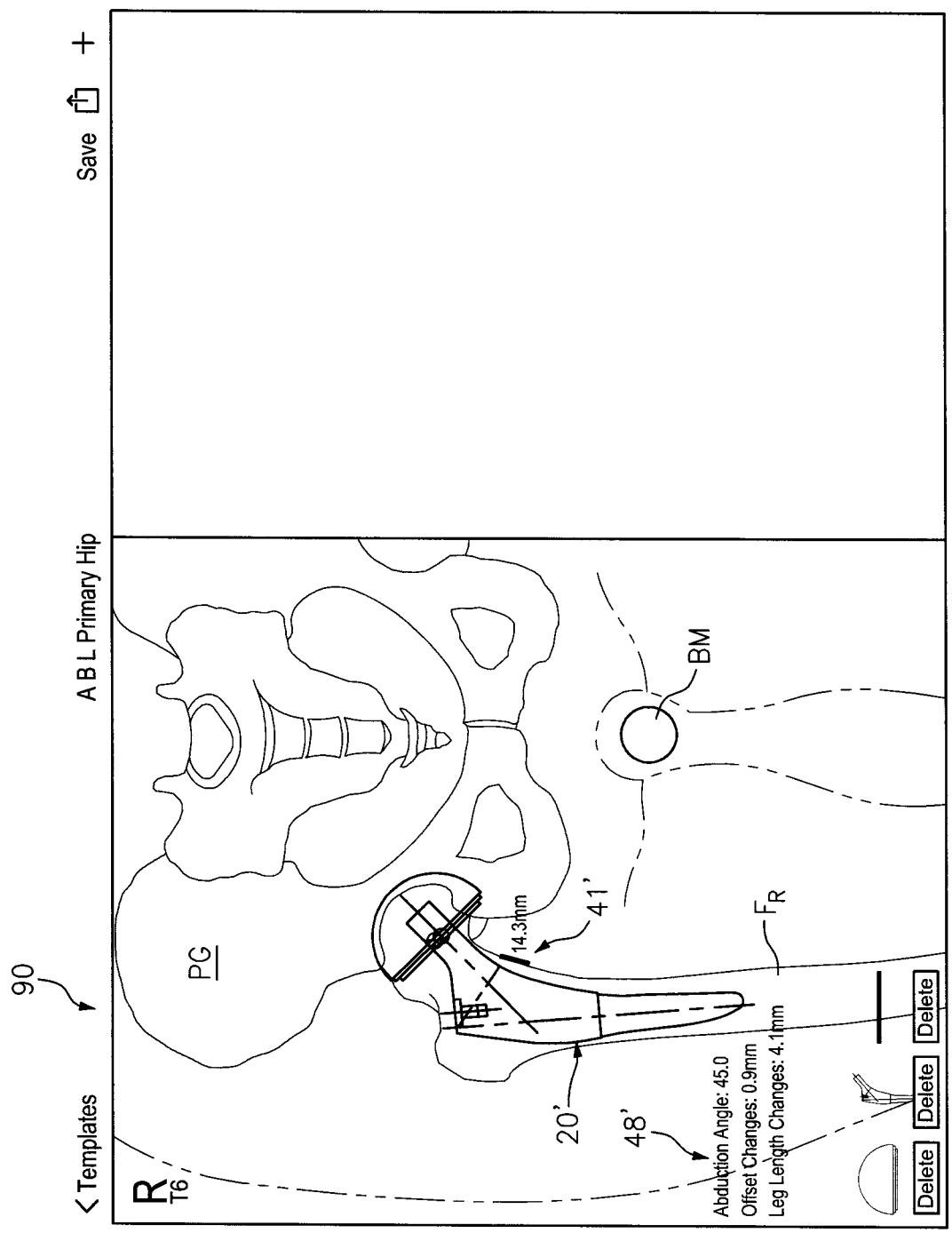
FIG. 3 is a image similar to FIG. 1A after the digital template has been re-scaled according to the present invention.

FIG. 3 is an image of a view 90 similar to view 10 of FIG. 1A, along the same viewing angle, after the digital template 20 has been re-scaled according to the present invention to a revised template 20'. In this example, reference line 41 was 13.1 mm in FIG. 1A, and reference line 41', FIG. 3, is now 14.3 mm as calculated by the system after re-scaling based on the direct measurement. Also, for revised information 48', the Offset Changes are re-calculated to be "0.9 mm" and the Leg Length Changes are recalculated to be "4.1 mm".

In one construction, the JointPoint Intraop™ system utilizes an interpolation mapping approach with one or more reference points or "landmarks" to achieve template auto-rescaling. Certain important landmarks on a X-ray image, or on a photograph of an X-ray image, are used to anchor each fragment of a template. This is the basic model:

$$\Sigma_0^m P_i = \Sigma_0^m f(p_i)$$ EQ. 1:

In this model, m is the number of landmarks, $P_i$ is landmark after interpolation mapping, and $p_i$ is the original landmark. $f(p_i)$ is the mapping function for rescaling.

$$f(p_i) = \frac{p_i - p_{1i}}{p_{2i} - p_{1i}}$$ EQ. 2 where $P_{i1}$ and $P_{i2}$ are two reference landmarks automatically provided by program based on the size of x-ray image.

$$p_{1i} = \lfloor p_i \times \text{ratio} \rfloor$$ EQ.3:

$$p_{2i} = \lceil p_i \times \text{ratio} \rceil$$ EQ.4:

Where "ratio" is the comparison of size of a regulator in a target x-ray image and a compared x-ray image. The regulator can be a ball marker, or a user-defined line or circle such as a circle drawn around an acetabular component.

$$\text{ratio} = \frac{\text{size of target regulator}}{\text{size of compared regulator}}$$ EQ. 5

By following the model indicated above, each of the template fragments lands in the same position when the size of a template is changed and, therefore, users avoid the need to replace templates every time a rescaling happens. Correct template placement can also be facilitated by storing coordinates of a particular location on the femoral component of a template, such as the midpoint of the top of the trunion 29 shown in FIG. 1B, for example.

Figure 4A:
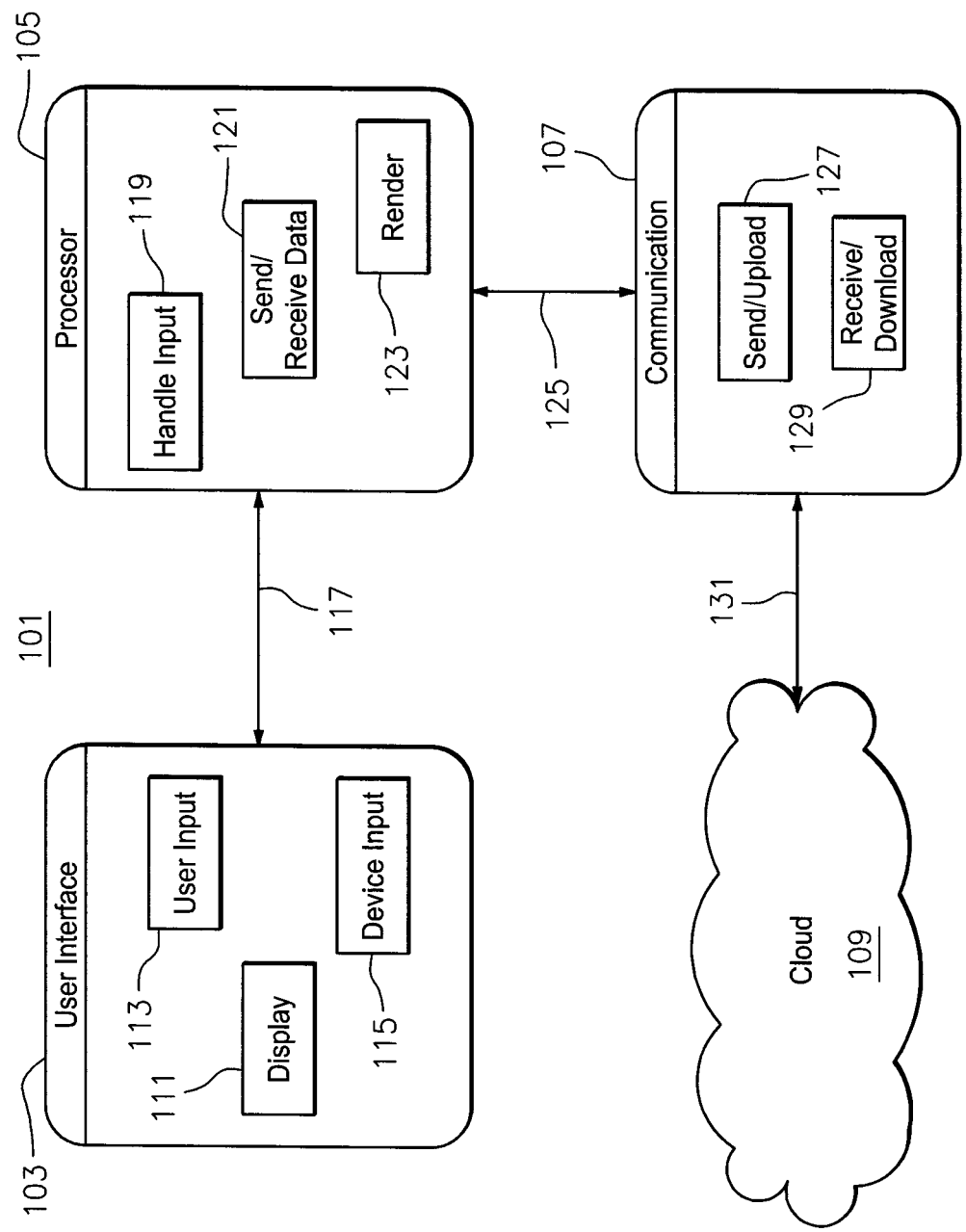
FIG. 4A is a schematic diagram of a system according to the present invention that interfaces with a user.

In one implementation, a system 101 according to the present invention, FIG. 4A, has a user interface 103, a processor 105, and a communications module 107 that communicates with a remote server and/or other devices via a cloud 109, which represents a cloud-based computing system. User interface 103 includes a display 111, a user input module 113 and device input 115 such as (i) a camera, to take a digital photo of a fluoroscopic imaging screen, also referred to as a "fluoro" image, or of a printed or otherwise fixed X-ray-type image, or (ii) a connection to a conventional medical imaging system (not shown). Display 111 is a separate computer monitor or screen in some constructions and, in other constructions, is an integrated touch-screen device which facilitates input of data or commands of a user to processor 105. In some constructions, user input 113 includes a keyboard and a mouse.

Processor 105 includes capability to handle input, module 119, to send and receive data, module 121, and to render analysis and generate results, module 123. Two-way arrows 117 and 125 represent wired or integrated communications in some constructions and, in other constructions, are wireless connections. Communications module 107 has a send/upload module 127 and a receive/download module 129 to facilitate communications between processor 105 and cloud 109 via wired or wireless connections 125 and 131, respectively.

In some constructions, the present invention provides the ability to accurately adjust implants and corresponding templates intra-operatively by combining mobile-based templating functionality, utilizing a mobile computing device such as a tablet, a Google Glass™ device, a laptop or a smart phone wirelessly interconnected with a main computing device, and a unique scaling technique translating real life intra-operative findings into selection of an optimally-configured implant for a patient. Preferably, the system includes a mode that does not require connection with a remote server, in the event of loss of internet connectivity or other extended system failure.

Figure 4B:
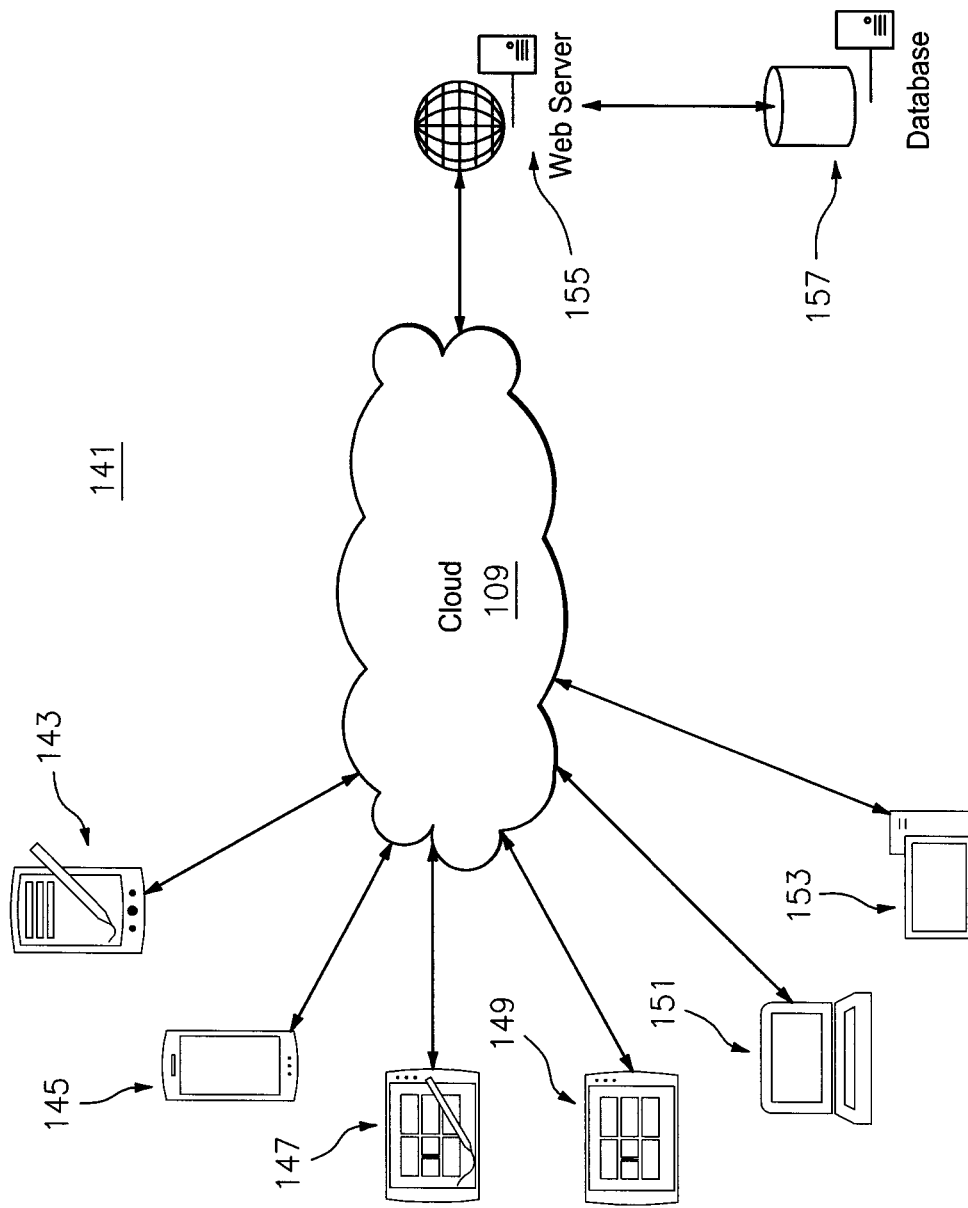
FIG. 4B is a schematic diagram illustrating how multiple types of user interfaces can be networked via a cloud-based system with data and/or software located on a remote server.

FIG. 4B is a schematic diagram of system 141 according to the present invention illustrating how multiple types of user interfaces in mobile computing devices 143, 145, 147 and 149, as well as laptop 151 and personal computer 153, can be networked via a cloud 109 with a remote server 155 connected through web services. Another useful mobile imaging and computing device is the Google Glass wearable device. Data and/or software typically are located on the server 155 and/or storage media 157.

Software to accomplish the techniques described herein is located on a single computing device in some constructions and, in other constructions such as system 141, FIG. 4B, is distributed among a server 155 and one or more user interface devices which are preferably portable or mobile.

Figure 4C:
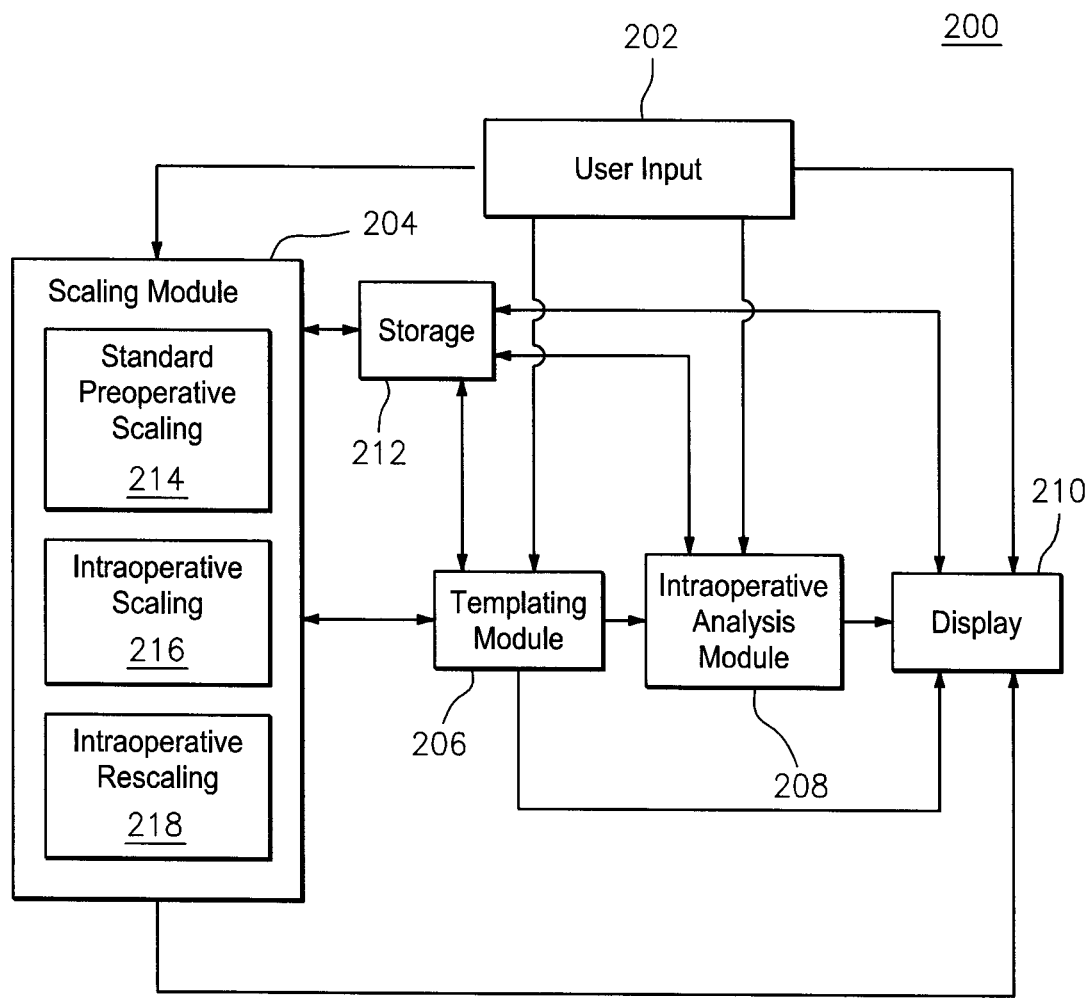
FIG. 4C is a high-level schematic diagram of a system according to the present invention.

A system 200 according to the present invention, FIG. 4C, includes a User Input Module 202 with one or more data items that are provided to a Scaling Module 204, a Templating Module 206, an Intraoperative Analysis Module 208, and a Display 210. Although Scaling Module 204 is illustrated and described as separate from Intraoperative Module 208 in some constructions, both Modules 204 and 208 can be considered as forms of analysis conducted according to the present invention utilizing a stationary base generated on at least two images. Further, User Input can be considered as a data input module that generates at least two points to establish a stationary base on at least one anatomical feature that is present in the images. In this construction, system 200 also includes a storage media 212 which receives and/or provides data to Modules 204, 206, 208 and Display 210. Scaling Module 204 includes Standard Preoperative Scaling unit 214, Intraoperative Scaling unit 216 and Intraoperative Rescaling unit 218 in this construction and provides data to Templating Module 206 and/or Display 210.

Figure 4D:
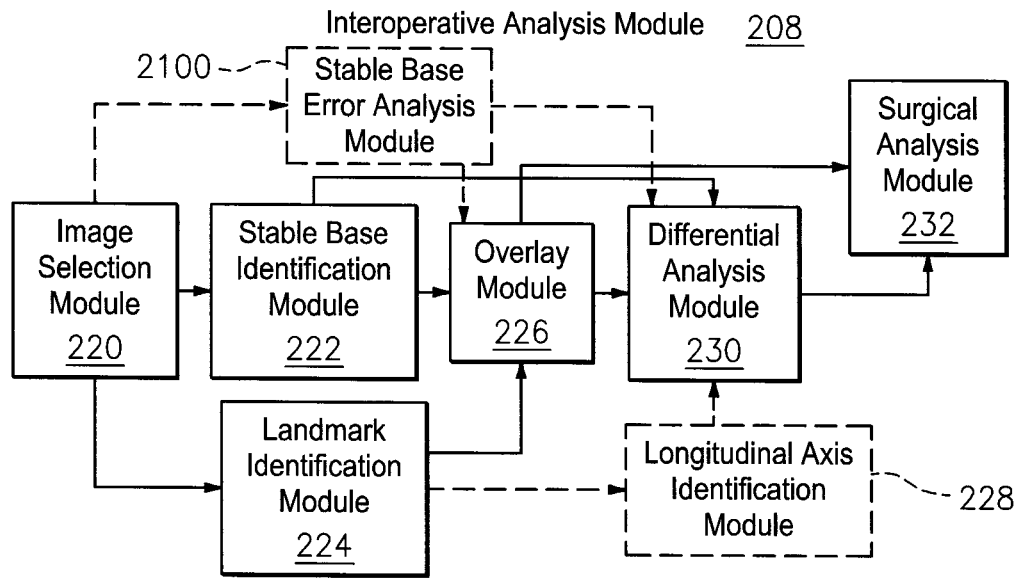
FIG. 4D is a schematic diagram of the Intraoperative Analysis Module in FIG. 4C.

The Intraoperative Analysis Module 208 is illustrated in more detail in FIG. 4D with an Image Selection Module 220, a Stable Base Identification Module 222 which guides the selection of at least one stationary base, and a Landmark Identification Module 224. Module 222 provides instructions to Overlay Module 226; Module 224 provides instructions to the Overlay Module 226 and/or to an optional Longitudinal Axis Identification Module 228, shown in phantom. When utilized, module 228 communicates with Differential Analysis Module 230 which in turn communicates with Surgical Analysis Module 232, shown in more detail in FIG. 4E. Overlay Module 226 communicates with Surgical Analysis Module 232 either directly or via Differential Analysis Module 230.

Also optional and present in some constructions in the Intraoperative Analysis Module 208 is a Stable Base Error Analysis Module 2100 that can provide outputs to Overlay Module 226 and/or Differential Analysis Module 230. When utilized, the Stable Base Error Analysis Module 2100 compares at least two images selected in Image Selection Module 220, and analyzes error or differences between the anatomic structures that contain the stationary base points. The module 2100 provides visual and/or quantitative data of image inconsistencies, such as shown in FIG. 70 below, providing guidance of how much value to place in the output of Intraoperative Analysis Module 208, FIGS. 4C and 4D. Within the module 2100, the system automatically, or the user manually, identifies one or more anatomic error reference points located within the anatomic structure selected to contain the stationary base. At least one of the error reference points, but preferably all of them, must be separate from the points utilized to establish the stationary base. The two images are scaled, rotated and transformed utilizing the stationary base according to the present invention. Because the error reference points identified in this module 2100 are separate from the stationary base points used to align the images, but are on the same non-movable anatomic structure, differences in error reference point location between the two images allow for the analysis within this module 2100. If the points seem extremely close, the anatomic structures are likely to be positioned very consistently between the two images being analyzed. If points are further apart, such as shown and described in relation to FIG. 70 below, then there are likely to be imaging and/or anatomic inconsistencies that may impact the data provided by the Analysis Module 208.

Figure 4E:
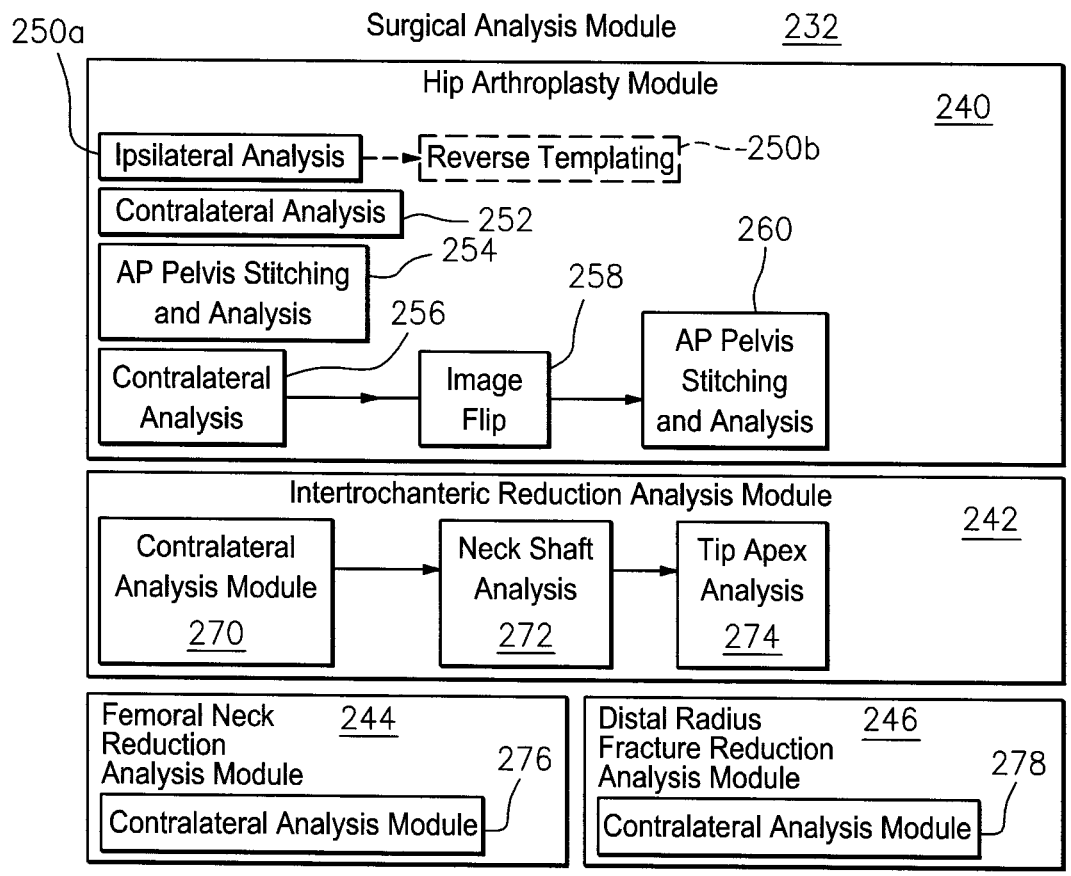
FIG. 4E is a schematic diagram of several variations of the Surgical Analysis Module in FIG. 4D.

FIG. 4E is a schematic diagram of several variations of the Surgical Analysis Module 232, FIG. 4D, depending on the surgical procedures to be guided according to the present invention. One or more of the following modules are present in different constructions according to the present invention: Hip Arthroplasty Module 240, Intertrochanteric Reduction Analysis Module 242, Femoral Neck Reduction Analysis Module 244 and/or Distal Radius Fracture Reduction Analysis Module 246. In the illustrated construction, the Hip Arthroplasty Module 240 includes at least one of an Ipsilateral Analysis unit 250*a*, a Contralateral Analysis unit 252, an AP Pelvis Stitching and Analysis unit 254 and an alternative Contralateral Analysis unit 256 which communicates with an Image Flip unit 258 and an AP Pelvis Stitching and Analysis unit 260. In some constructions, Ipsilateral Analysis module 250*a* optionally provides inputs to a Reverse Templating Module 250*b*, shown in phantom. Hip Arthroplasty is described in more detail below in relation to FIGS. 6-17, with AP Pelvis Stitching and Analysis described in relation to FIGS. 18-22 below.

Intertrochanteric Reduction Analysis Module 242 includes a Contralateral Analysis Module 270, a Neck Shaft Analysis unit 272 and a Tip Apex Analysis unit 274 in this construction. Femoral Neck Reduction Analysis Module 244 includes a Contralateral Analysis Module 276 in this construction. Intertrochanteric Reduction Analysis and Femoral Neck Reduction Analysis are described in combination with FIGS. 23-38 below.

Distal Radius Fracture Reduction Analysis Module 246 includes Contralateral Analysis Module 278 in this construction. Distal Radius Fracture Reduction is described in relation to FIGS. 39-51 below.

Figure 4F:
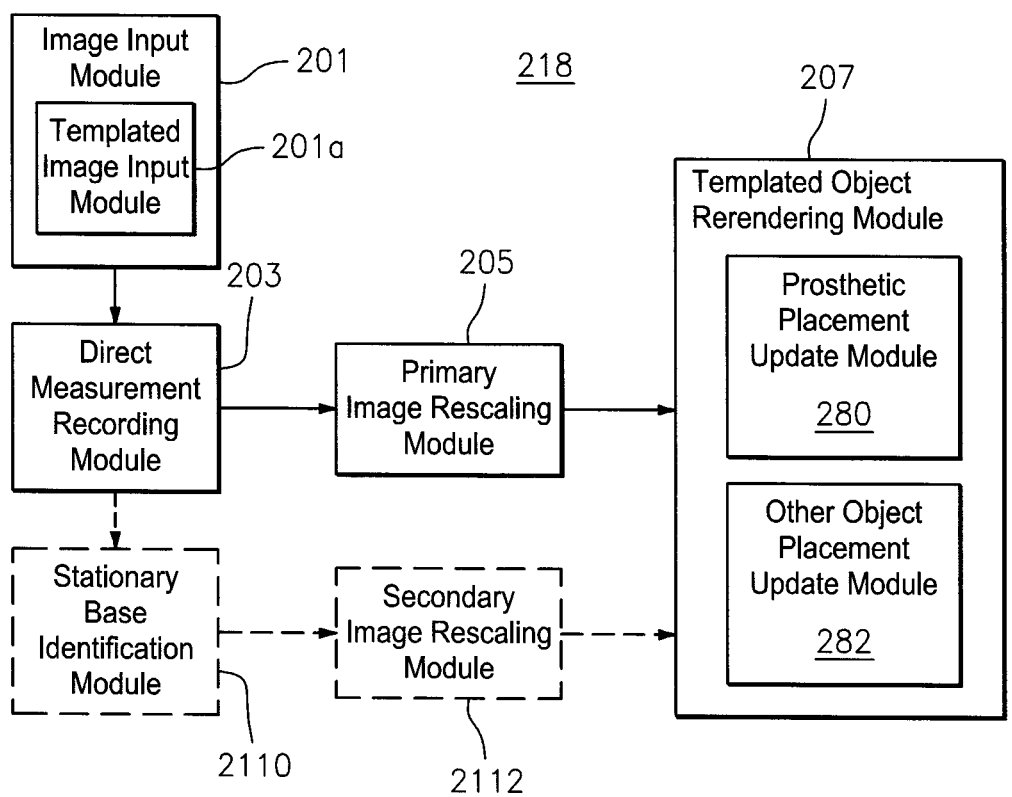
FIG. 4F is a schematic diagram of the Intraoperative Rescaling Module in FIG. 4C.
Figure 4G:
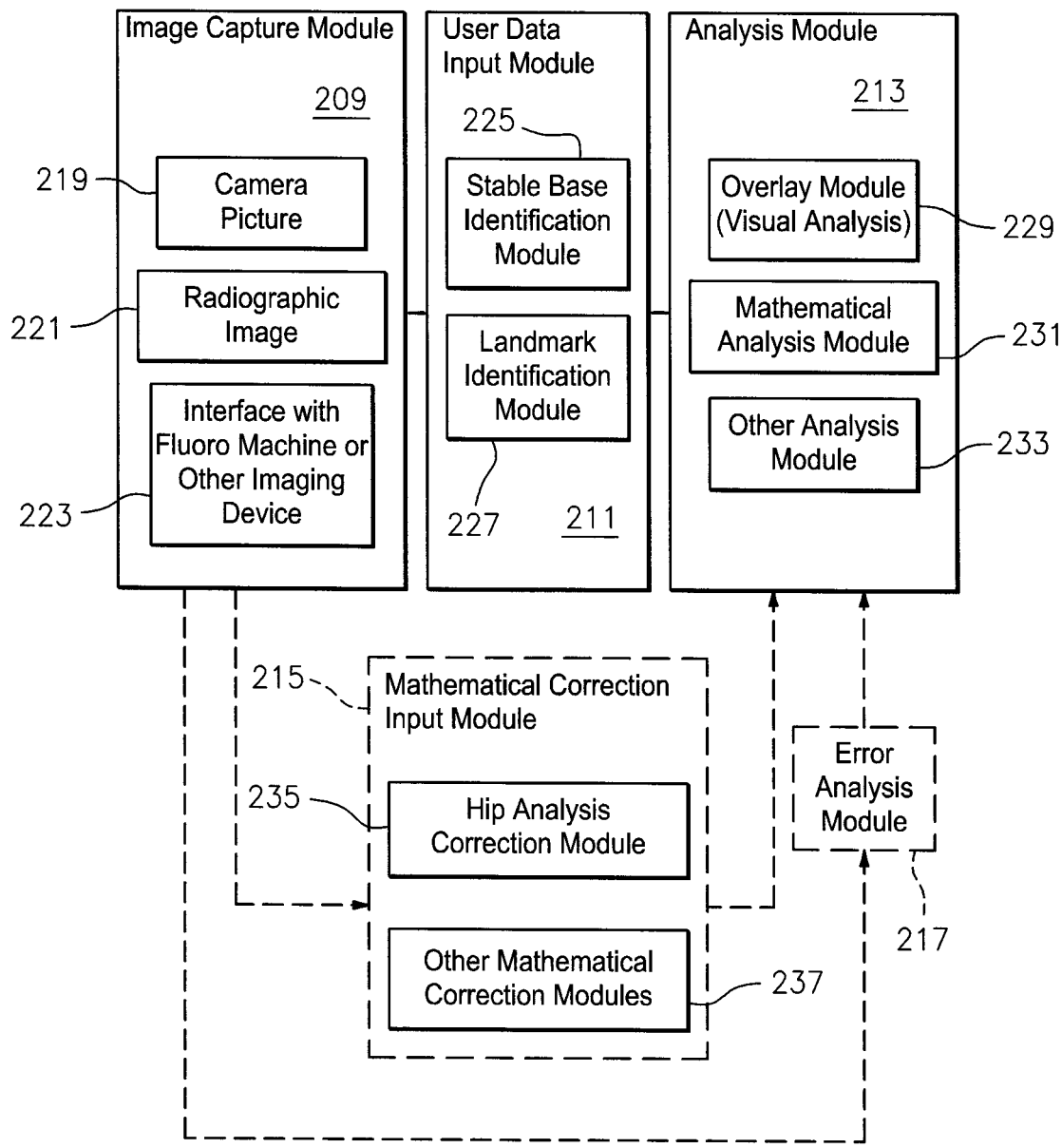
FIG. 4G is a schematic diagram of an alternative Intraoperative Analysis System according to the present invention.
Figure 4H:
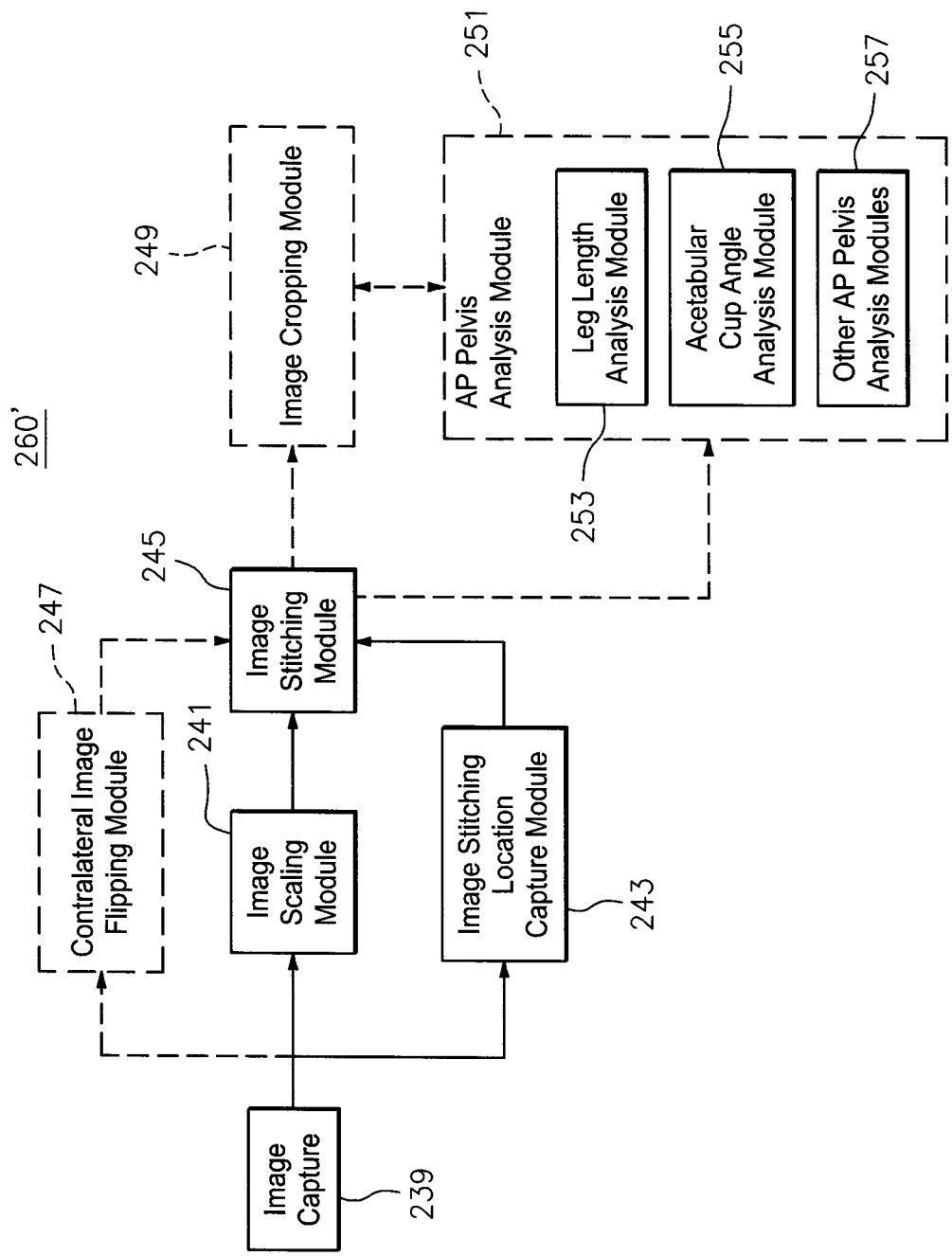
FIG. 4H is a schematic diagram of an AP (Anterior-Posterior) Pelvis Reconstruction System according to the present invention.

Three aspects of the present invention are represented by FIGS. 4F-4H for intraoperative rescaling, intraoperative analysis, and AP Pelvis reconstruction, respectively. FIG. 4F is a schematic diagram of the Intraoperative Rescaling Module 218, FIG. 4C, with Image Input Module 210 which contains Templated Input Module 201a, Direct Measurement Recording Module 203, Image Rescaling Module 205, and Template Object Re-rendering Module 207. A digital representation of a prosthesis, referred to as a "template", is provided to Template Input Module 201 in one construction and, in another construction, is generated by that Module 201. The digital template is provided to Direct Measurement Recording Module 203, which also records a direct measurement such as the width of the femoral head in one construction and, in another construction, utilizes a known implant dimension such as the width of a screw or the radius of the acetabular component of a hip prosthesis. The Image Rescaling Module 205 calculates possible adjustments in sizing that may be required. For example, if a first image of a hip depicted a femoral head as having a width of 48 mm, but direct measurement by calipers reveals that the true dimension is 50 mm, then the 2 mm discrepancy represents a four percent difference or deviation, and the first image is rescaled by four percent accordingly.

In some constructions, Re-rendering Module 207 includes a Prosthetic Placement Update Module 280 and/or, in certain constructions, an Other Object Placement Update Module 282 to re-render objects other than prostheses. Prosthetic Placement Update Module typically utilizes coordinate information, referred to herein as 'centroid' information, that is stored in a database and tells the system what reference point should remain stationary, relative to the image, during the rescaling process. Optionally, Intraoperative Rescaling Module 218 further includes a Stationary Base Identification Module 2110 and a Secondary Image Rescaling Module 2112, both shown in phantom, which can provide rescaling of the secondary image to Templated Object Re-rendering Module 207. These phantom modules facilitate the scaling of a second image based on directly observable measurements in the first image, if both images include a stationary base that identify the same anatomic points. More specifically, the first image is scaled directly via the Direct Measurement Recording Module 203, but this scaling is then applied to the second image by using the length ratios between the stable bases identified in Stationary Base Identification Module 2110.

An alternative Intraoperative Analysis System 208', FIG. 4G, includes an Image Capture Module 209, a User Data Input Module 211, and an Analysis Module 213. Optional additional capabilities include a Mathematical Correction Input Module 215 and an Error Analysis Module 217 as described in more detail below. Image Capture Module 209 preferably includes at least one of a Camera Picture input 219 for receiving or otherwise acquiring at least one photograph, a Radiographic Image input 221 for accessing a radiographic image from storage media or other location, and an Interface 223 which communicates with a fluoroscope or other medical imaging device to capture, receive or otherwise acquire an image in real time. At least one of inputs 219, 221 and/or 223 captures or otherwise acquires (i) at least one preoperative or contralateral reference image and (ii) at least one intraoperative or postoperative results image. The at least two images are provided to User Input Data Module 211 which utilizes a Stable Base Identification Module 225 to guide a user to select at least two stable base points, such as points on a pelvis, to generate a stable base on each image, and a Landmark Identification Module 227 to prompt the user to select a location spaced from and separate from the stable base, such as a location on the greater trochanter, on each image. Optionally, in certain constructions the Image Capture Module 209 also provides the images to the Error Analysis Module 217, which guides a user to select at least one point on the bony anatomy which contains the stable base points, to be analyzed for anatomical or imaging inconsistencies that could create error in the Analysis Module 213. An example of the operation of Error Analysis Module 217 is illustrated in FIG. 70 below, where the difference between two overlaid triangles, representing sets of three points in each image along the bony pelvis, is analyzed for pelvic alignment inconsistencies. These images with selected identifications are provided to the Analysis Module 213 which utilizes at least one of the following modules in this construction: Overlay Module 229 which utilizes visual analysis by the user and/or an image recognition program; Mathematical Analysis Module 231 which performs math calculations; or Other Analysis Module 233 which utilizes different visual change criteria or quantification analysis.

If anatomy of the patient being analyzed shifts or otherwise moves between capture of the at least two images, then optional Mathematical Correction Input Module 215 is beneficial to compensate for such movement. Hip Analysis Correction Module 235 is useful for hip surgery, such as by utilizing user identification of the femoral longitudinal axis in each image, while Other Mathematical Correction Modules 237 are utilized as appropriate for other anatomical regions of a patient undergoing surgery or other corrective treatment.

An alternative AP Pelvis Reconstruction System 260', FIG. 4H, utilizes Image Capture 239 to obtain an image of each side of a patient, such as both sides of a hip, both shoulders, or two images of other anatomy for which two locations are substantially symmetrical or otherwise comparable. The at least two images are provided to Image Scaling Module 241 and Image. Stitching Location Capture Module 243, which identifies corresponding locations such as the tip of the pubic symphysis in each image. After scaling and location identification by Modules 241 and 243, the images updated with that information are provided to Image Stitching Module 245 which generates an overlay as described in more detail below.

Optional modules include Contralateral Image Flipping Module 247 which reverses one of the images before it is provided directly to Image Stitching Module 245, or is provided indirectly via one or both of Image Scaling Module 241 and/or Image Stitching Location Capture Module 243. The output of a larger, stitched, overlay-type image from Image Stitching Module 245 can be provided directly to an AP Pelvis Analysis Module 251 or via an Image Cropping Module 249 to adjust the viewing area of the stitched image. In this construction, Analysis Module 251 includes one or more of Leg Length Analysis Module 253, Acetabular Cup Angle Analysis Module 255, and Other AP Pelvis Analysis Modules.

Figure 5:
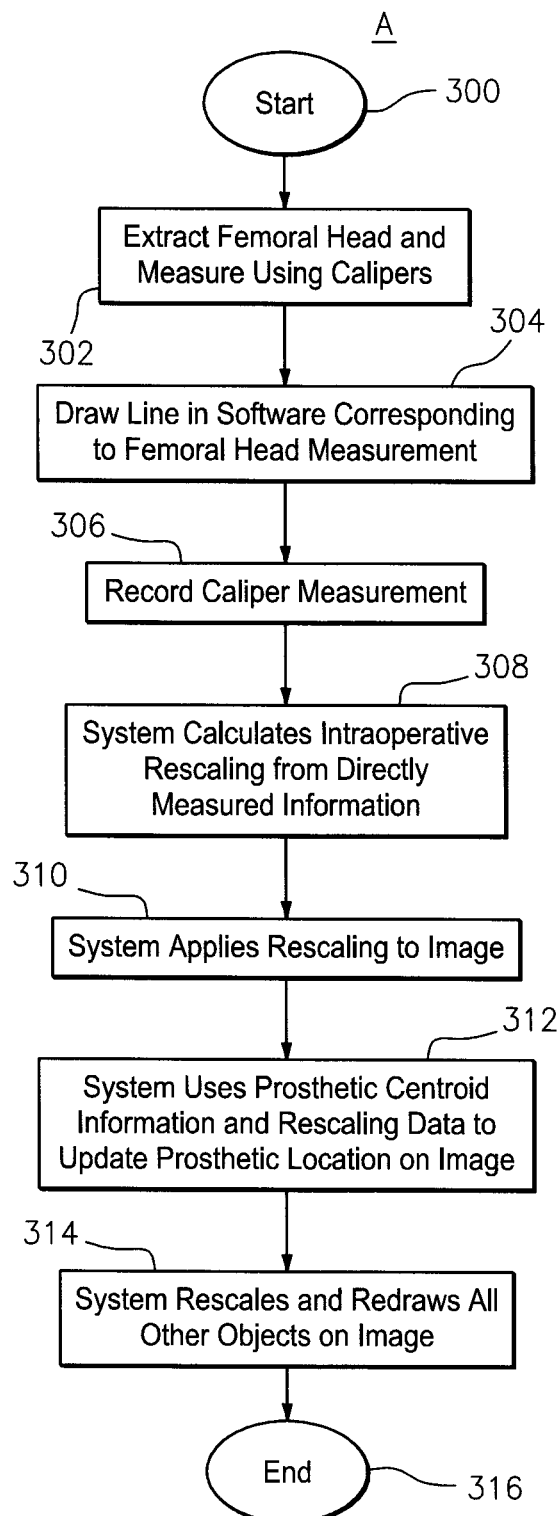
FIG. 5 is a Flowchart A for the operation of Intraoperative Rescaling in one construction of the system and method according to the present invention.

Flowchart A, FIG. 5, depicts the operation of Intraoperative Rescaling in one construction of the system and method according to the present invention related to hip surgery. The operation is initiated, as represented by "Start" in step 300, and the femoral head is extracted and measured using calipers, step 302. The technique proceeds to step 304, and a line is drawn in software corresponding to femoral head measurement such as illustrated in FIG. 2 above. The caliper measurement is recorded, step 306, FIG. 5, and the system calculates intraoperative rescaling from directly measured information, step 308. The system applies rescaling to the selected image, step 310, and, in one construction, uses prosthetic centroid information and rescaling data to update location of the prosthesis on the image. More generally, the system utilizes at least one selected point, such as the mid-point of the trunion, that is associated with the prosthetic template to identify where the prosthesis should remain stationary on the rescaled image. The system rescales and redraws all other objects on the image, step 314, and rescaling is concluded, step 316.

Figure 6:
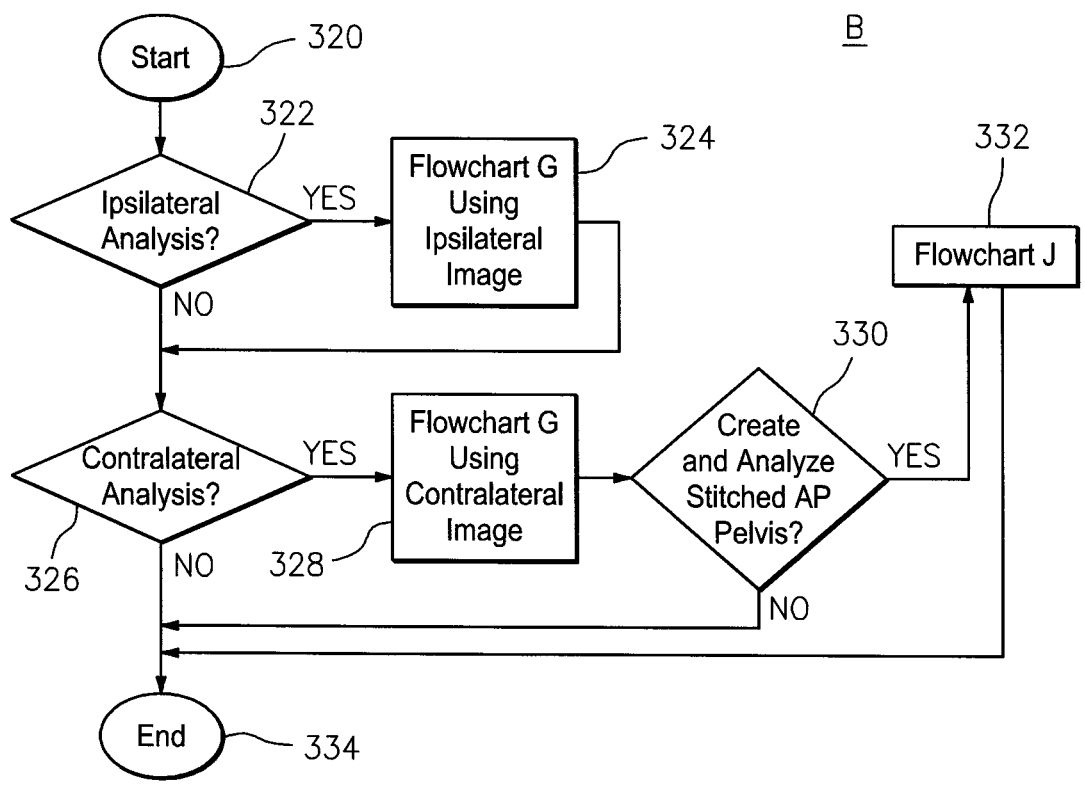
FIG. 6 is a Flowchart B for an Anterior Approach for hip surgery utilizing Flowcharts G and J.

Flowchart B, FIG. 6, illustrates an Anterior Approach for hip surgery utilizing Flowcharts G and J. This technique is commenced, step 320, and the decision whether to conduct ipsilateral analysis is made, step 322. If yes, Flowchart G is initiated, step 324; if no, then a decision is made whether to conduct Contralateral analysis, step 326. If yes, then Flowchart G is utilized, step 328, after which it is decided whether to create and analyze stitched AP Pelvis, step 330. If yes, then Flowchart J is activated. The Anterior Approach is concluded, step 334.

Figures 7, 8:
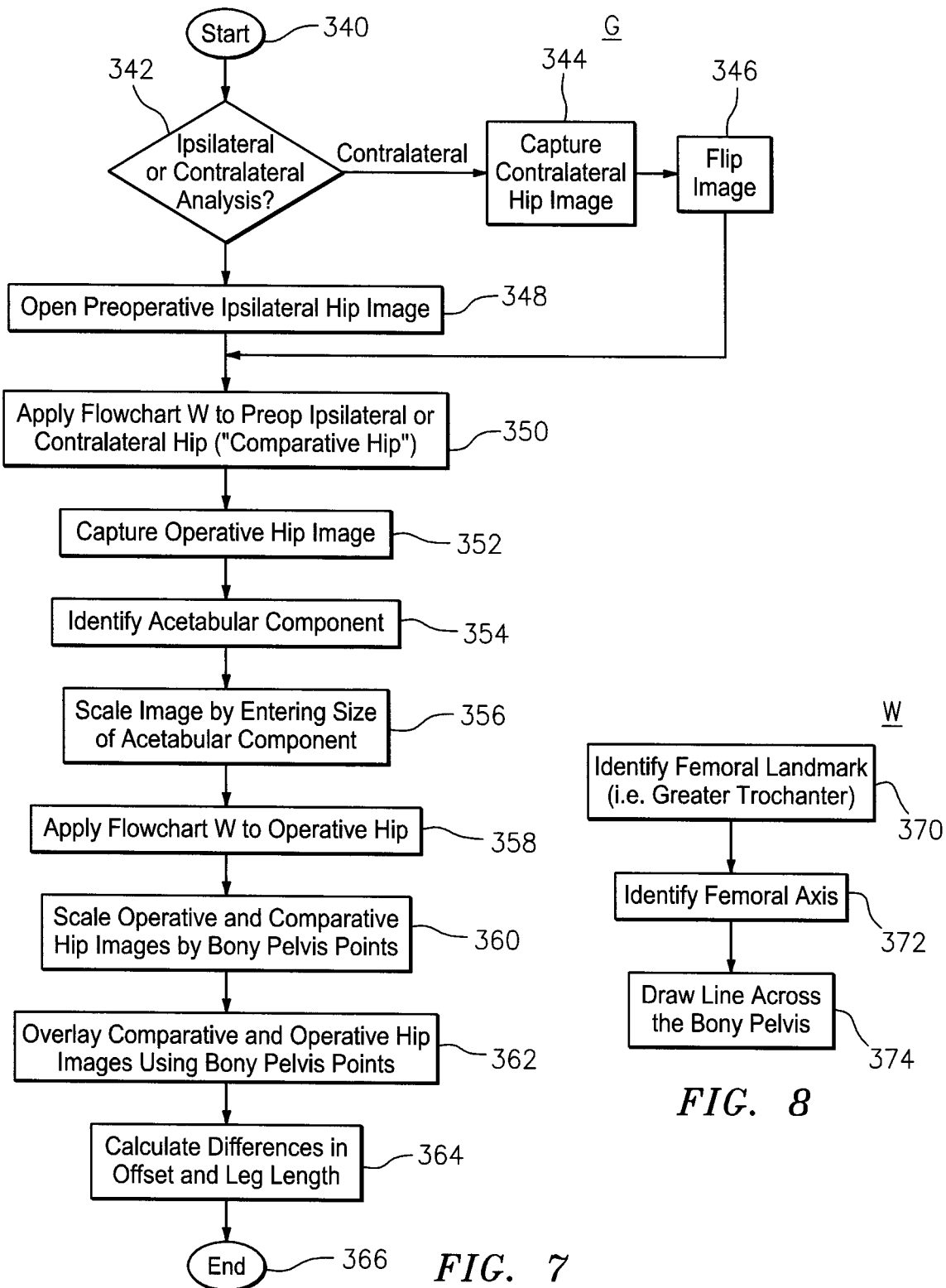
FIG. 7 is a Flowchart G showing technique flow for both contralateral and ipsilateral analysis.
FIG. 8 is a Flowchart W of several functions performed for hip analysis.

Flowchart G, FIG. 7, shows technique flow for both contralateral and ipsilateral analysis. This technique is commenced, step 340, and either contralateral or ipsilateral analysis is selected, step 342. For contralateral analysis, the contralateral hip image is captured, step 344, and the image is flipped, step 346. For ipsilateral analysis, the preoperative ipsilateral hip image is opened, step 348. For both types of analysis, Flowchart W is applied, step 350.

Figure 9:
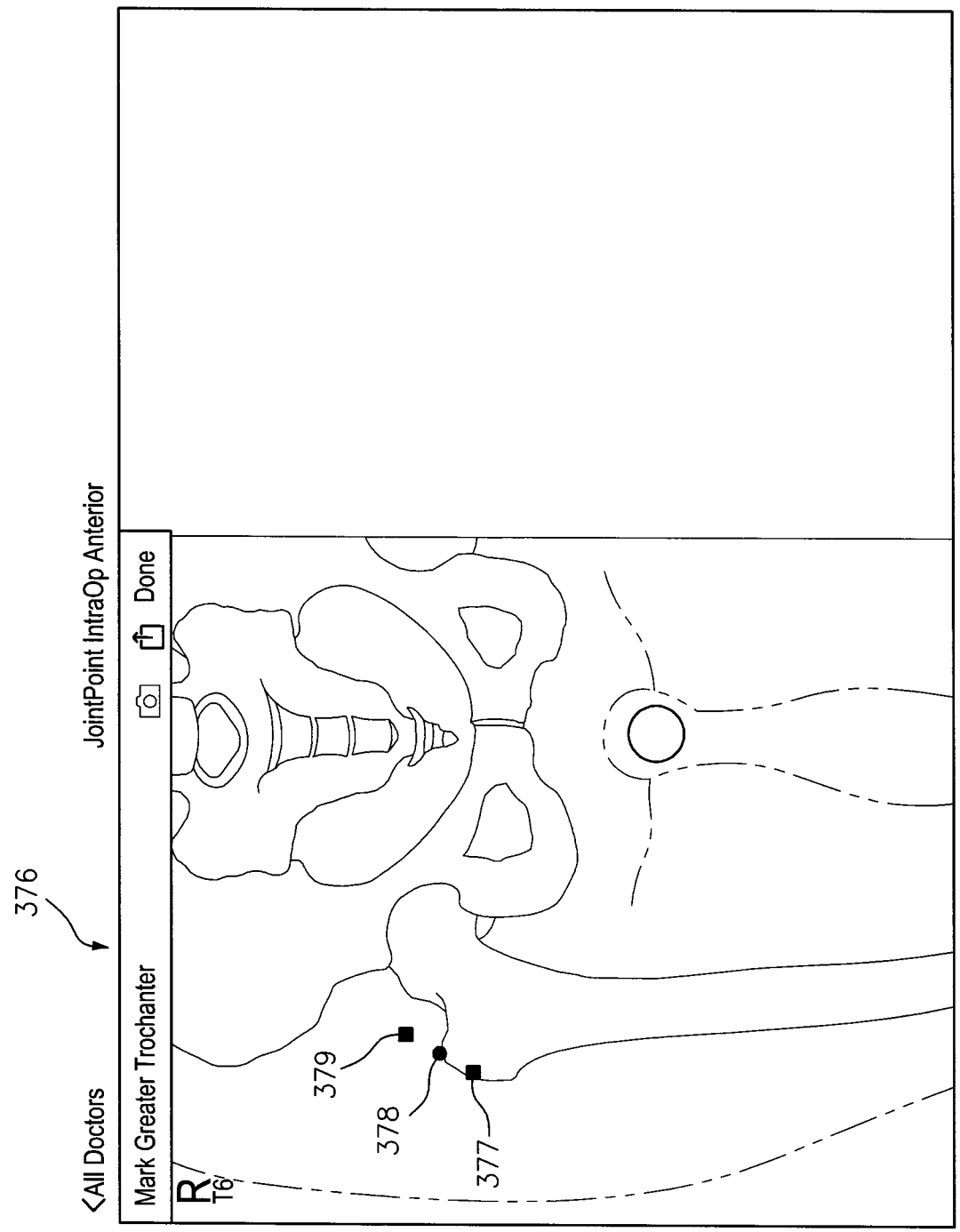
FIG. 9 is an image of the right side of a patient's hip prior to an operation and showing a marker placed on the greater trochanter as a landmark or reference point.
Figure 10:
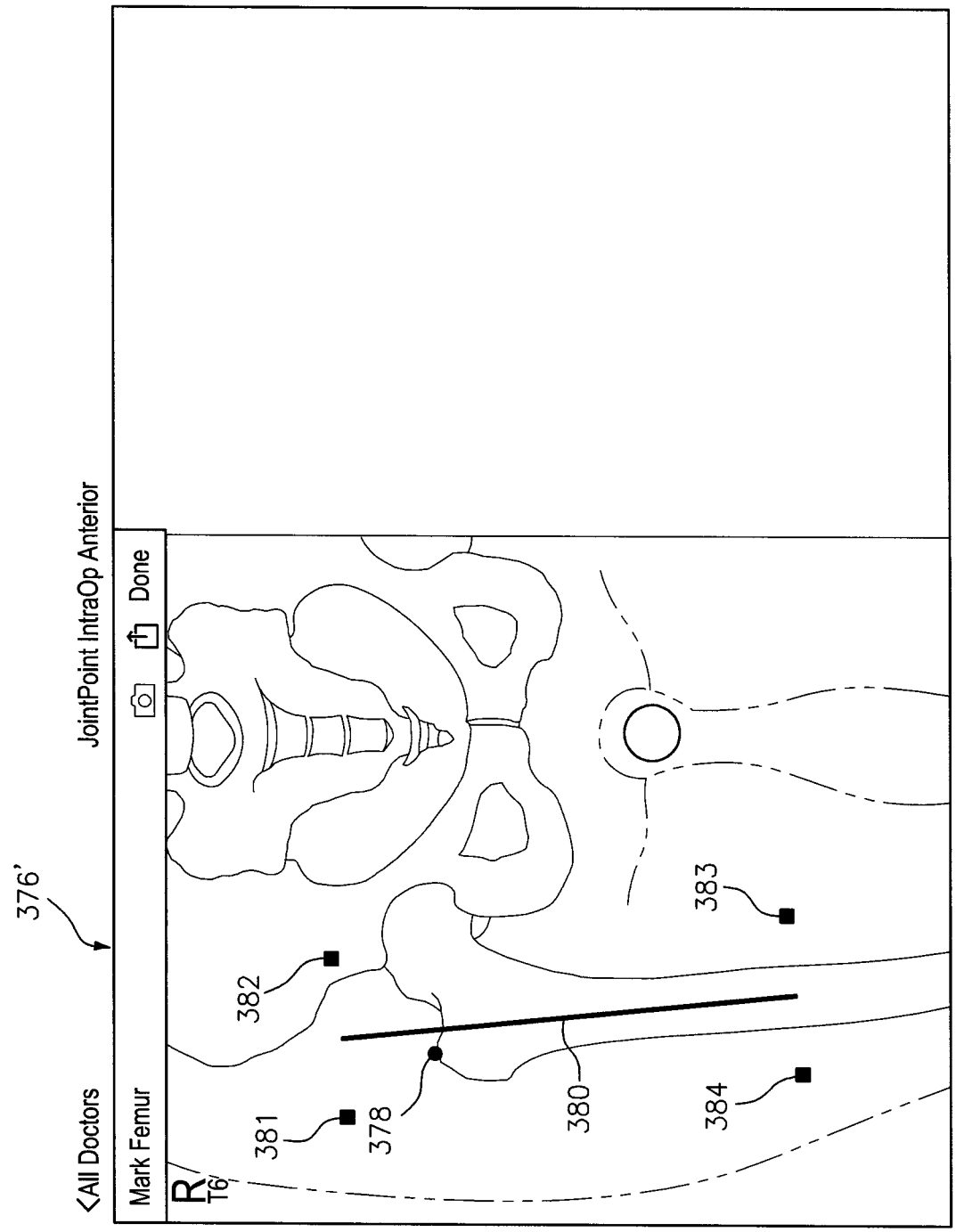
FIG. 10 is an image similar to FIG. 9 showing a reference line, drawn on (i) the pre-operative, ipsilateral femur or (ii) the contra-lateral femur, to represent the longitudinal axis of the femur.
Figure 11:
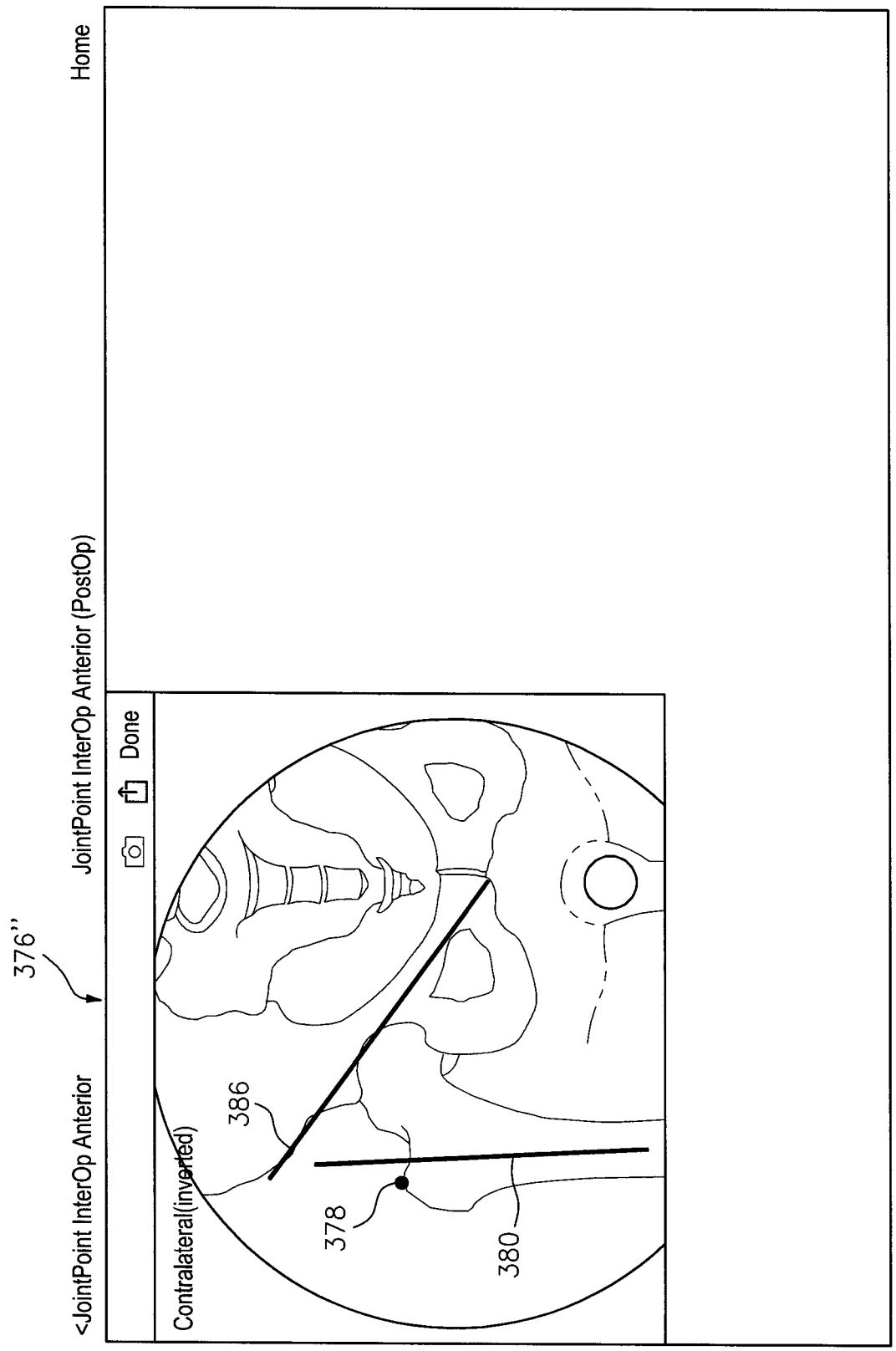
FIG. 11 is an image similar to FIG. 10 with a line drawn across the pelvic bone intersecting selected anatomical features.

Flowchart W, FIG. 8, after being activated by step 350, FIG. 7, guides a user to identify a femoral landmark such as the greater trochanter in step 370, FIG. 8, and then the femoral axis is identified, step 372. These steps are illustrated in FIGS. 9 and 10, below. A line is then drawn across the bony pelvis, step 374, as shown in FIG. 11.

Figure 12:
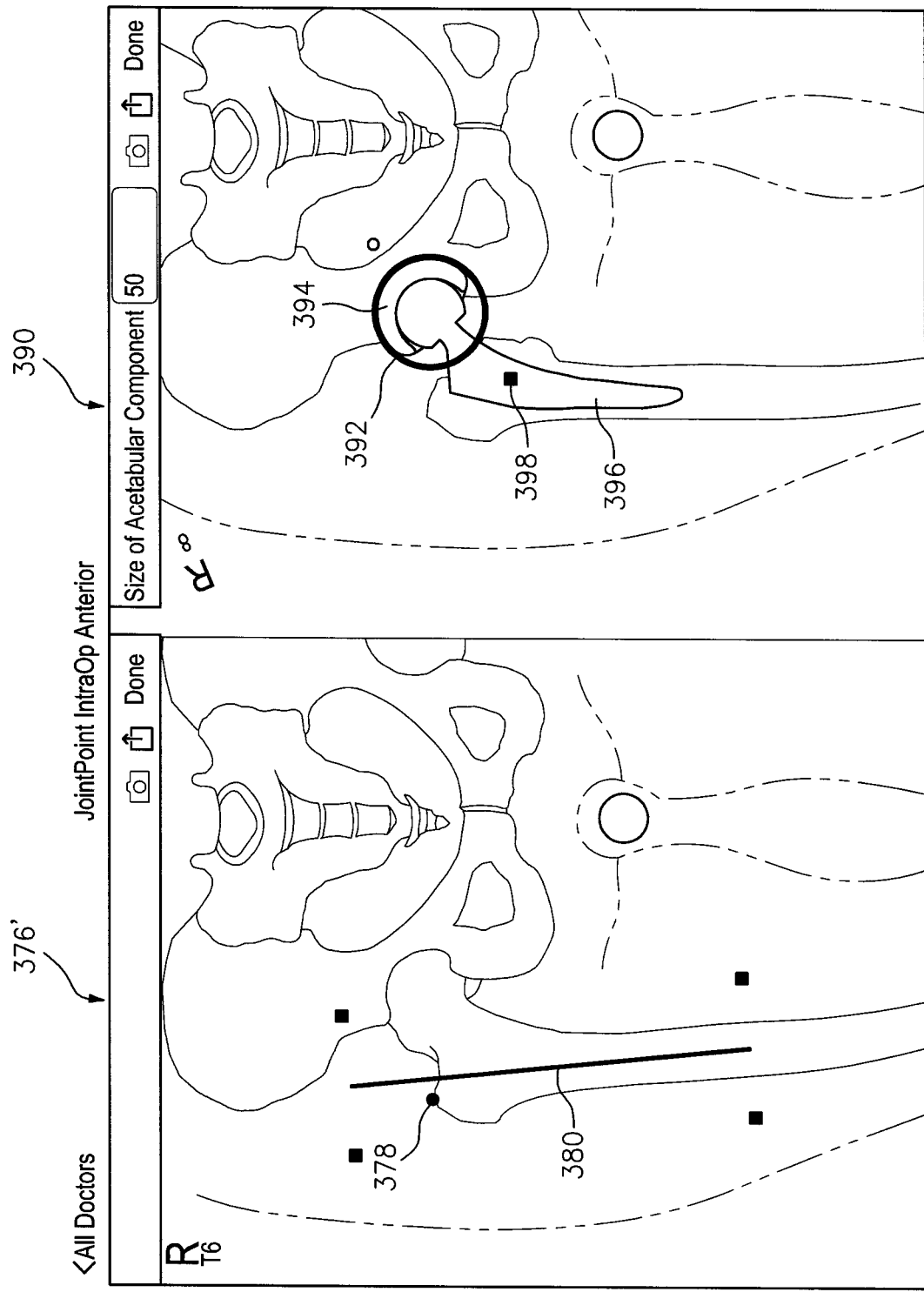
FIG. 12 is a schematic screen view of two images, the left-hand image representing a pre-operative view similar to FIG. 10 and the right-hand image representing an intra-operative view with a circle placed around the acetabular component of an implant to enable rescaling of that image.
Figure 15:
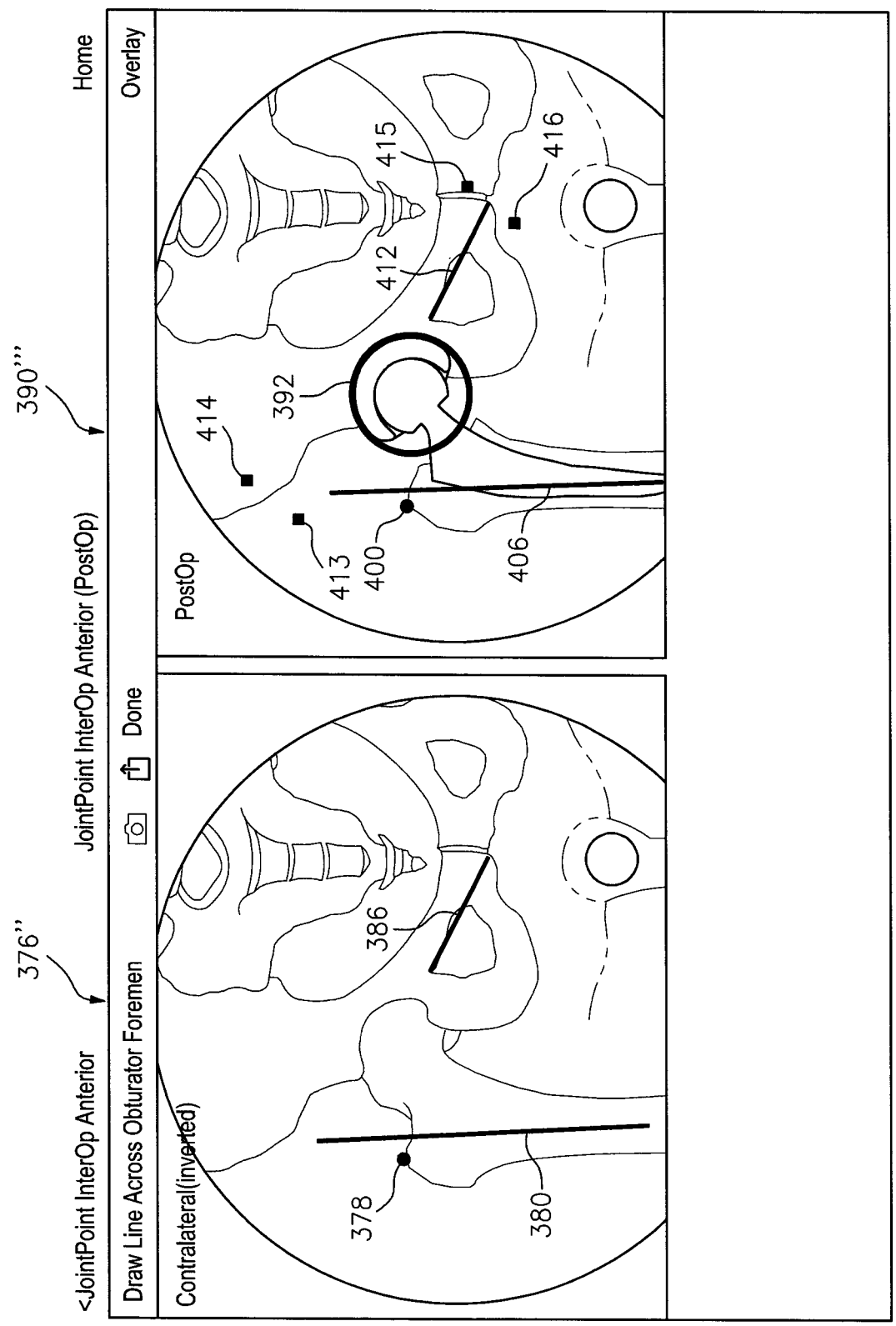
FIG. 15 is an image similar to FIGS. 11 and 14 with a line drawn across the obturator foramen in both pre- and intra-operative views.

The technique proceeds to capturing an operative hip image, step 352, FIG. 7, and identifying an acetabular component, step 354, such as shown in FIG. 12 below. Acetabular components are also shown in and discussed relative to FIGS. 52-53 and FIGS. 55-59 below. The image is scaled by entering the size of the acetabular component, step 356, and Flowchart W is then applied to the operative hip, step 358. The operative and comparative hip images are scaled by a stationary base generated by selecting at least two reference points on the bony pelvis, step 360, such as shown in FIG. 15. The scaled images are then overlaid in step 362 using the bony pelvis points, such as the overlaid lines 386 and 412 shown in FIG. 16. Differences in offset and leg length are calculated, step 364, and the technique is terminated, step 366, returning to step 326, FIG. 6, for ipsilateral comparison or to step 330 for contralateral comparison.

Leg displacement is calculated in the pre-operation and post-operation (intra-operation) to give users a visualization of the operation process. The following steps 1-6 with Equations 6-10 are utilized in one construction:

1. Draw a landmark, such as a single point or dot to represent a feature such as the greater trochanter, and a "stationary base" generated by selecting at least two points on the bony pelvis in each of the pre-op image and post-op x-ray image.
2. One procedure for aligning two images utilizing corresponding stationary bases, each base comprised of precisely two points that define a line, is accomplished by the following approach. Based on the positions of zero coordinate in each x-ray image, translate the line segment position into screen coordinate system. $P_{original}$ is the point's coordinate on each image's coordinate plane. $Z_{screen}$ is the coordinate of zero in each image on the screen coordinate plane.

$$P_{screen}=P_{original}+Z_{screen} \quad \text{EQ. 6}$$

3. Find the rotation angle θ between the two line segment $line_{postop}$ and $line_{preop}$ are the line vector of each line segment.

$$\theta = \cos^{-1} \frac{|\langle line_{postop} \cdot line_{preop}\rangle|}{\|line_{preop}\|\|line_{preop}\|} \quad \text{EQ. 7}$$

4. Calculate the rotation matrix R and apply it to the landmark in pre-op image. $lm_{preop}$ is the center point position of landmark, $lm'_{preop}$ is the center point position of landmark after rotation.

$$R = \begin{pmatrix} \cos\theta & \sin\theta \\ \sin\theta & -\cos\theta \end{pmatrix} \quad \text{EQ. 8}$$

$$lm'_{preop} = R * lm_{preop}$$

5. Calculate the length ratio S between the two line segments and scale the pre-op image based on it to get the landmark position after scaling. Use of more than two points for a stationary base benefits from a 'best fit model' approach, such as an algorithm that minimizes the distance between respective points in each of the images.

$$S=length_{postop}/length_{preop}$$

$$lm''_{preop}=S*lm'_{preop} \quad \text{EQ. 9}$$

6. Finally, calculate the distance of the two landmark in both horizontal and vertical direction, visualize the results along with the two overlaid x-ray images.

$$\{offset, leg\ length\}=lm_{postop}-lm''_{preop} \quad \text{EQ. 10}$$

A currently preferred implementation of the JointPoint IntraOp™ Anterior system, which provides the basis for intraoperative analysis of the anterior approach to hip surgery, is illustrated in relation to FIGS. 9-22. FIG. 9 is an image 376 of the right side of a patient's hip prior to an operation and showing a marker 378, bracketed by reference squares 377 and 379, placed by a user as guided by the system, or placed automatically via image recognition, on the greater trochanter as a landmark or reference point, such as indicated in box 224, FIG. 4D and in box 227, FIG. 4G, for the Landmark Identification Module of systems 208 and 208', respectively. FIG. 10 is an image 376' similar to FIG. 9 showing a reference line 380, bracketed by reference squares 381, 382, 383 and 384, drawn on (i) the pre-operative, ipsilateral femur or (ii) the contra-lateral femur, to represent the longitudinal axis of the femur. FIG. 11 is an image 376" similar to FIG. 10 with a line 386, defined by two end-points, which is drawn across the pelvic bone intersecting selected anatomical features.

Figure 13:
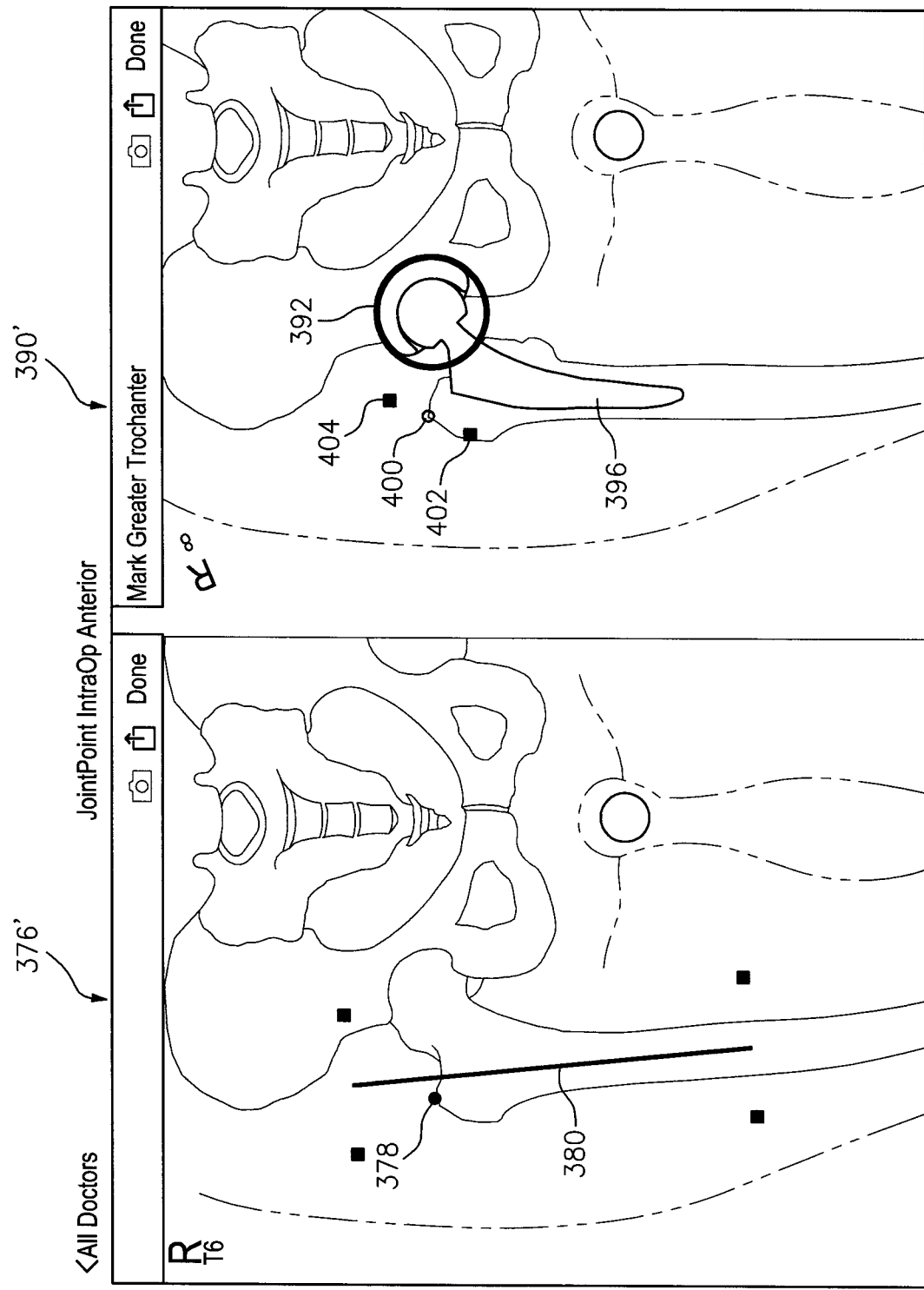
FIG. 13 is a schematic screen view similar to FIG. 12 indicating marking of the greater trochanter of the right-hand, intra-operative image as a femoral landmark.
Figure 14:
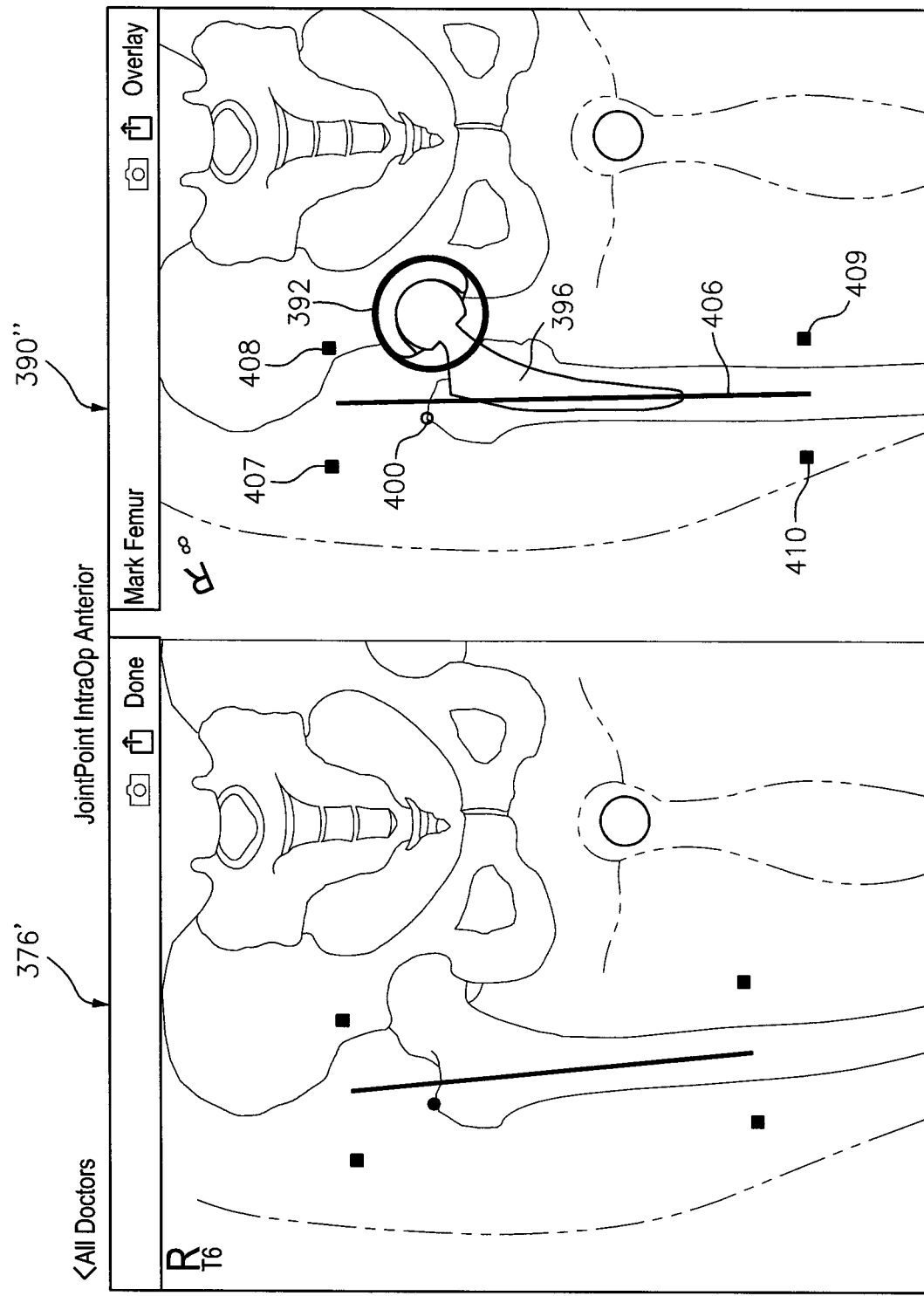
FIG. 14 is a schematic screen view similar to FIG. 13 with a reference line drawn on the intra-operative femur in the right-hand view.

FIG. 12 is a schematic screen view of two images, the left-hand image 376' representing a pre-operative view similar to FIG. 10 and the right-hand image 390 representing an intra-operative view with a circle 392 placed around the acetabular component 394 of an implant 398 to enable rescaling of that image. In some constructions, circle 392 is placed by an image recognition program and then manually adjusted by a user as desired. Reference square 398 designates implant 398 to the user. FIG. 13 is a schematic screen view similar to FIG. 12 indicating marking of the greater trochanter of the right-hand, intra-operative image 390' as a femoral landmark 400, guided by reference squares 402 and 404. FIG. 14 is a schematic screen view similar to FIG. 13 with a reference line 406 drawn on the intra-operative femur in the right-hand view 390", guided by reference squares 407, 408, 409 and 410.

FIG. 15 is an image similar to FIGS. 11 and 14 with a line 386, 412 drawn across the obturator foremen in both pre- and intra-operative views 376" and 390''', respectively. Reference squares 413, 414, 415 and 416 guide the user while drawing reference line 412.

Figure 16:
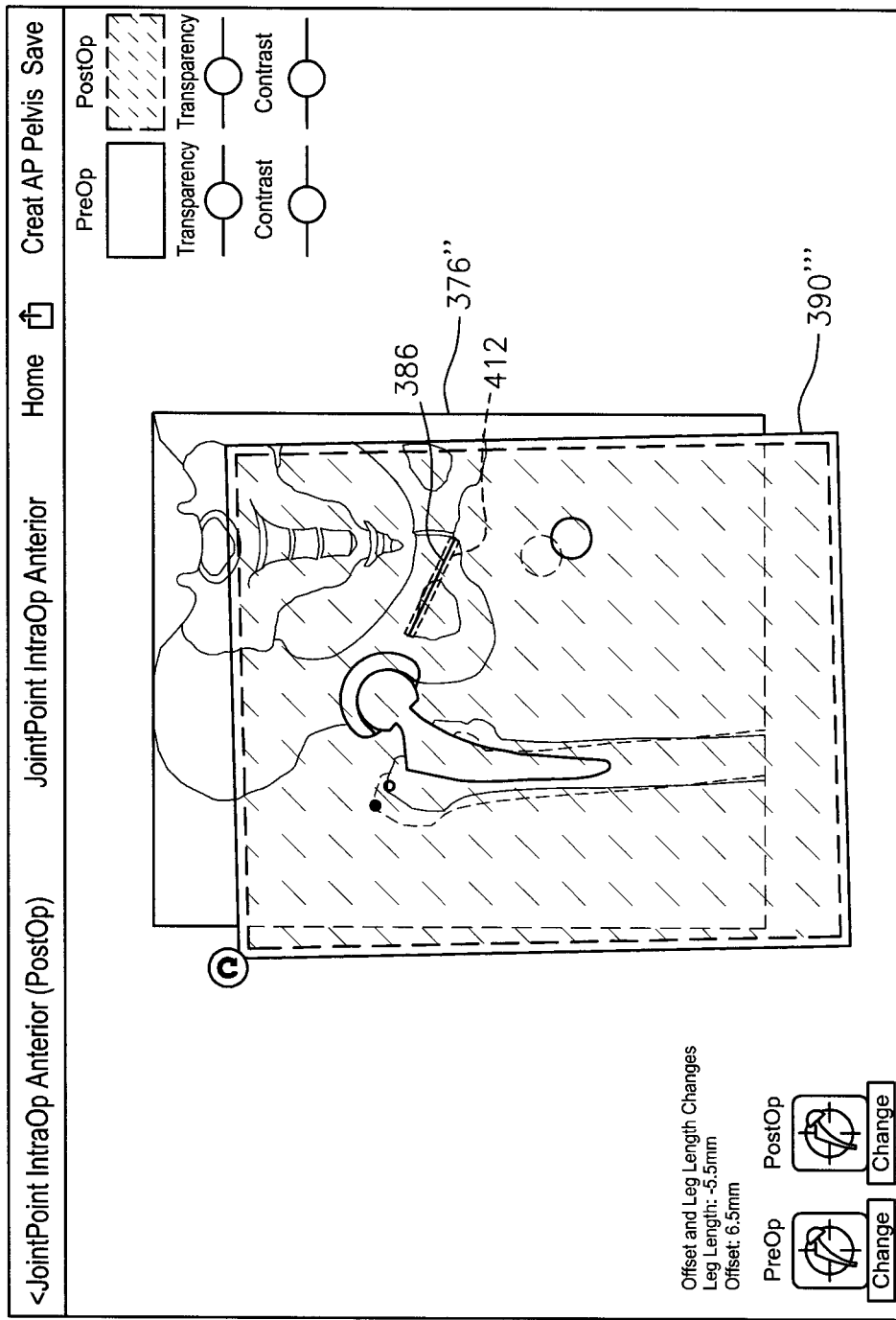
FIG. 16 is an overlay image showing the right-hand, intra-operative image of FIG. 15 superimposed and aligned with the left-hand, pre-operative image.

FIG. 16 is an overlay image showing the right-hand, intra-operative, PostOp image 390''' of FIG. 15 superimposed and aligned with the left-hand, pre-operative PreOp image 376". In this construction, soft button icons for selectively changing PreOp image 376" and/or PostOp image 390''' are provided at the lower left-hand portion of the screen.

Figure 52:
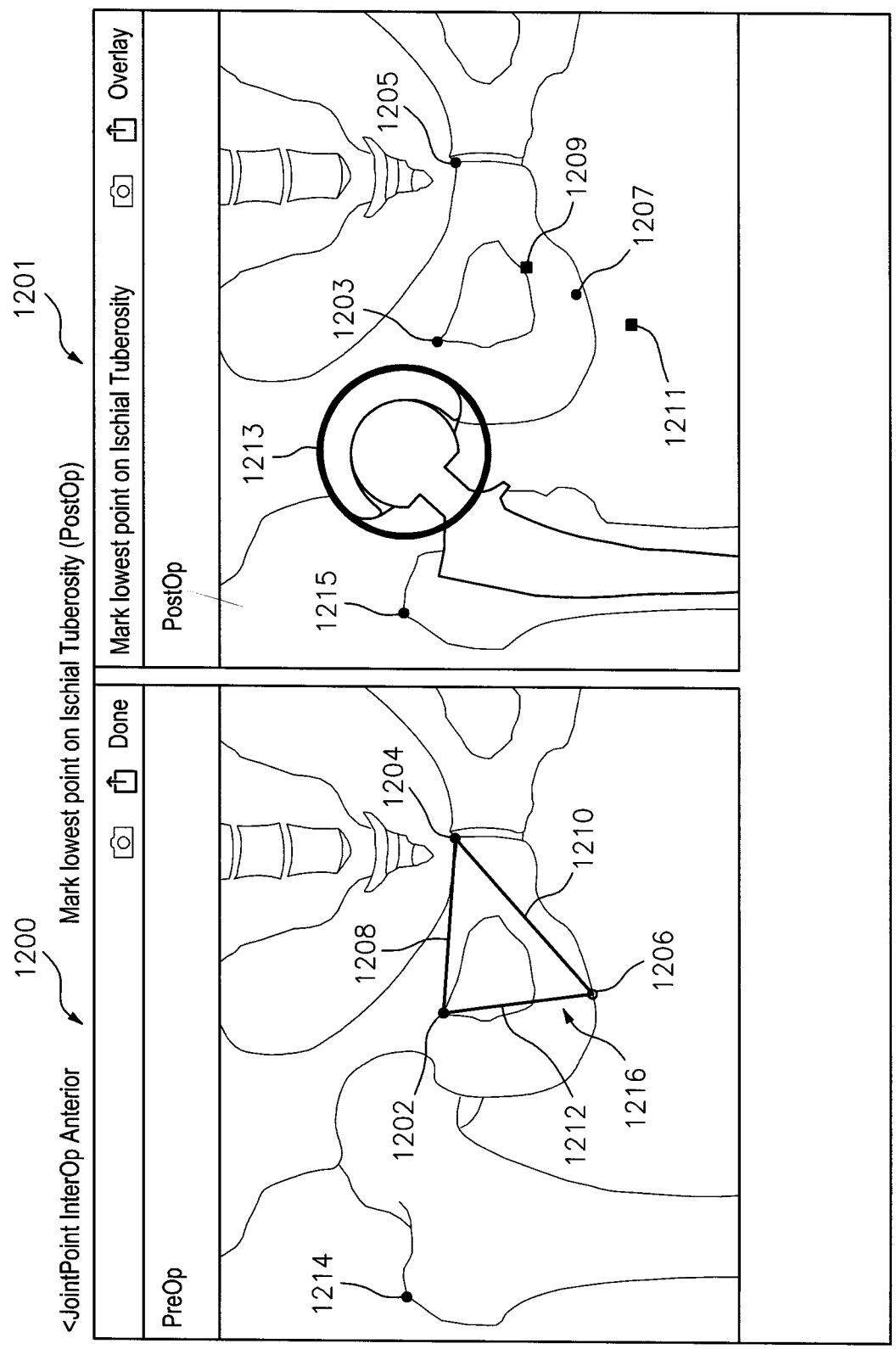
FIG. 52 is an image similar to FIG. 15 with points marking the lowest point on the ischial tuberosity and points marking the obturator foramen and top of the pubic symphysis in both pre- and intra-operative views.
Figure 53:
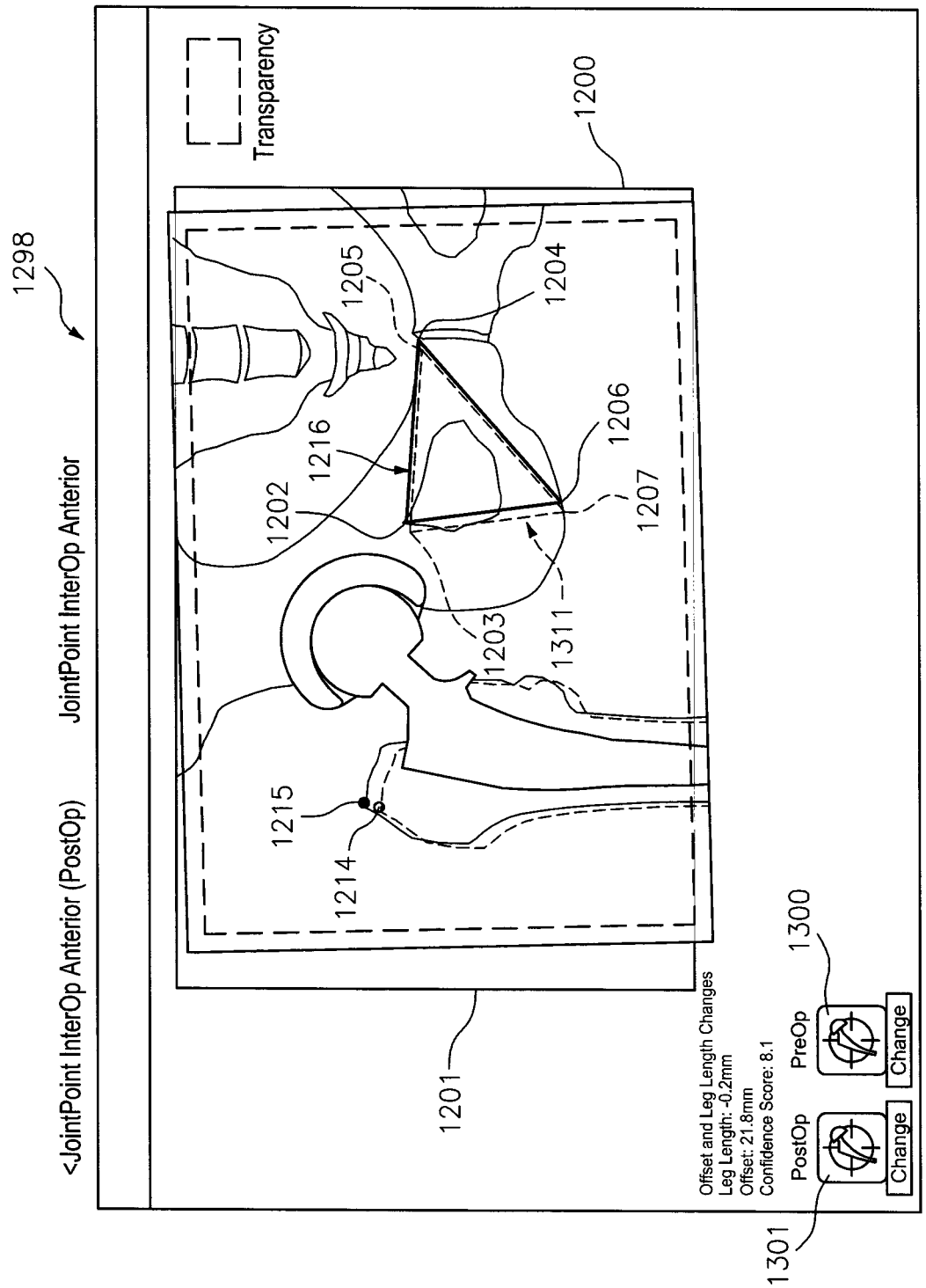
FIG. 53 is an overlay image showing the right-hand, intra-operative image of FIG. 52 superimposed and aligned with the left-hand, pre-operative image utilizing triangular stable bases.

In another construction, more than two points are generated for the stationary base for each image, such as illustrated in FIG. 52 for a preoperative image 1200 and a postoperative image 1201, and in FIG. 53 for a combined overlay image 1298 of the preoperative image 1200 and the postoperative image 1201 of FIG. 52. Similar locations on the pelvis in each image are selected to generate the points utilized to establish a stationary base for each image. In image 1200, for example, a first point 1202 is generated on an upper corner of the obturator foramen or at the pelvic tear drop, a second point 1204 is generated at the top or superior portion of the pubic symphysis, and a third point 1206 is generated at the lowest or inferior point on the ischial tuberosity. Lines 1208, 1210 and 1212 are drawn connecting those points to generate a visible stationary base triangle 1216 on image 1200. Also shown is a point 1214 on the greater trochanter. In postoperative image 1201, first and second points 1203 and 1205 correspond with first and second points 1202 and 1204 in image 1200. A third point 1207 is shown in image 1201 between reference squares 1209 and 1211 in the process of a user selecting the lowest point on the ischial tuberosity to correspond with third point 1206 in image 1200. The user is prompted by "Mark lowest point on Ischial Tuberosity" in the upper portion of image 1201. Also shown is a circle 1213 around the acetabular component and a point 1215 on the greater trochanter.

Establishing at least three points is especially useful for determining rotational differences between images. Overlay image 1298, FIG. 53, shows the three points 1202, 1204 and 1206 of preop image 1200, forming the visible preop stationary base triangle 1216, which is positioned relative to the corresponding three points 1203, 1205 and 1207 of postop image 1201, forming a visible postop stationary base triangle 1311 overlaid relative to triangle 1216 in FIG. 53. A 'best fit overlay' can be created using these points by identifying the centroid of the polygon created by these point, and rotating the set of point relative to one another to minimize the summation of distance between each of the related points. In this construction, scaling of the two images may be performed by these same set of points or, alternatively, a separate set of two or more points may be utilized to scale the two images relative to each other. Clicking on a PreOp soft-button icon 1300 and a PostOp icon 1301 enable a user to alter positioning of images 1200 and 1201, respectively, within image 1298 in a toggle-switch-type manner to selectively activate or de-activate manipulation of the selected feature. One or more points of a stationary base may be shared with points establishing a scaling line. Preferably, at least one landmark is selected that is spaced from the stationary base points to increase accuracy of overlaying and/or comparing images.

Also illustrated in FIG. 53 are "Offset and Leg Length Changes" with "Leg Length: −0.2 mm", "Offset: 21.8 mm" and "Confidence Score: 8.1". A confidence ratio that describes the quality of fit can be created by comparing the overlay area of the two triangles relative to the size of the overall polygon formed by the two triangles, including the non-overlapping areas of each triangle. Abduction angle and anteversion calculations are described below in relation to FIGS. 55-59.

Figure 17:
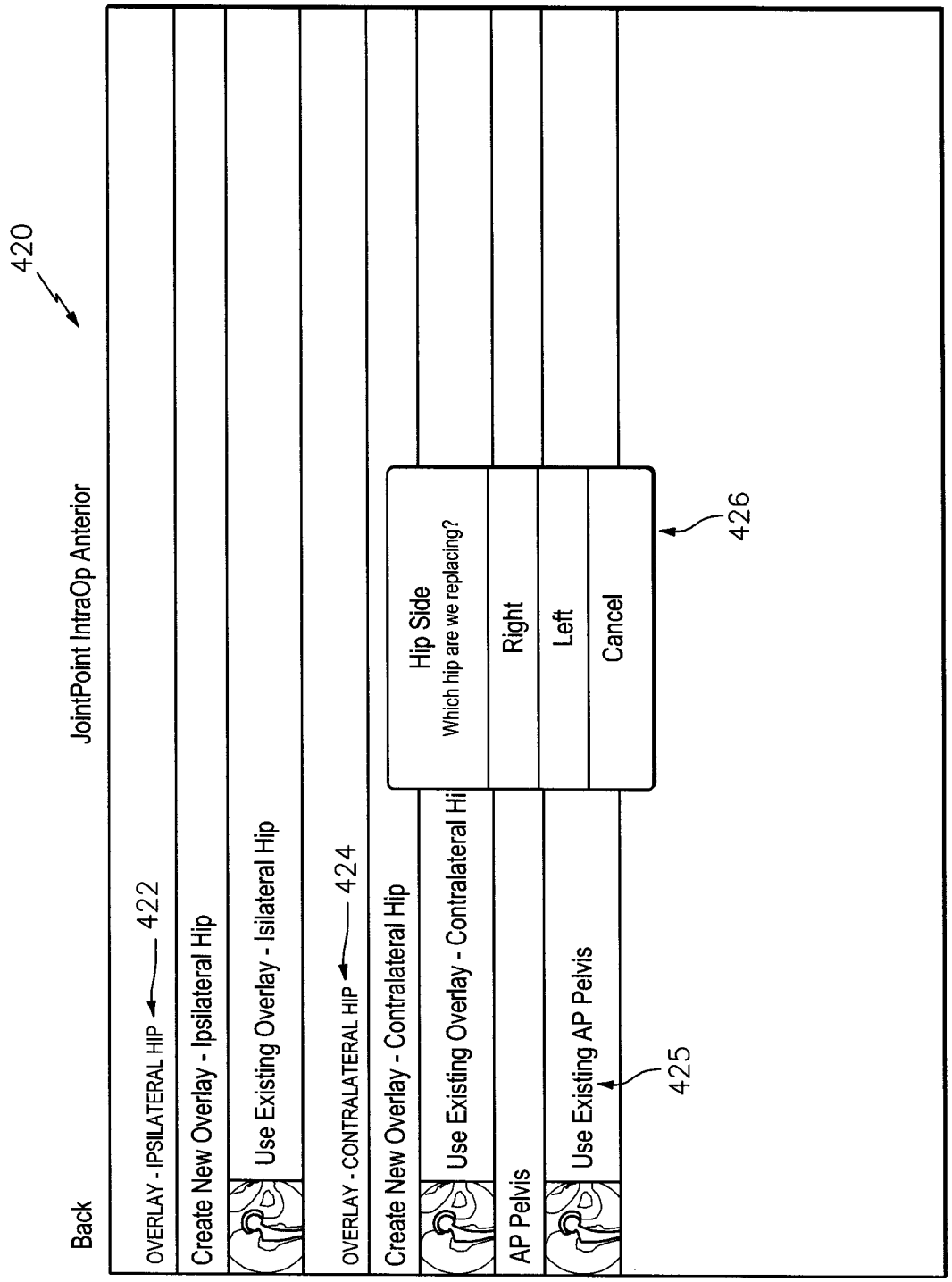
FIG. 17 represents a screen viewable by the user during a surgical procedure guided according to the present invention.

A screen 420 viewable by a user during a surgical procedure guided by a JointPoint™ IntraOp Anterior™ system according to the present invention is represented by FIG. 17. The user selects OVERLAY-IPSILATERAL HIP 422 or OVERLAY-CONTRALATERAL HIP 424 with the option to use an existing overlay. The operative hip side to be "replaced" is selected, via window 426, to confirm which will be the operative side and the comparative side; the comparative side is the same side as the operative side when a prior ipsilateral image is chosen. Another option for the user is to select AP (Anterior-Posterior) Pelvis simulation, step 425; in another construction, AP Pelvis is presented to a user at a later stage within Contralateral Hip overlay creation.

Figure 18:
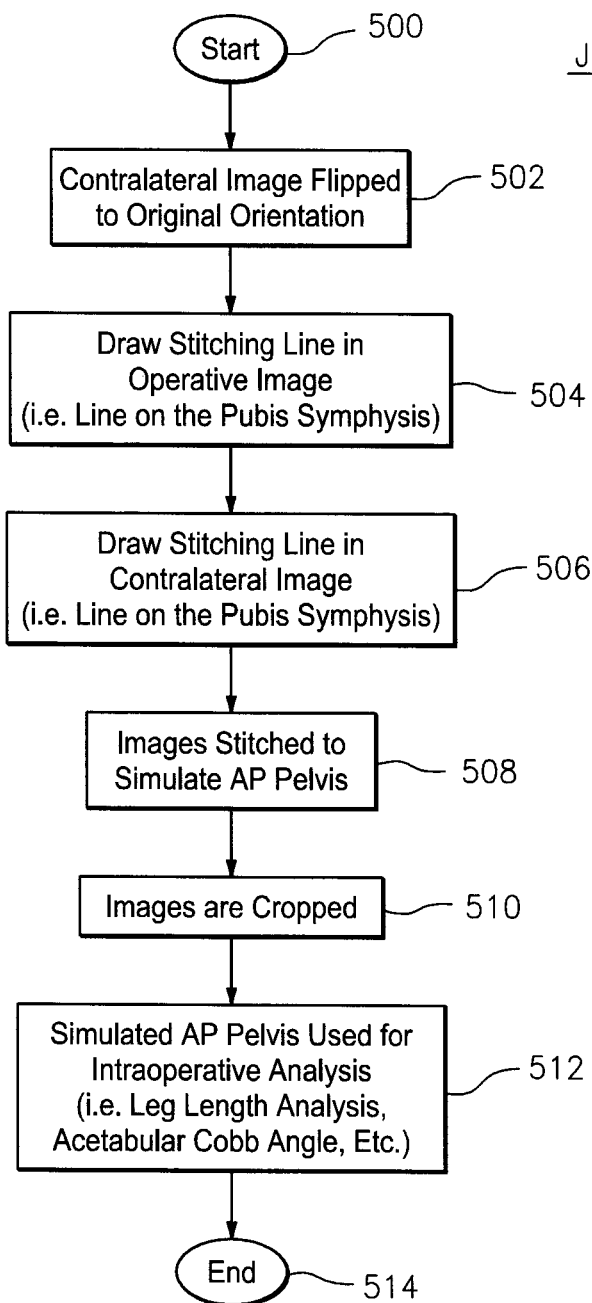
FIG. 18 is Flowchart J of AP Pelvis Stitching and Analysis.
Figure 19:
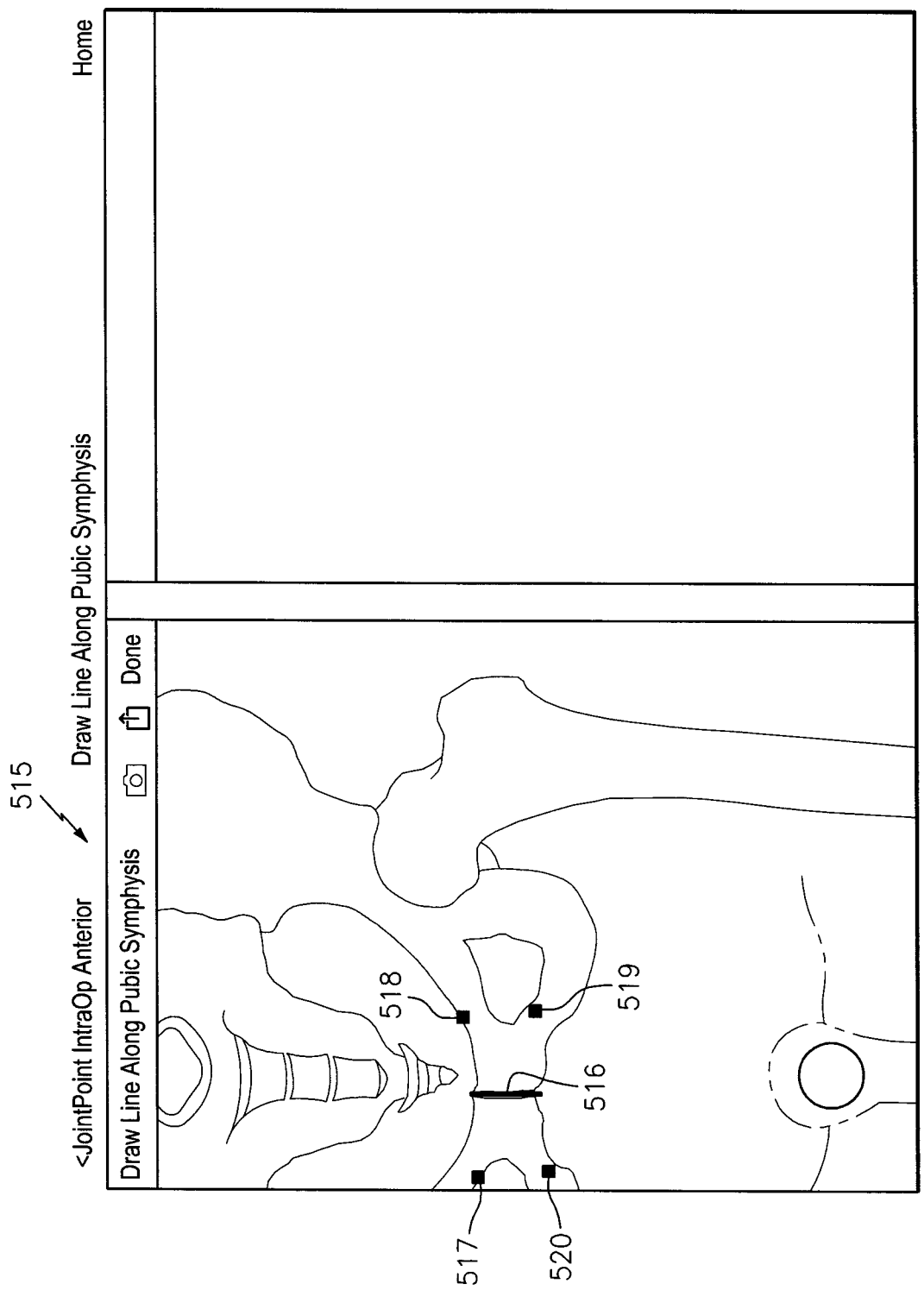
FIG. 19 represents a screen view with a left-hand image of the contra-lateral, left side of a patient having a line drawn on the pubic symphysis.
Figure 20:
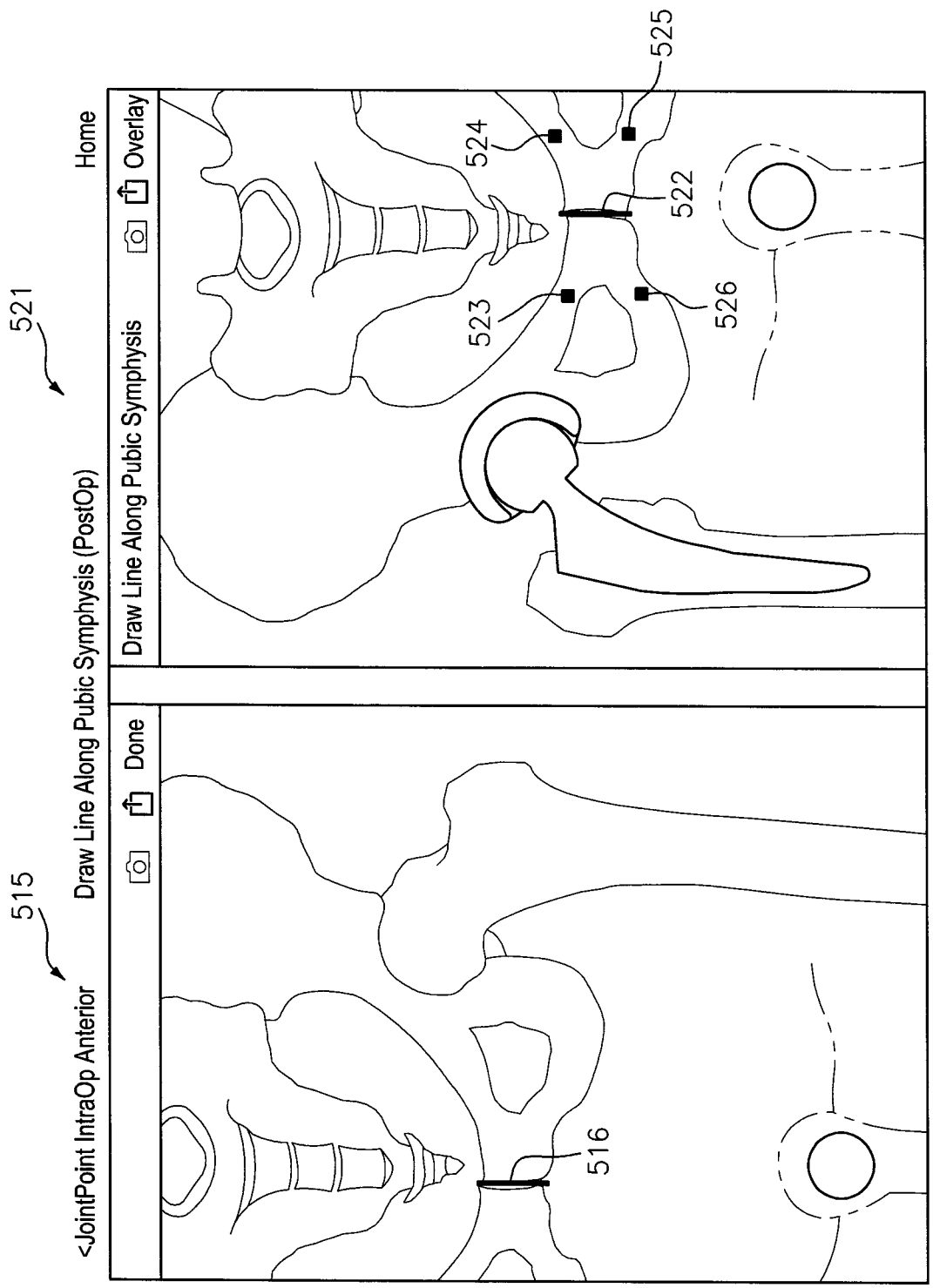
FIG. 20 is a view similar to FIG. 19 plus a right-hand, intra-operative image of the right side of the patient, also having a line drawn on the pubic symphysis.
Figure 21:
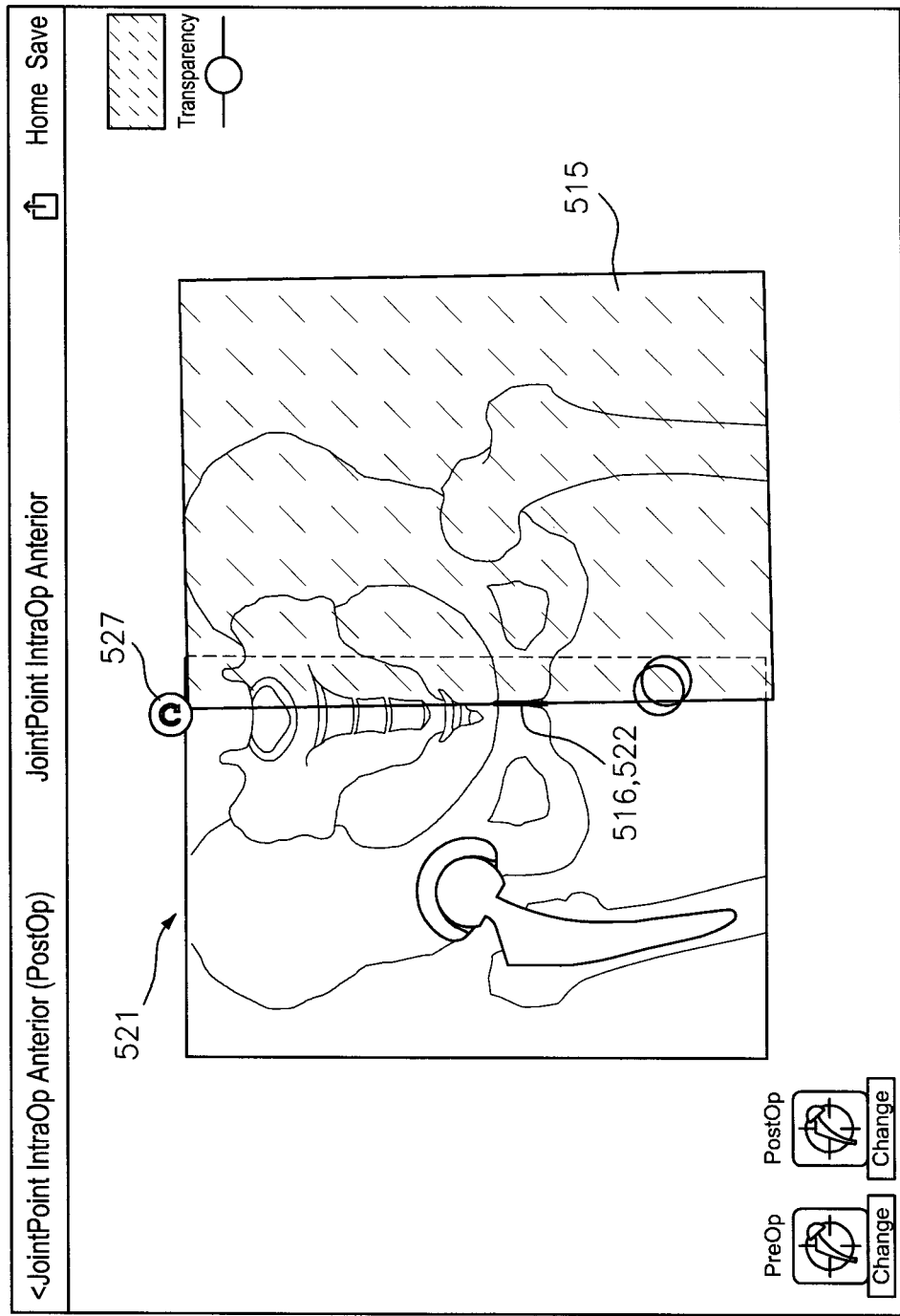
FIG. 21 shows the images of FIG. 20 overlaid and "stitched together" to reconstruct a view of the entire hip region of the patient

Flowchart J, FIG. 18, presents one technique according to the present invention for AP Pelvis Stitching and Analysis. The technique is commenced, step 500, and a contralateral image is flipped to its original orientation, step 502. A stitching line is drawn in the operative image, step 504, such as a line 516 on the pubic symphysis shown in FIG. 19 for image 515, guided by reference squares 517, 518, 519 and 520. A similar line is drawn on the contralateral image, step 506, such as shown by line 522 in FIG. 20 for image 521, guided by reference squares 523, 524, 525 and 526. The images are stitched, step 508, to simulate an AP Pelvis image as shown in FIG. 21 with overlapped stitching lines 516 and 522, with optional user adjustment by touching movement control icon 527, also referred to as a "rotation handle". The images are cropped, step 510, and the simulated AP Pelvis is utilized for intraoperative analysis, step 512, such as leg length analysis or acetabular cobb angle. The technique terminates, step 514, and returns to step 334, FIG. 6, in one construction.

Figure 22:
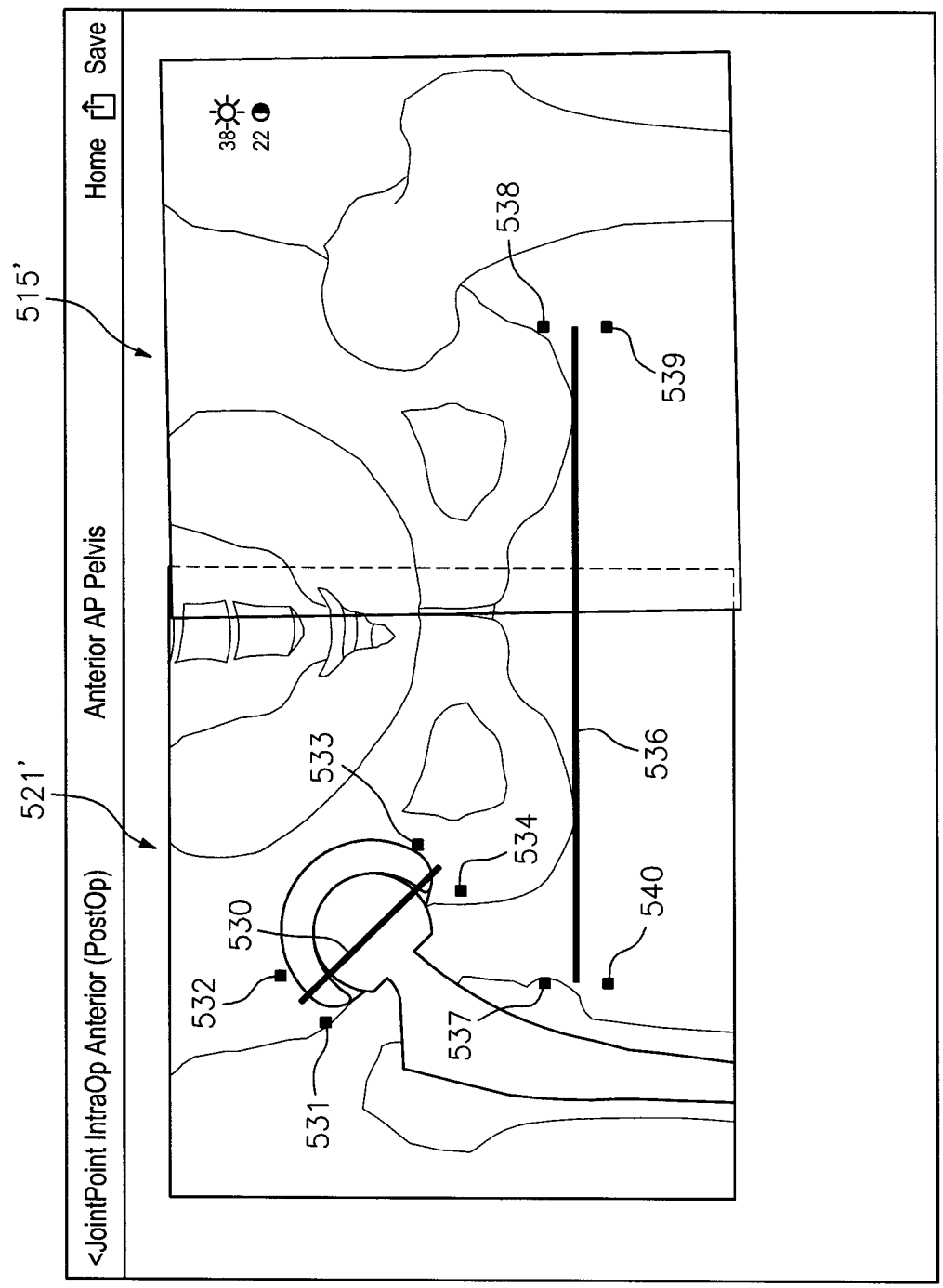
FIG. 22 is view similar to FIG. 21 with one reference line drawn across the acetabular component of the image and another reference line touching the lower portions of the pelvis

FIG. 22 is view similar to FIG. 21 with one reference line 530 drawn across the acetabular component of the image 521', as guided by reference squares 531, 532, 533 and 534, and another reference line 536, as guided by reference squares 537, 538, 539 and 540, touching the lower portions of the pelvis to enable accurate stitching for intraoperative analysis, including acetabular component cobb angle determination, according to the present invention. Additional analysis of the acetabular component, such as anteversion or other alterations of position, orientation or size, can be utilized as well.

Figure 23:
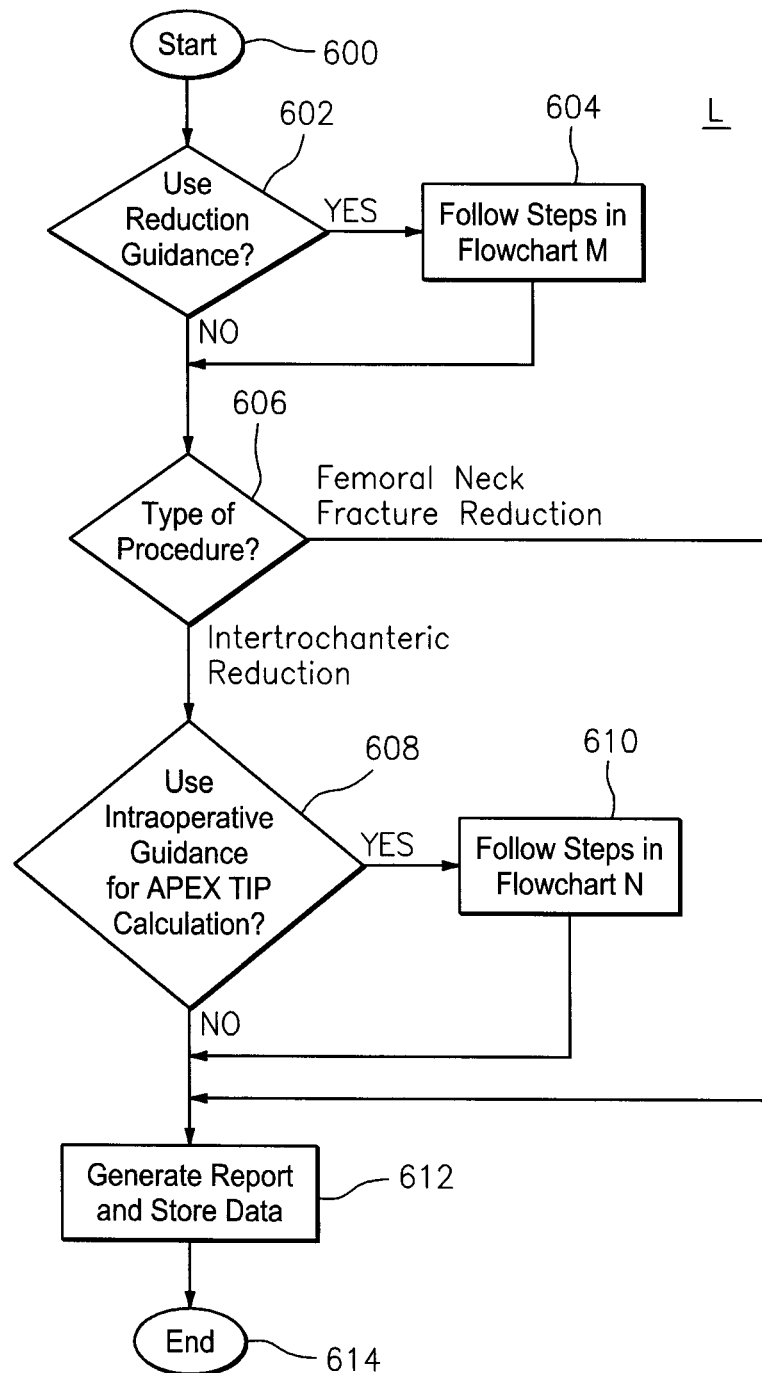
FIG. 23 is Flowchart L showing Intraoperative Guidance for Intertrochanteric Reduction and Femoral Neck Fractures according to another aspect of the present invention, referencing Flowcharts M and N.

Flowchart L, FIG. 23, illustrates Intraoperative Guidance for Intertrochanteric Reduction and Femoral Neck Fractures according to another aspect of the present invention, referencing Flowcharts M and N. The technique begins, step 600, and reduction guidance is considered, step 602. If selected, then the procedure outlined in Flowchart M is initiated, step 604. Otherwise, or after the Flowchart M procedure has been completed, the technique proceeds to step 606 where the type of surgical procedure is selected. In this construction, for Femoral Neck Fracture Reduction, the technique proceeds to step 612 to generate a report and store data for future reference. If Intertrochanteric Reduction is selected, then guidance for Apex-Tip calculation is considered. If selected, then the procedure described by Flowchart N is followed, step 610. Otherwise, or after the Flowchart N procedure has been completed, the technique proceeds to step 612 where a report is generated and data stored as mentioned above. Guidance for those procedures then ends, step 614.

Figure 24:
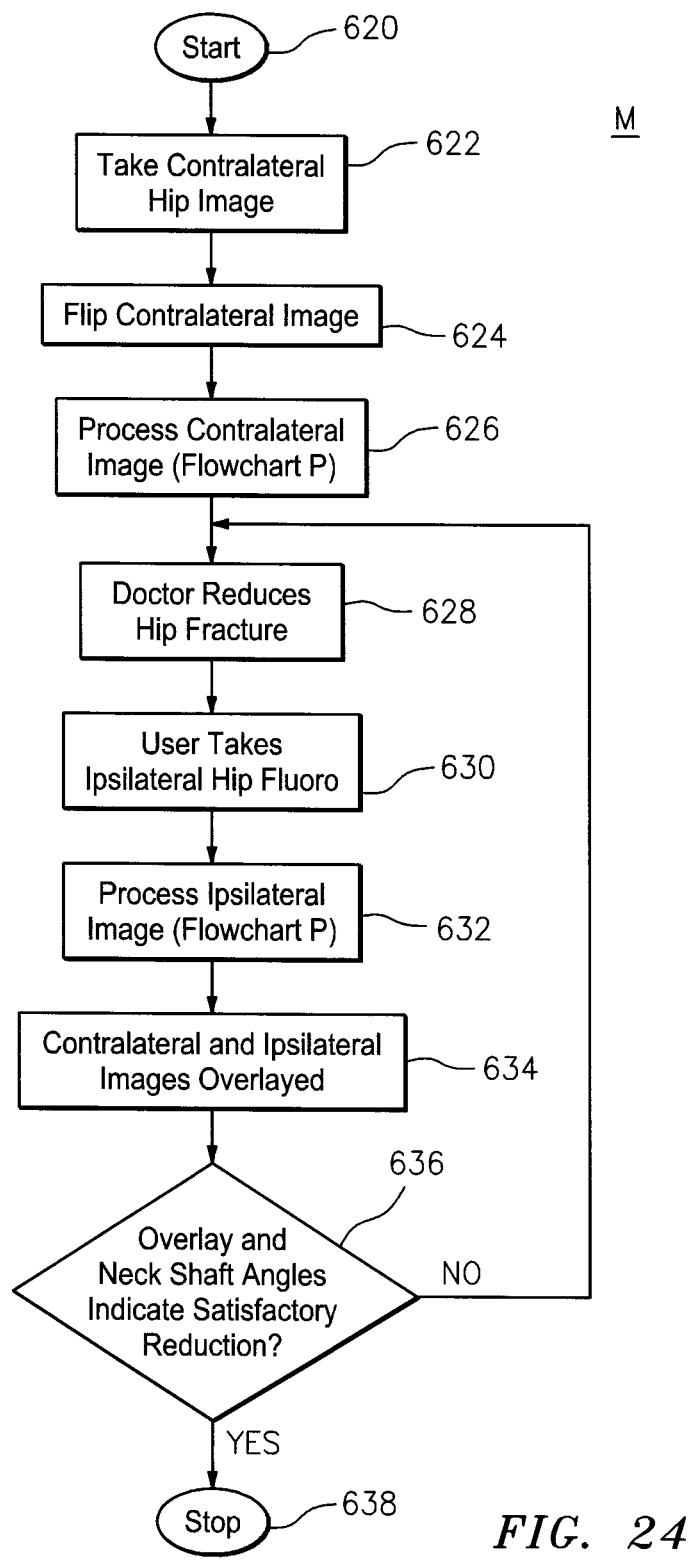
FIG. 24 is Flowchart M for Intertrochanteric Reduction Guidance, referencing Flowchart P.
Figure 26:
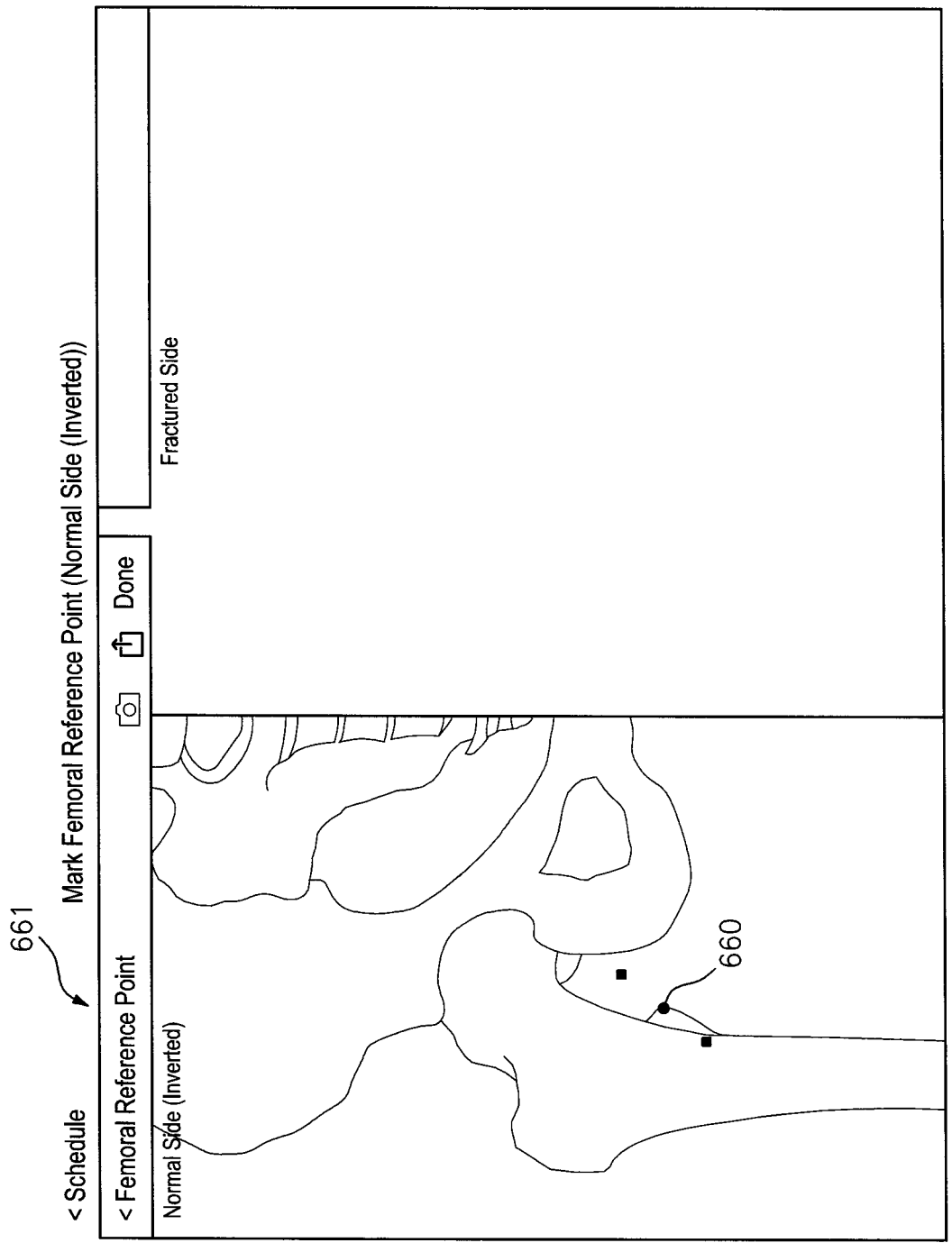
FIG. 26 is a representation of a screen view with a left-hand image of the left, contralateral, "normal" side of a patient's hip region inverted to resemble the right, "fractured" side of the patient and showing marking of the lesser trochanter to serve as a femoral reference point.
Figure 32:
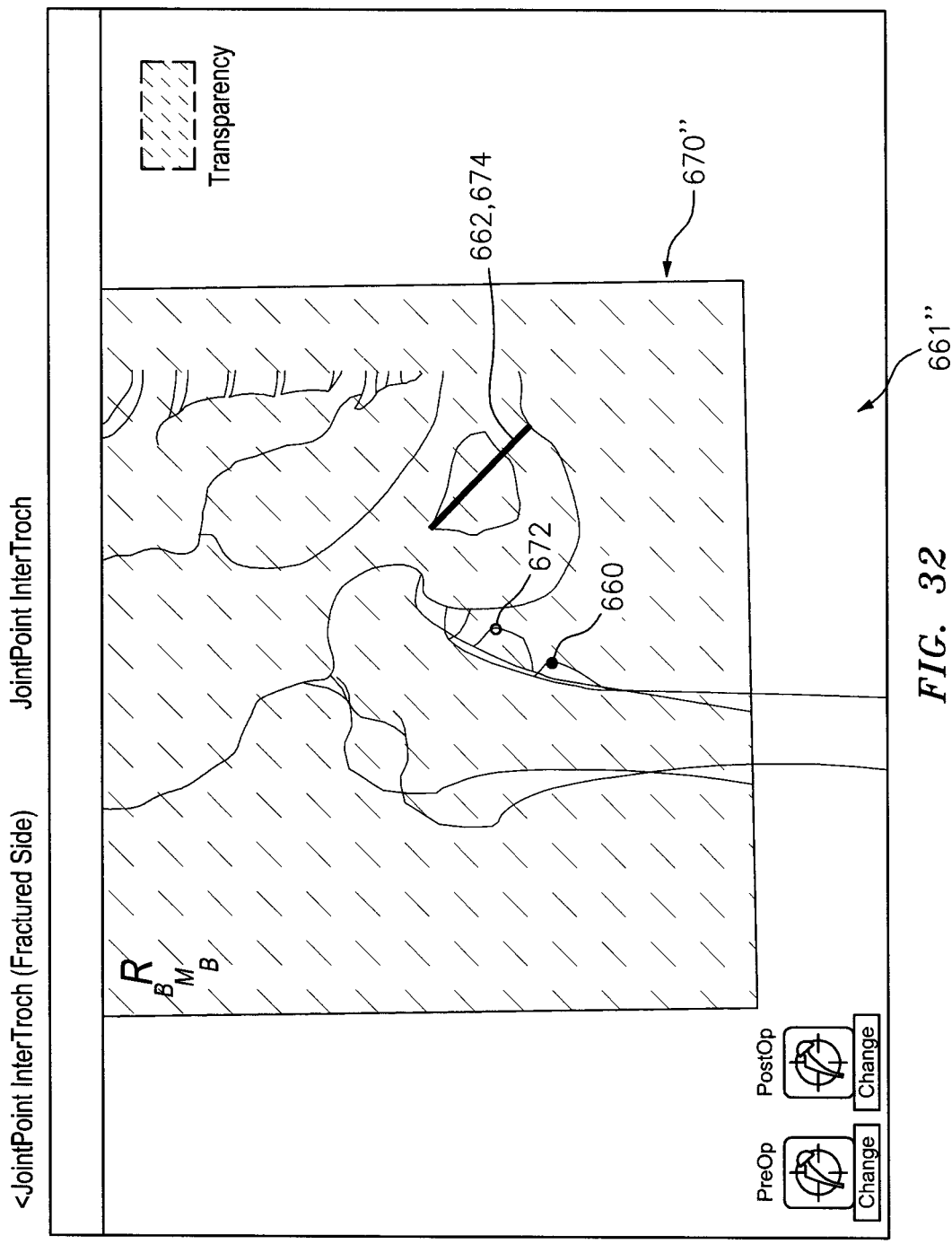
FIG. 32 is a combined image showing the fractured side image overlaid on the normal, inverted side image.

Flowchart M, FIG. 24, for Intertrochanteric Reduction Guidance, commences at step 620 when selected and the technique proceeds to step 622 where a contralateral hip image is taken and then flipped, step 624, to achieve a screen view such as illustrated in FIG. 26. The inverted contralateral image is then processed as outlined in Flowchart P as described below. The surgeon then reduces the hip fracture, step 628, and the user of this Guidance takes an X-ray-type image of the operative hip, indicated in step 630 as "User takes ipsilateral hip fluoro". That image is then processed by the procedure of Flowchart P, step 632, and the contralateral and ipsilateral images are overlaid, step 634, such as shown in FIG. 32.

The overlay and neck shaft angles are analyzed in step 636, FIG. 24 and, if not acceptable, the procedure returns to step 628 for another round of fracture reduction and analysis. Once acceptable, the procedure of Flowchart M is ended, step 638, and the technique returns to step 606, FIG. 23 as discussed above.

Figure 25:
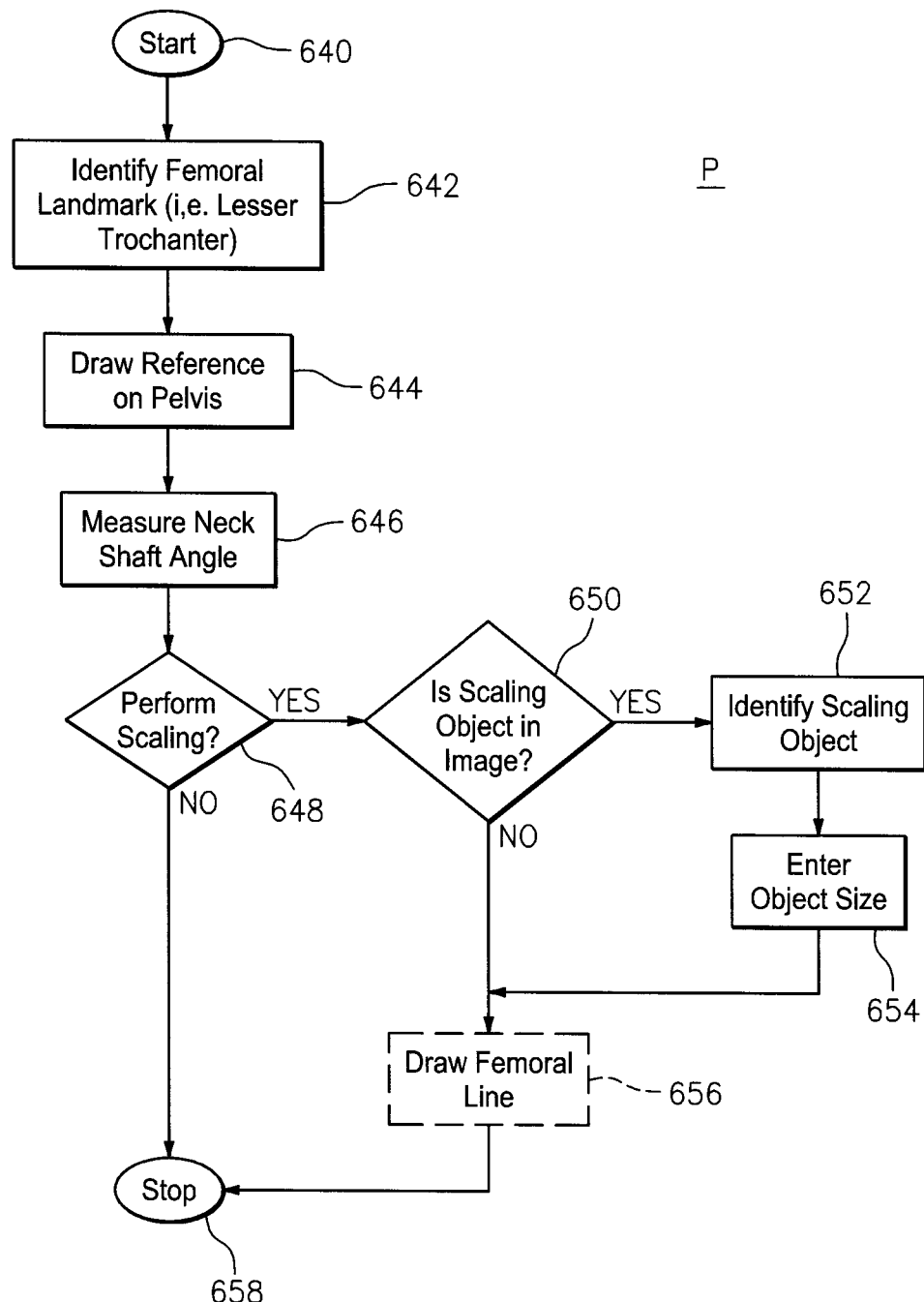
FIG. 25 is Flowchart P for processing a Contralateral or Ipsilateral Image.
Figure 27:
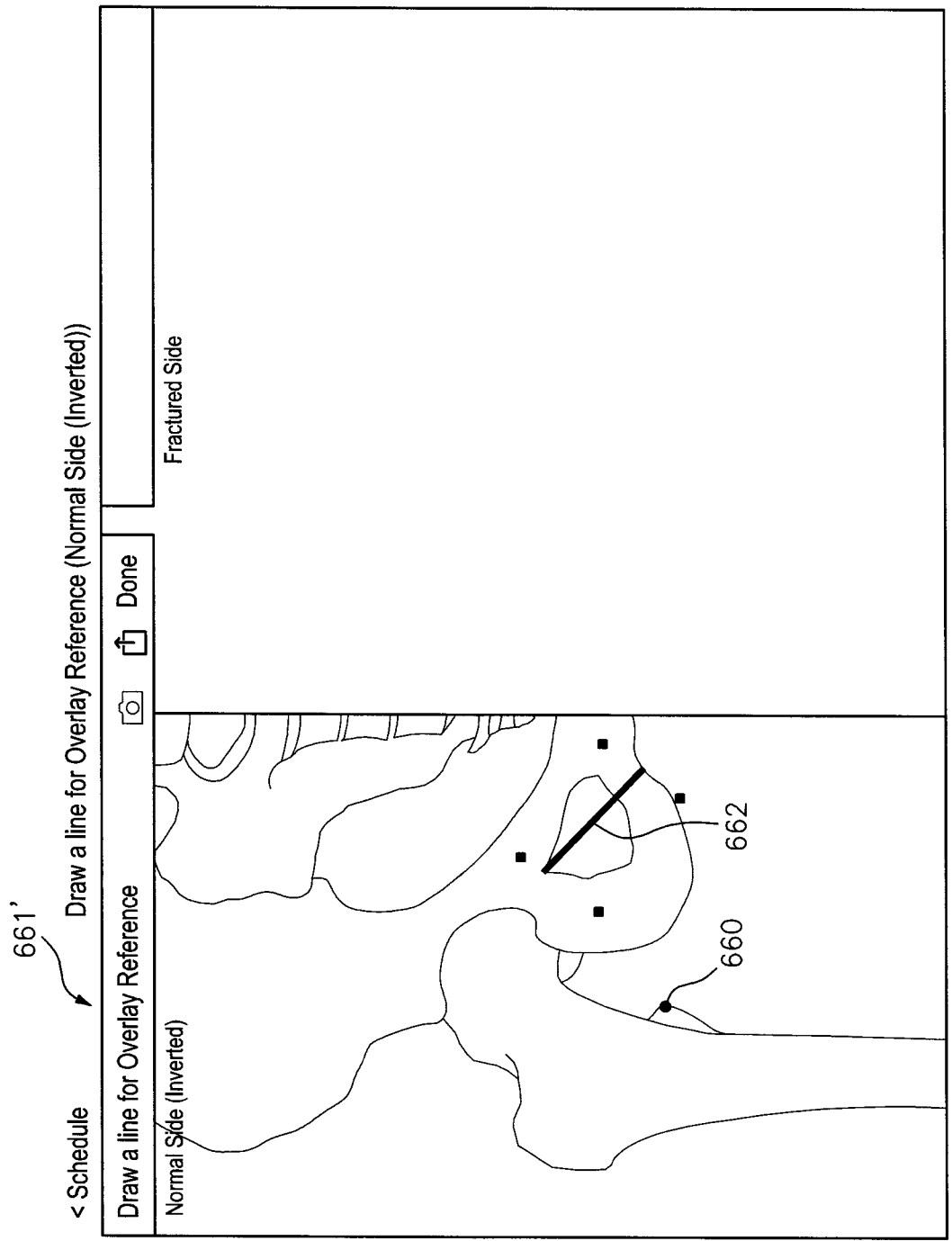
FIG. 27 is a view similar to FIG. 26 showing drawing of a line across the obturator foramen for overlay reference.
Figure 28:
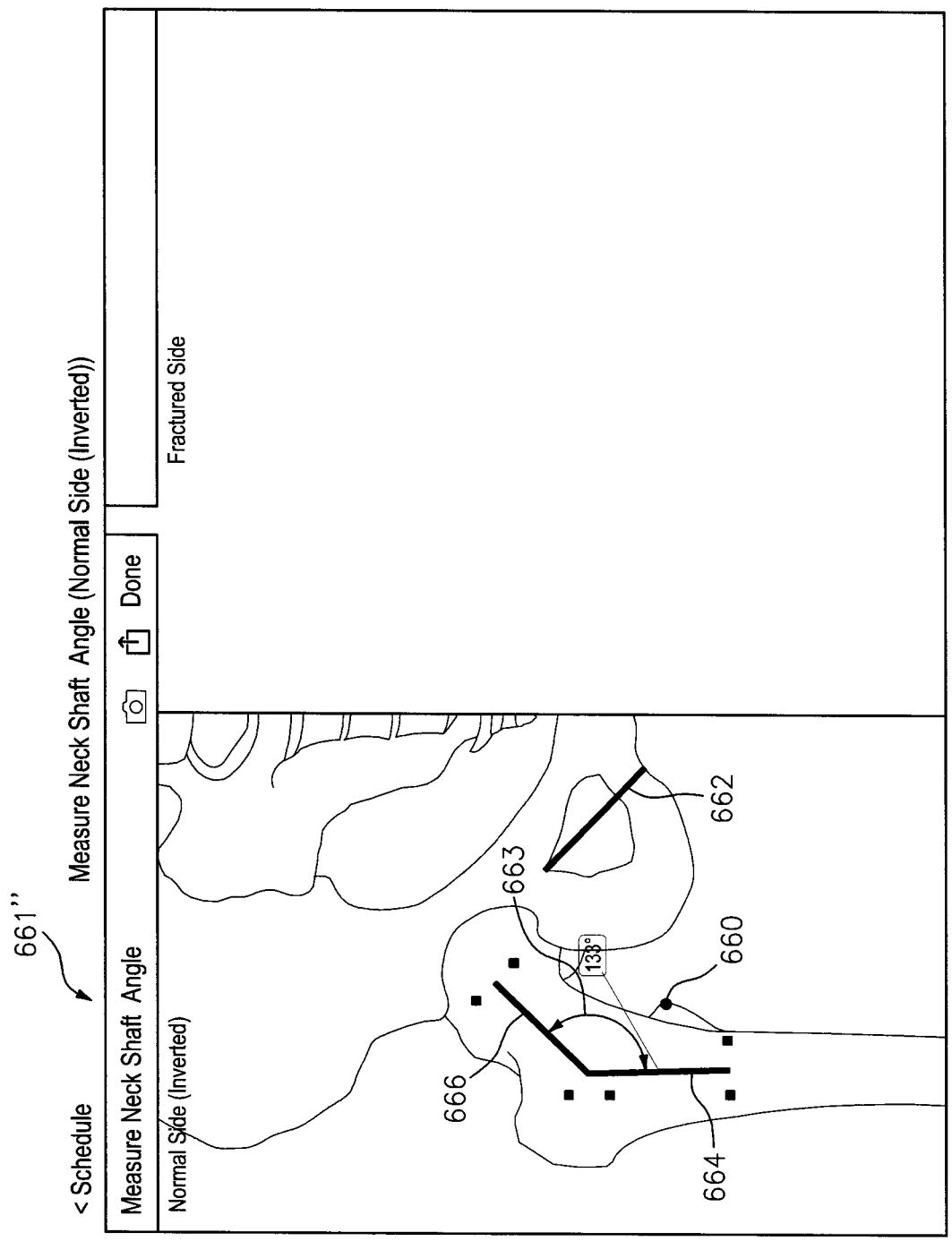
FIG. 28 is a view similar to FIG. 27 showing measurement of neck shaft angle.

Flowchart P, FIG. 25, for processing a Contralateral or Ipsilateral Image, begins at step 640 and then at least one femoral landmark is identified, step 642, such as marking the lesser trochanter with mark 660 as shown in FIG. 26 for an inverted image 661 of the normal, un-injured contralateral side of the patient. A stationary base reference, preferably established by at least two points, such as for line 662, is drawn on the pelvis, step 644, FIG. 25, as shown in FIG. 27 for image 661'. The neck shaft angle 663 is measured, step 646, as shown in FIG. 28 as 138 degrees for image 661". Typically, this step 646, FIG. 25, includes identifying the longitudinal axis 664 of the femur, FIG. 28, because the femoral line 664 serves as one "leg" of the angle 663 to be measured, with the other leg 666 established by the longitudinal axis of the femoral head. In some constructions, the femoral line 664 provides an important reference relative to the stationary base 662 so that the present system and method can compensate for any difference in leg positions between images. It is not unusual for a leg to shift its orientation by 5 degrees to 15 degrees even when the leg is held in traction.

If scaling is desired, step 648, FIG. 25, then it is considered whether a scaling object is present in the image, step 650. If yes, then the scaling object is identified, step 652, and the object size is entered, step 654. After those steps 652-654 are completed, or if no scaling object is found in step 650, the technique proceeds to the optional step of drawing a femoral line, step 656 shown in phantom, if additional analysis is desired beyond measuring the neck shaft angle in step 646 as described above. In any event, after the procedure of Flowchart P is completed, step 658, the technique returns to step 628 or step 634, FIG. 24, in this construction.

Figure 29:
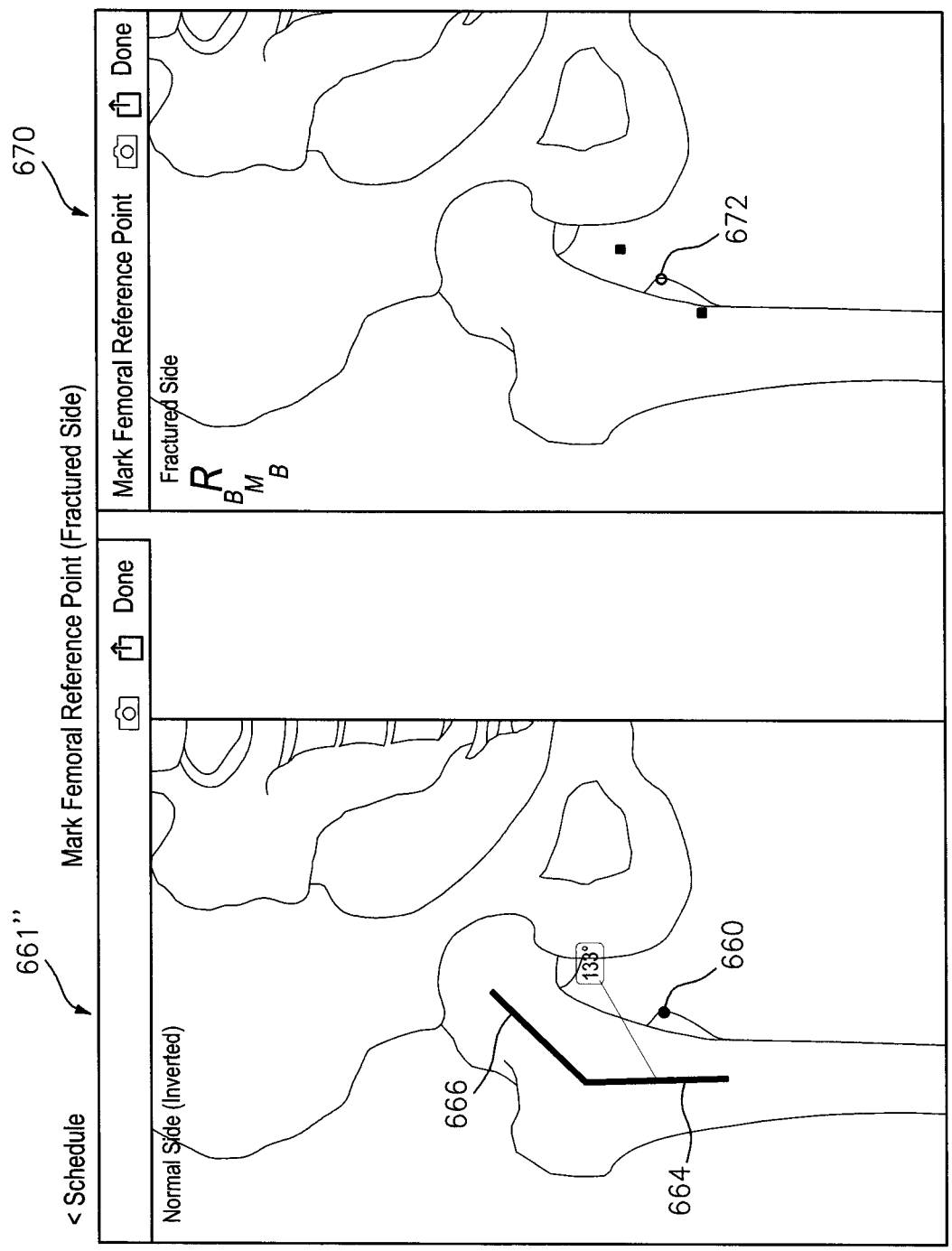
FIG. 29 is a screen view with the left-hand image similar to FIG. 28 and a right-hand image of the fractured side of the patient, showing marking of the lesser trochanter on the fractured side.
Figure 30:
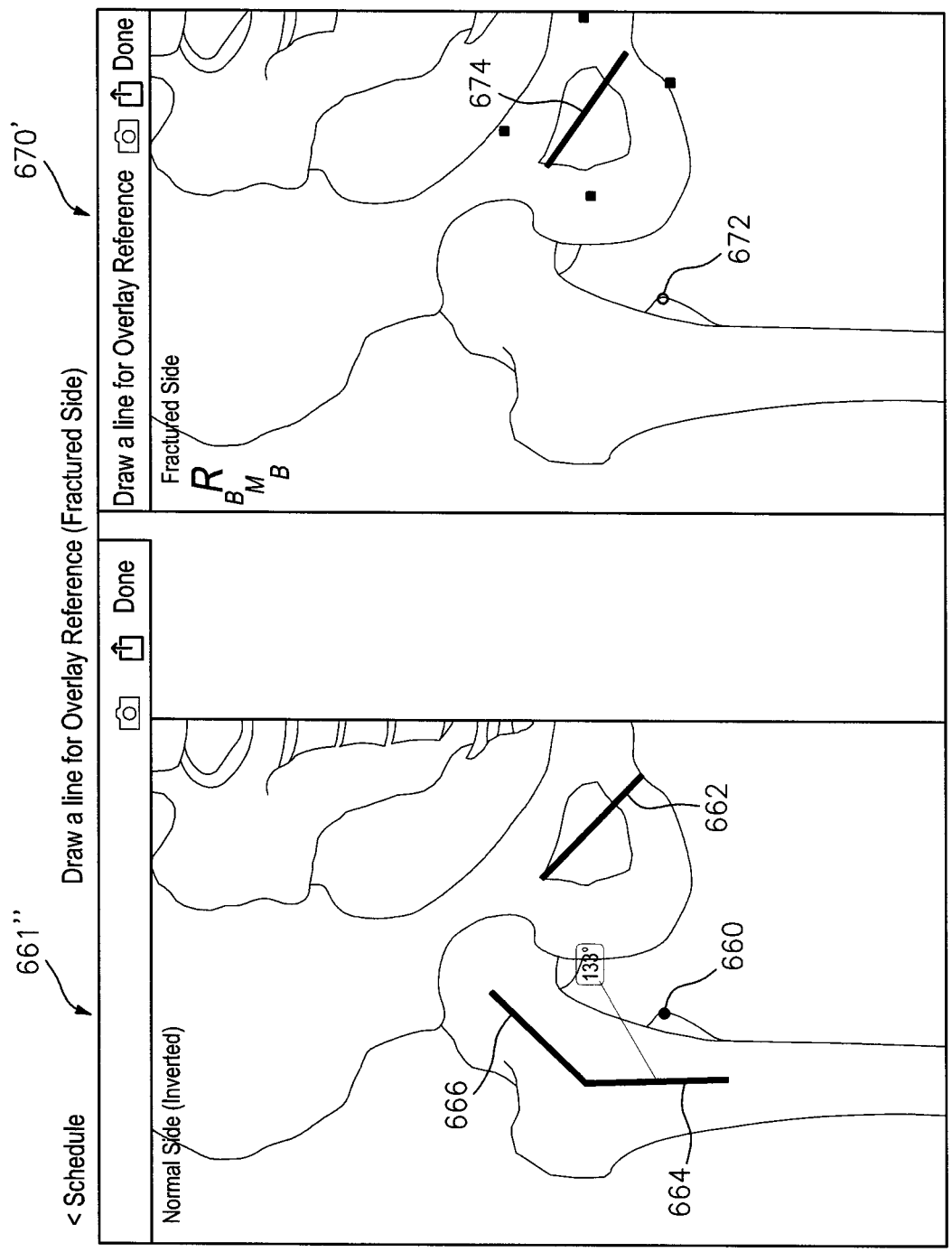
FIG. 30 is a view similar to FIG. 29 showing marking of the obturator foramen of the fractured side.
Figure 31:
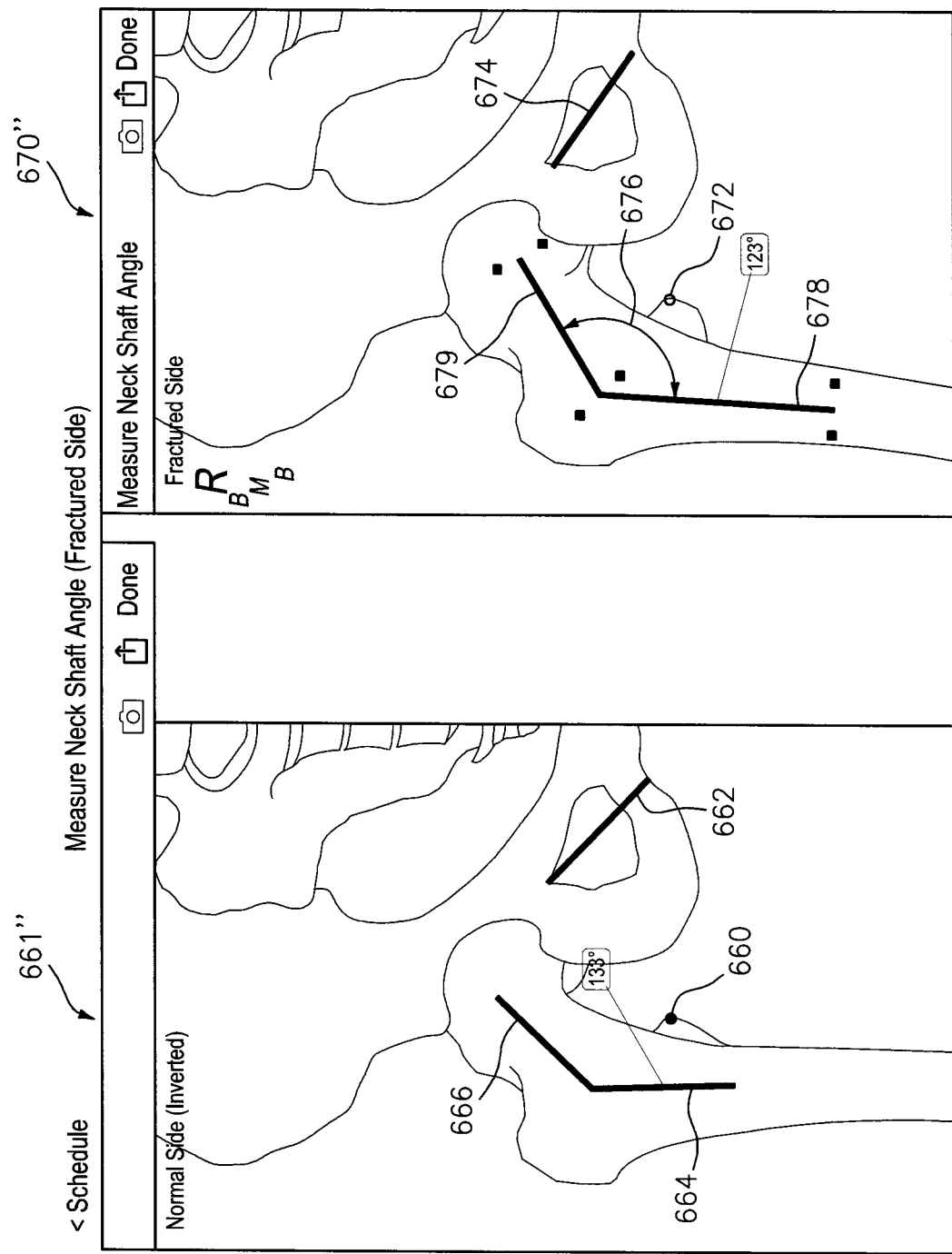
FIG. 31 is a view similar to FIG. 30 showing measurement of neck shaft angle on the fractured side.

FIG. 29 is a screen view with the left-hand image 661" similar to FIG. 28 and a right-hand image 670 of the fractured side of the patient, showing marking of the lesser trochanter on the fractured side with a mark 672. FIG. 30 is a view similar to FIG. 29 showing marking of the obturator foramen of the fractured side with stable base line 674 in image 670'. FIG. 31 is a view similar to FIG. 30 showing measurement of neck shaft angle of 123 degrees on the fractured side as determined by measuring angle 676 between femoral axis 678 and femoral head axis 679. FIG. 32 is a combined image showing the fractured side image 670" overlaid on the normal, inverted side image 661". Stable base lines 662 and 674 are overlapped exactly in this construction.

Figure 33:
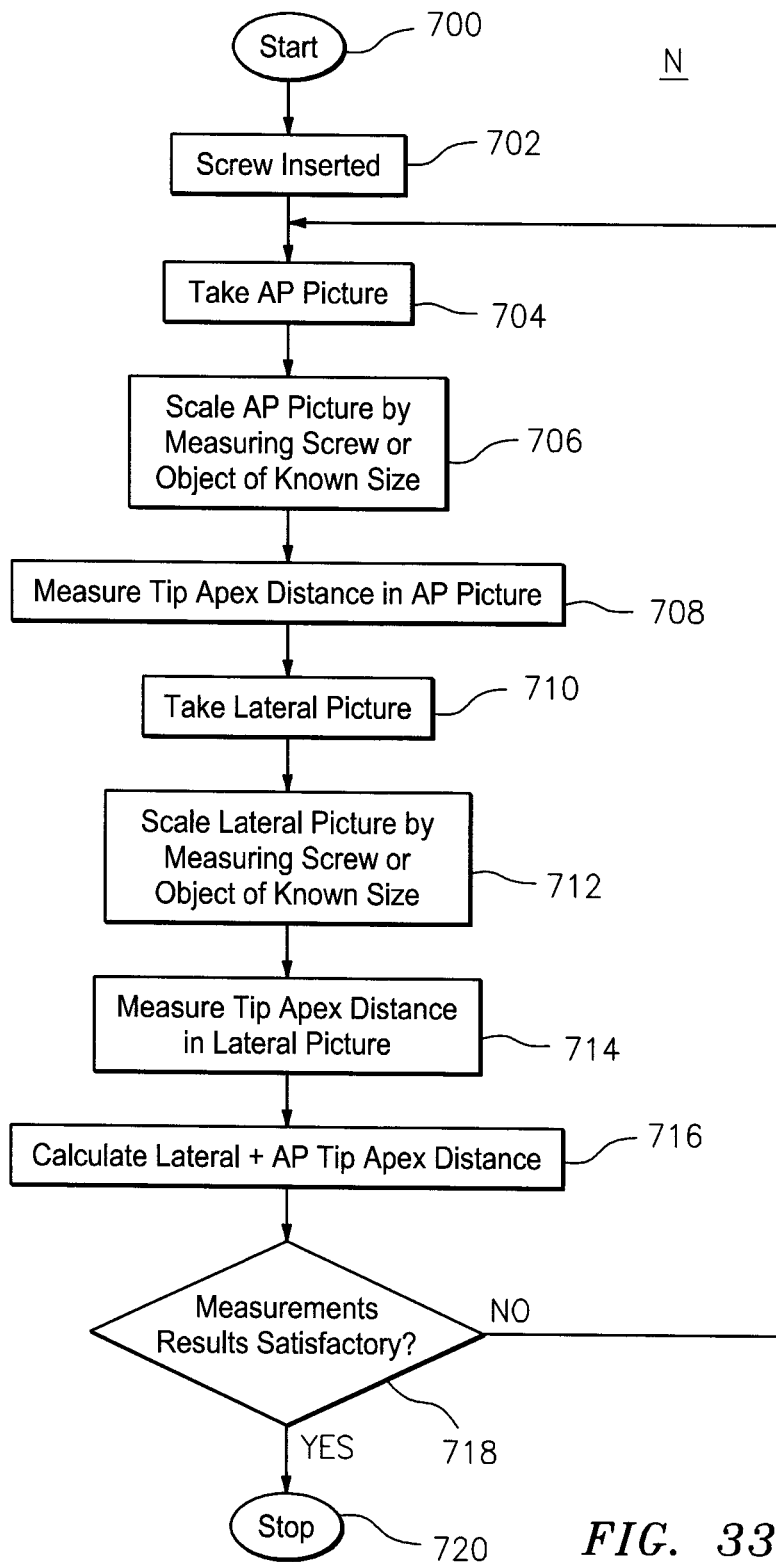
FIG. 33 is Flowchart N showing scaling and measurement as referenced in Flowchart L.
Figure 34:
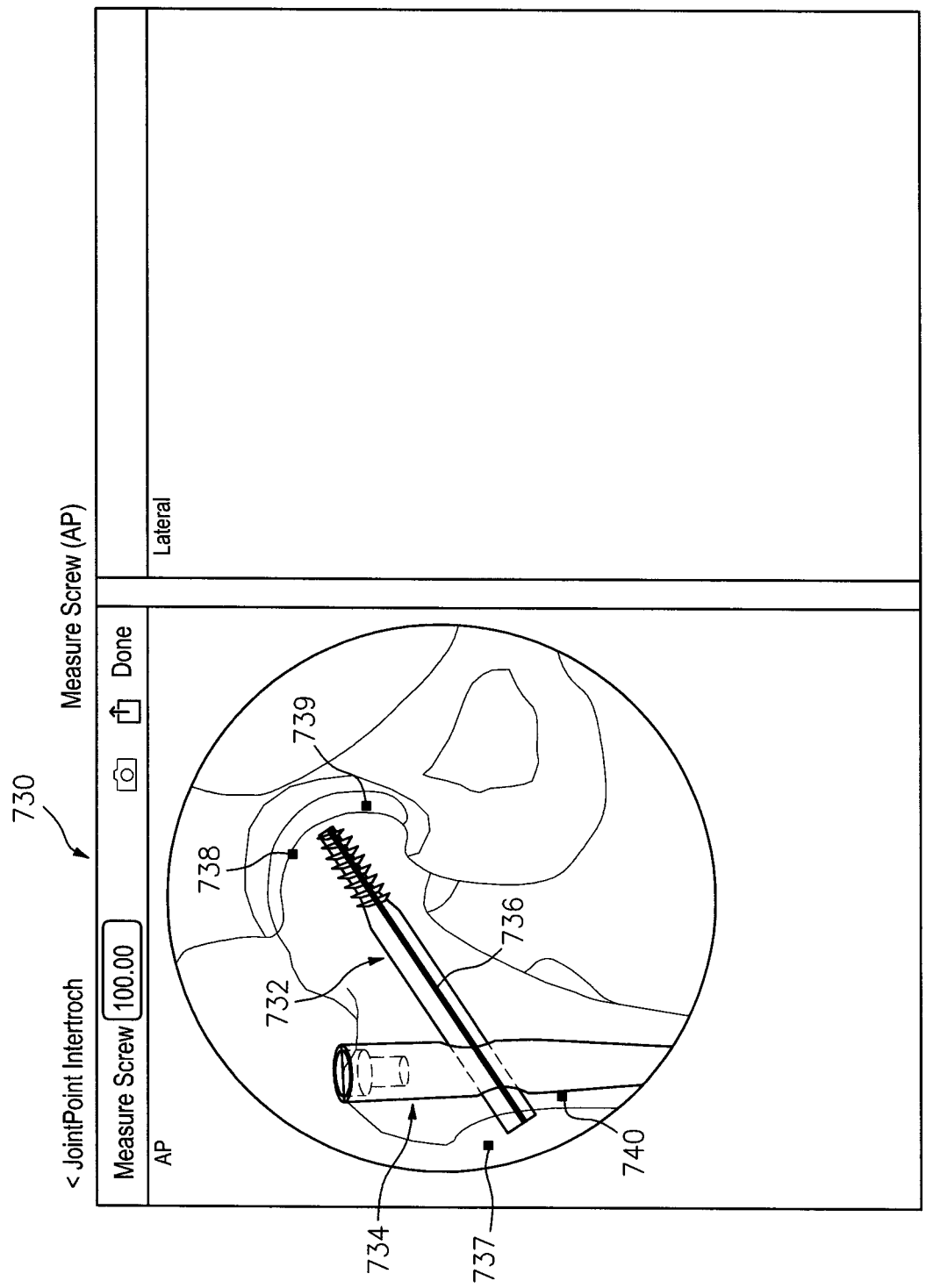
FIG. 34 represents a screen view of an image of a screw implanted to treat an inter-trochanteric hip fracture, showing measurement of the screw.
Figure 35:
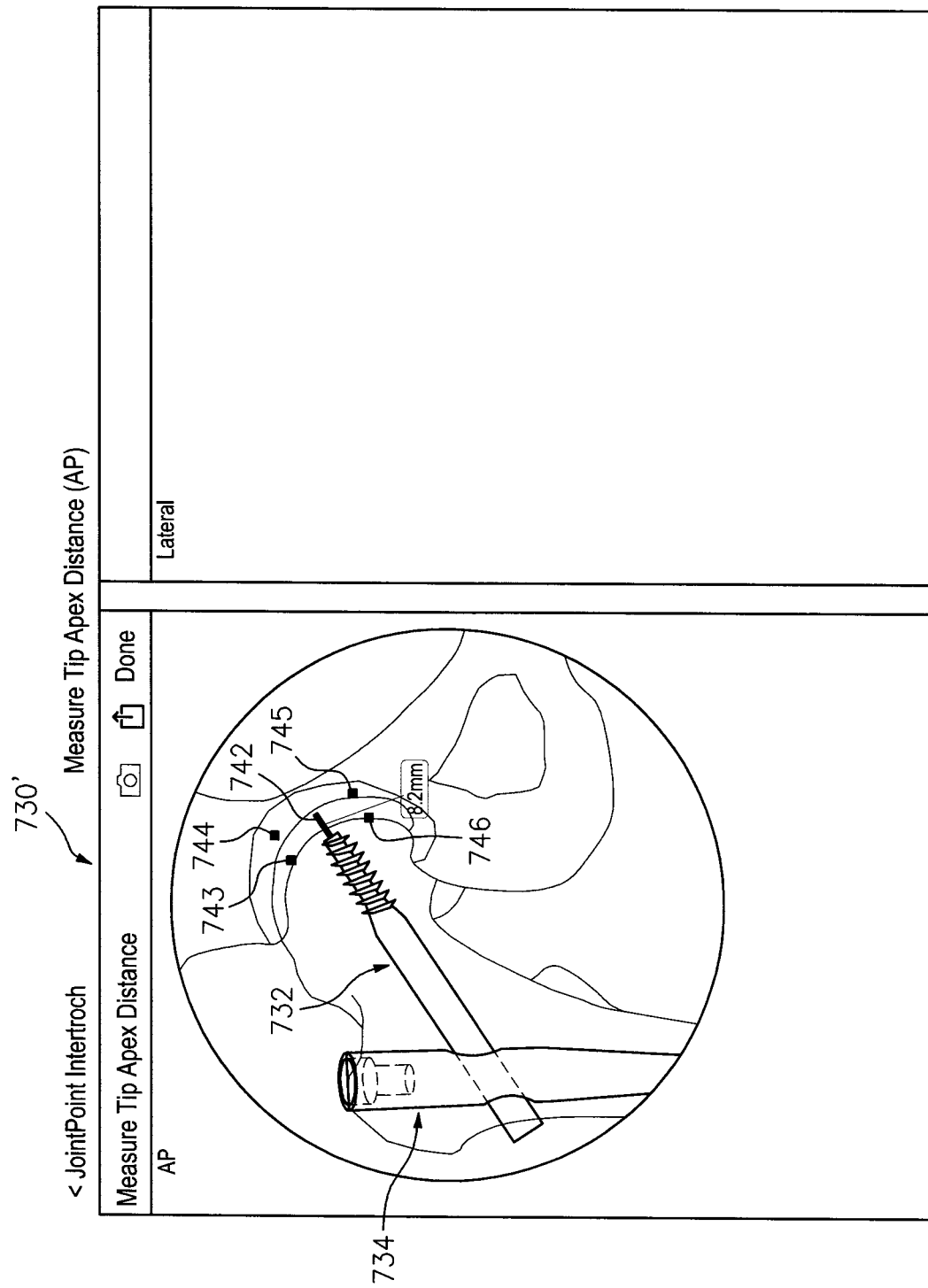
FIG. 35 is a view similar to FIG. 34 showing measurement of Tip-Apex distance in an AP image.
Figure 36:
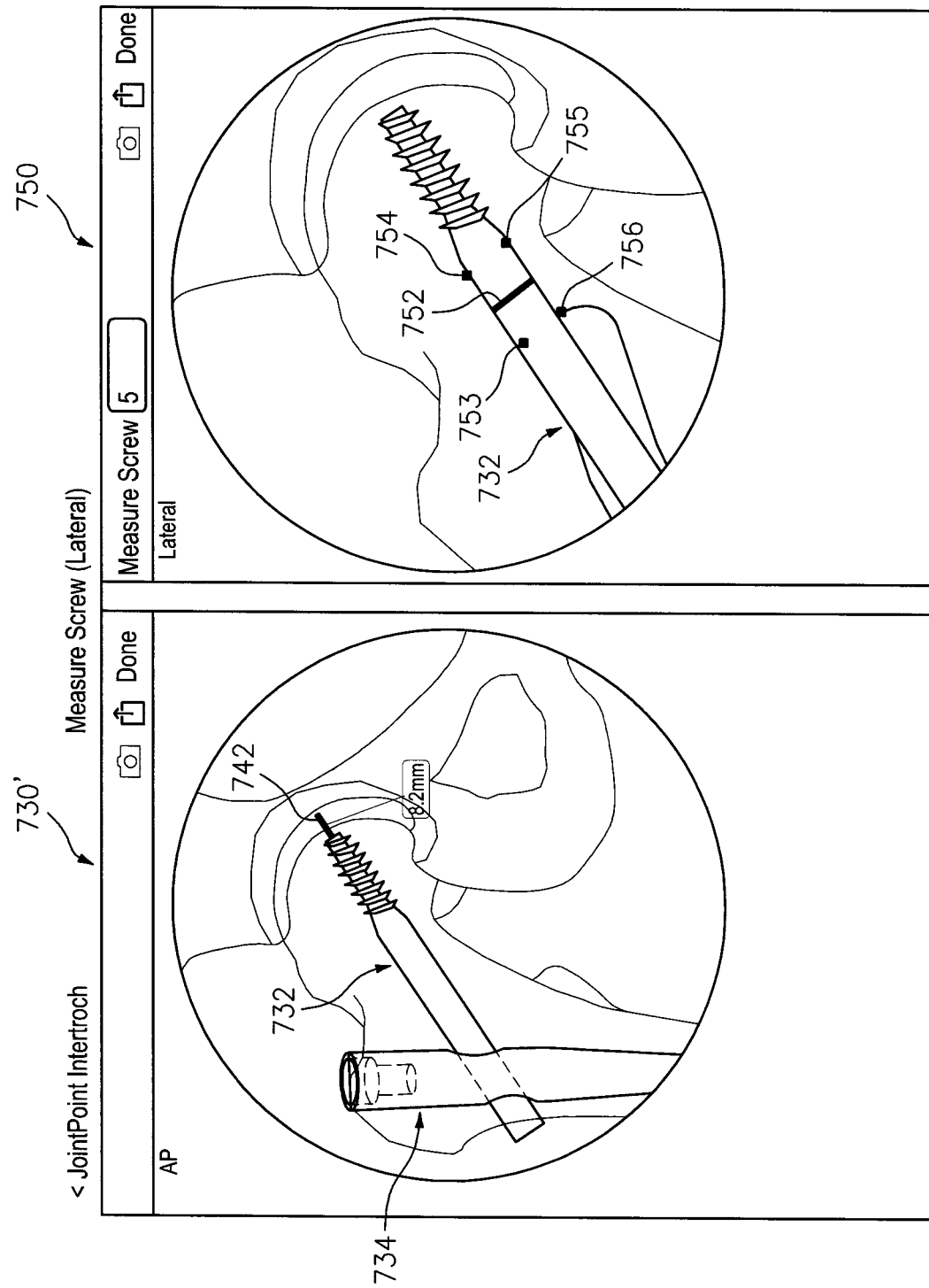
FIG. 36 is a view similar to FIG. 35 plus a lateral view on the right-hand side of the screen, showing measurement of the screw.
Figure 37:
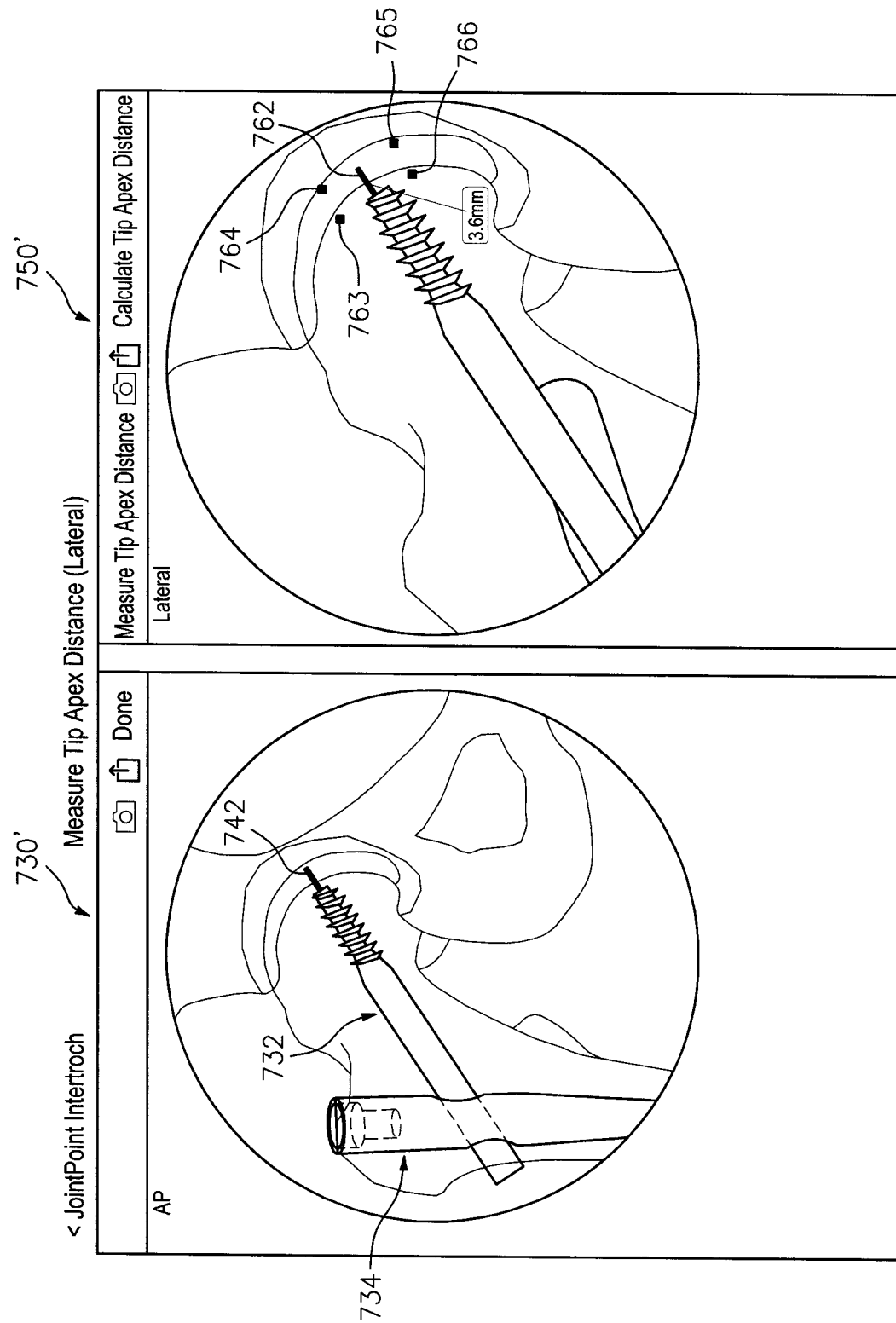
FIG. 37 is a view similar to FIG. 36 showing measurement of Tip-Apex distance in the right-hand image.
Figure 38:
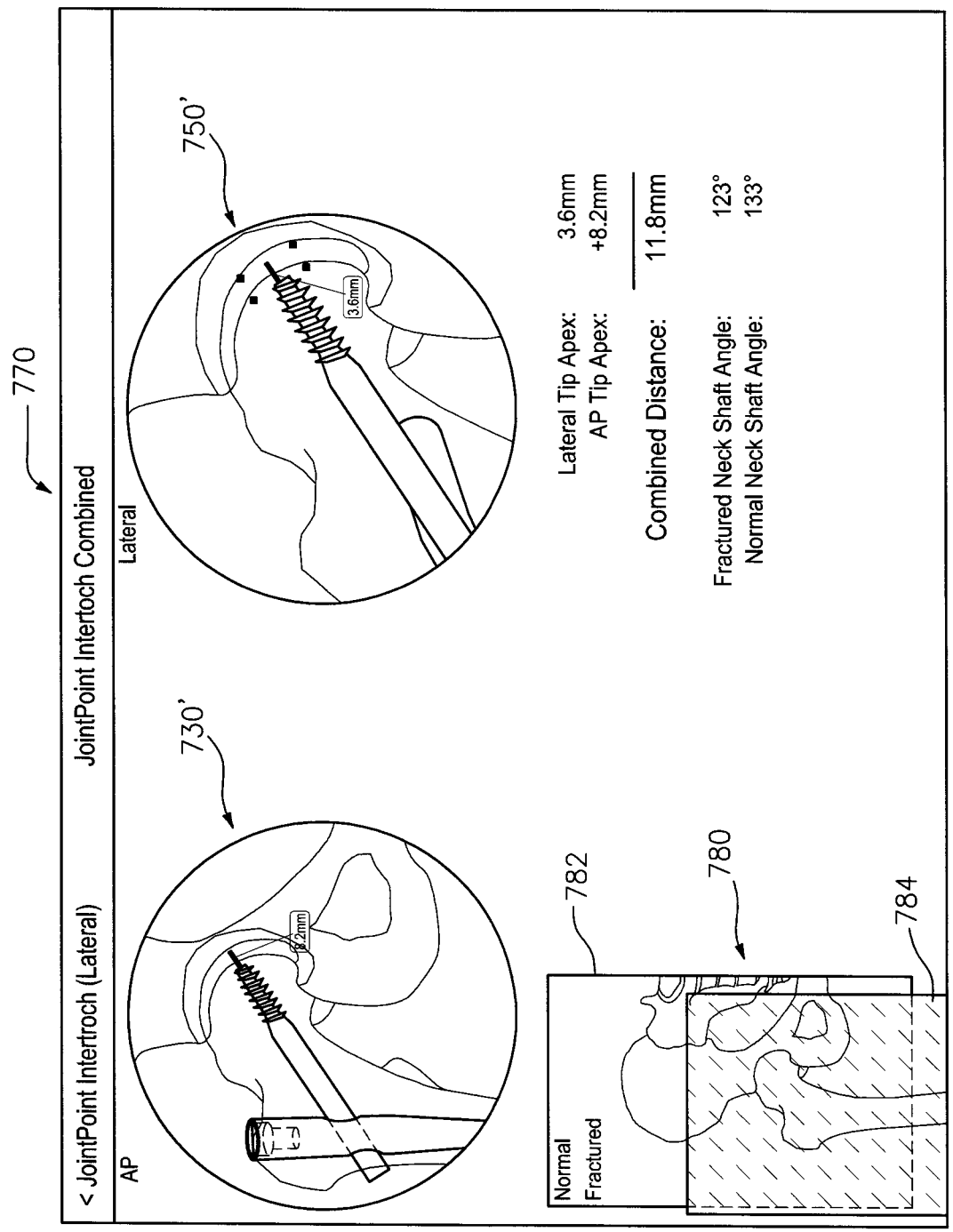
FIG. 38 is a combined "Intertroch" view showing both Tip-Apex Analysis and Neck Shaft Analysis.

Flowchart N, FIG. 33, shows scaling and measurement for APEX TIP calculation as referenced in Flowchart L, step 610, FIG. 23. The technique begins, step 700, and a fixation screw is inserted, step 702. An AP (Anterior-Posterior) X-ray-type photo is taken, step 704, and the AP image is scaled, step 706, by measuring the length or width of the screw as shown in FIG. 34 or by measuring another object of known size. The Tip-Apex distance is measured, step 708, such as shown in FIG. 35. A lateral X-ray-type image is taken, step 710, and the lateral image is scaled, step 712, by measuring the screw as shown in the right-hand image of FIG. 36; alternatively, another object of known size is measured in the image and compared to the known measurement. The Tip-Apex distance is measured, step 714, in the lateral image such as shown in FIG. 37. AP and lateral Tip-Apex distances are calculated, step 716, and the results are displayed such as shown in FIG. 38. If the measurement is not satisfactory, step 718, then the technique returns in one construction to step 704 where replacement x-ray-type photos are taken and reanalyzed. Alternatively, or if re-analysis still does not reveal acceptable measurements, the surgeon repositions the screw as an alternative to step 702, and then the guidance resumes with step 704. Once acceptable, the procedure concludes, step 720, and the technique returns to step 612, FIG. 23.

FIG. 34 represents a screen view 730 of an image of a screw 732 implanted through an implant 734 to treat an intertrochanteric hip fracture, showing measurement of the screw 732 with a longitudinal axis or length line 736, guided by reference squares 737, 738, 739 and 740 generated by the present system in this construction. FIG. 35 is a view 730' similar to FIG. 34 showing measurement of Tip-Apex distance 742 of 8.2 mm, guided by reference squares 743, 744, 745 and 746. FIG. 36 is a view 730' similar to FIG. 35 plus a lateral view 750 on the right-hand side of the screen, showing measurement of the width of the screw 732 with line 752, guided by reference squares 753, 754, 755 and 756. FIG. 37 is a view similar to FIG. 36 showing measurement of Tip-Apex distance in the right-hand image 750' with a Tip-Apex line 762 of 3.6 mm, guided by reference squares 763, 764, 765 and 766. FIG. 38 is a combined "Intertroch" view 770 showing both Tip-Apex Analysis and Neck Shaft Analysis. The Lateral Tip Apex measurement of 3.6 mm from view 750' is added to the AP Tip Apex measurement of 8.2 mm from view 730' to calculate a Combined Distance of 11.8 mm in this example. An overlay 780 of normal view 782 and fractured view 784 enables visual comparison, as well as image recognition and analysis, to calculate a Fractured Neck Shaft Angle of 123 degrees and a Normal Neck Shaft Angle of 133 degrees.

Figure 39:
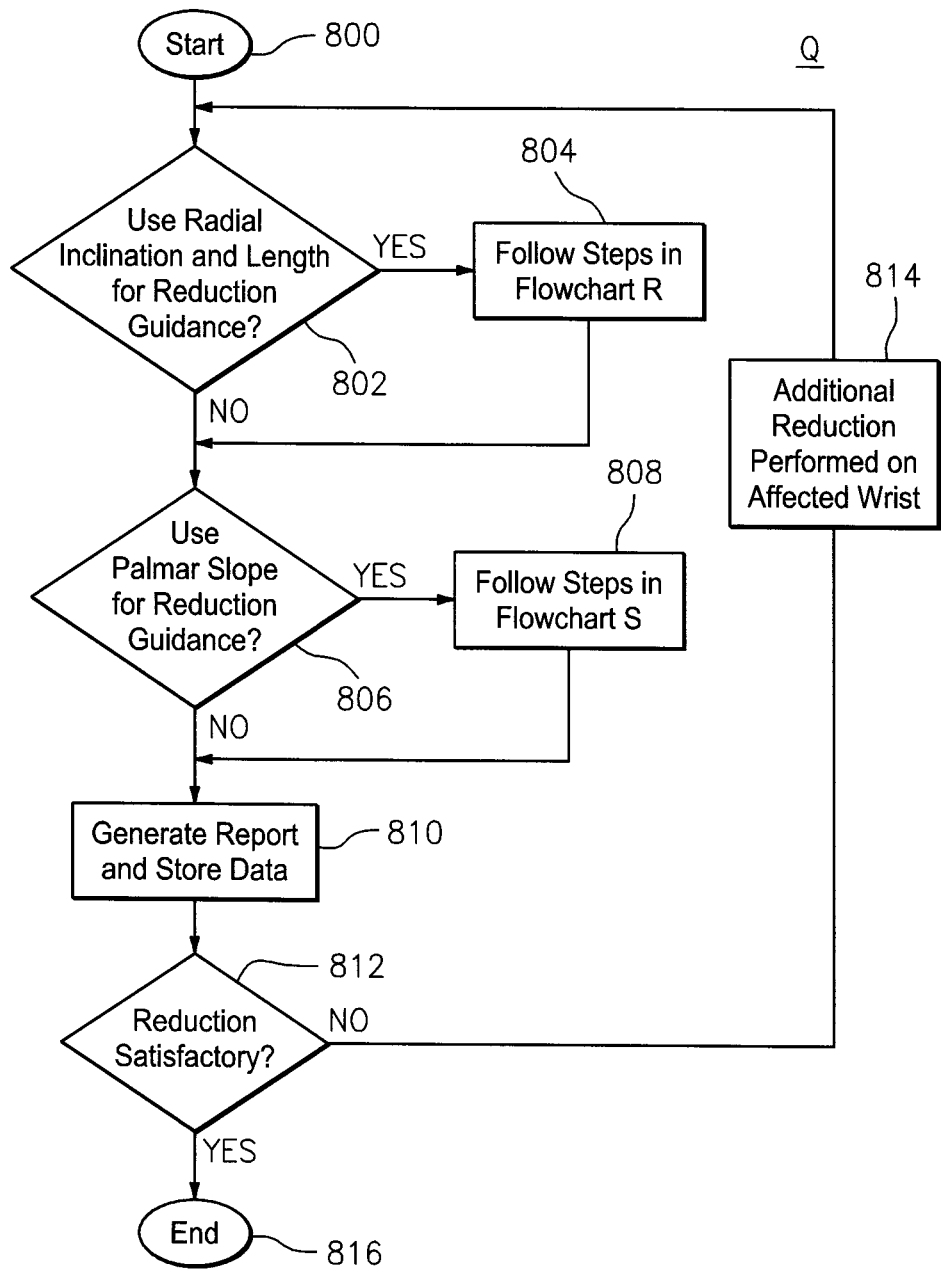
FIG. 39 is Flowchart Q of Intraoperative Guidance for Distal Radius Fracture Reduction according to another aspect of the present invention, referencing Flowcharts R and S.

Guidance according to the present invention can be provided for other anatomical regions such as wrists-hands, ankles-feet, and spinal anatomy. Flowchart Q, FIG. 39, provides Intraoperative Guidance for Distal Radius Fracture Reduction in wrists according to another aspect of the present invention, referencing Flowcharts R and S. This procedure begins, step 800, and a choice is made whether to use radial inclination and length for reduction guidance, step 802. If yes, the procedure outlined in Flowchart R is followed, step 804. Once completed, or if those features are not selected at step 802, then use of Palmar slope for reduction guidance is considered at step 806. If selected, the procedure summarized by Flowchart S is followed, step 808. After completion, or if Palmar slope is not selected at step 806, then a report is generated and data stored, step 810. If the radial fracture reduction is not satisfactory, additional reduction is performed on the affected wrist, step 814, and the technique returns to step 802. Once satisfactory, the procedure ends, step 816.

Figure 40:
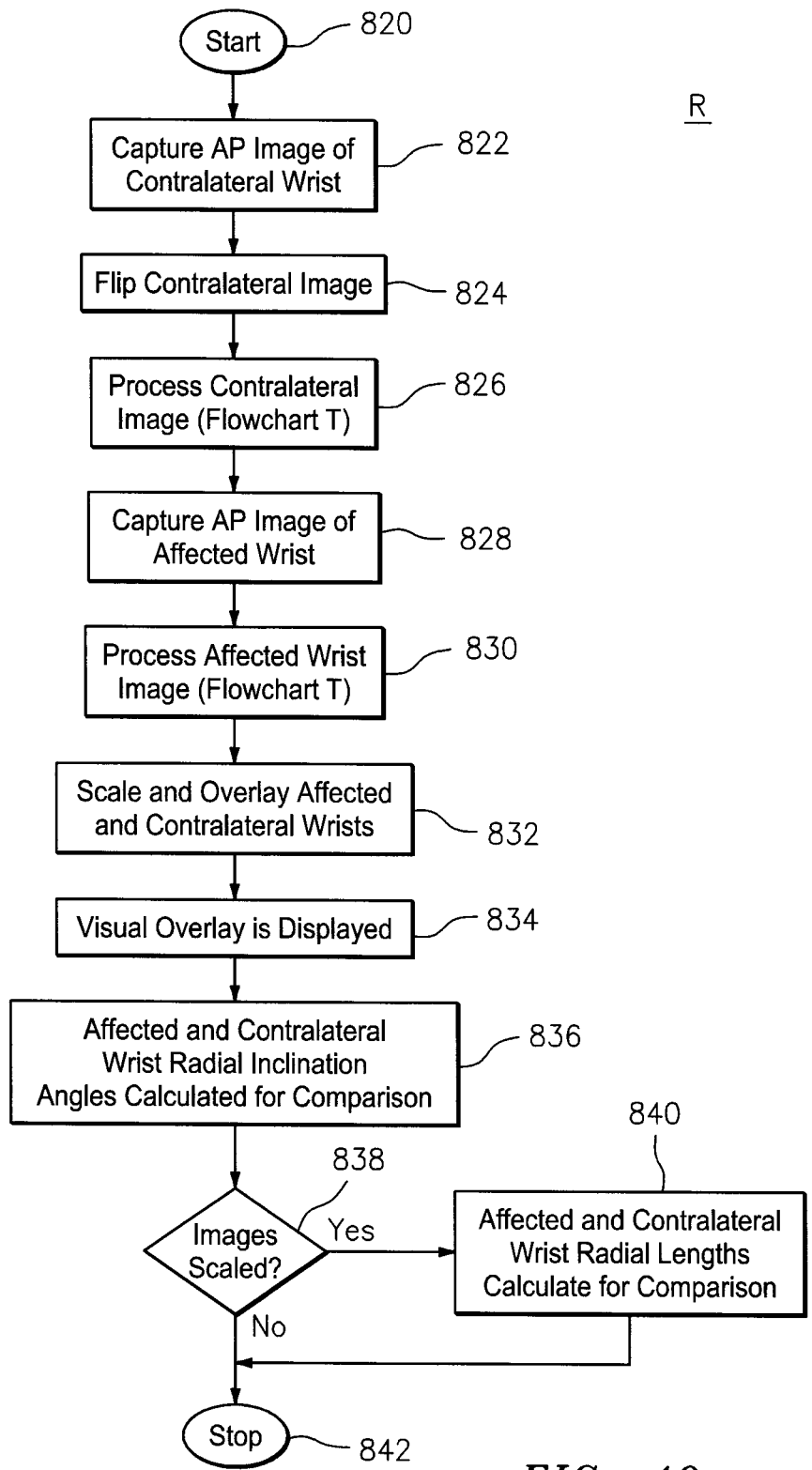
FIG. 40 is Flowchart R showing Radial Inclination and Length Reduction Guidance, and referencing Flowchart T.
Figure 51:
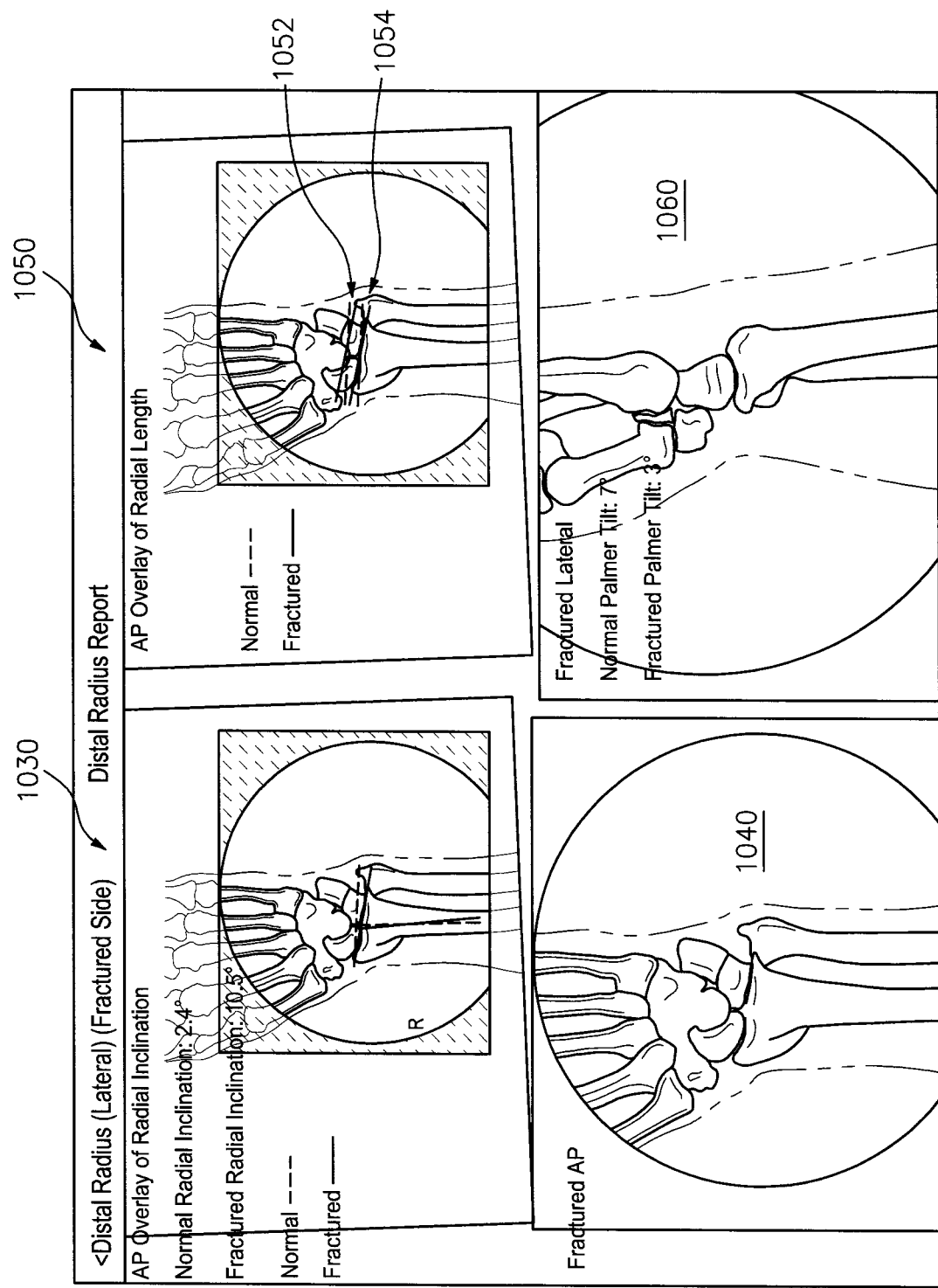
FIG. 51 is a combined view as a Distal Radius Report according to the present invention.

Flowchart R, FIG. 40, illustrates Radial Inclination and Length Reduction Guidance. An AP (Anterior-Posterior) image of the contralateral wrist is captured, step 822, and the contralateral image is flipped or inverted, step 824. The flipped contralateral image is processed utilizing the procedure outlined in Flowchart T, step 826, and an AP image is captured, step 828, for the affected wrist on which surgery is to be performed. The affected wrist image is processed utilizing the Flowchart T procedure, step 830, and the images are scaled and overlaid, step 832, such as illustrated in FIG. 51. The affected and contralateral wrist radial inclination angles are calculated for comparison, step 836, and a decision whether to scale the images is made, step 838. If yes, the affected and contralateral wrist radial lengths are calculated for comparison, step 840. After such calculations, or if not selected, the procedure ends, step 842, and the technique returns to step 806, FIG. 39.

Figure 41:
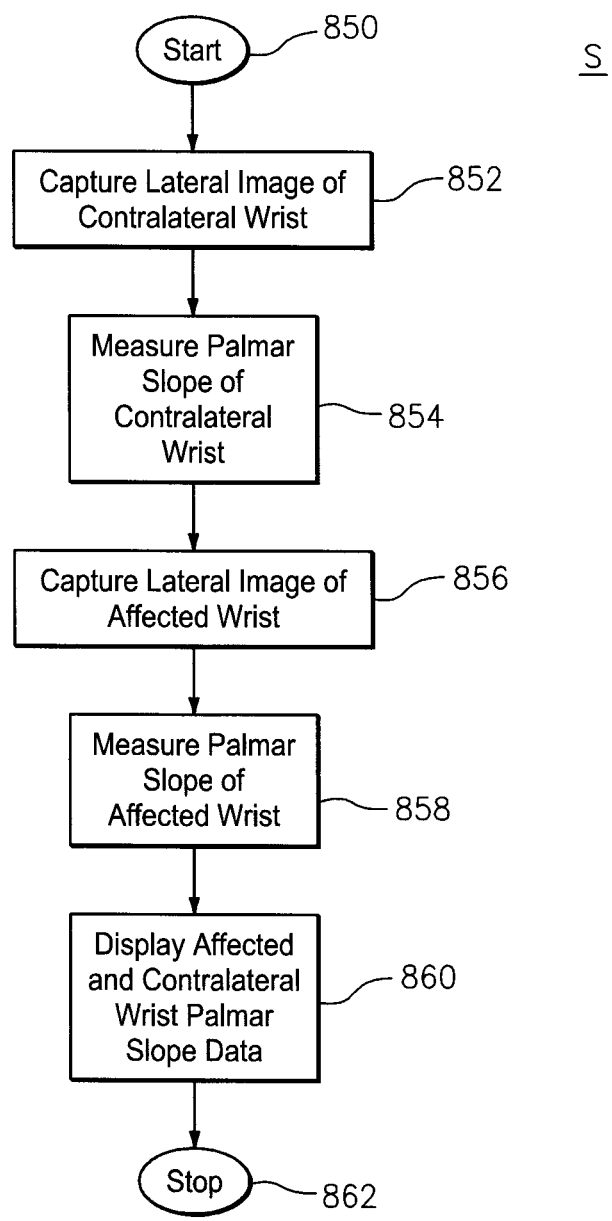
FIG. 41 is Flowchart S showing Palmar Slope Reduction Guidance.
Figure 46:
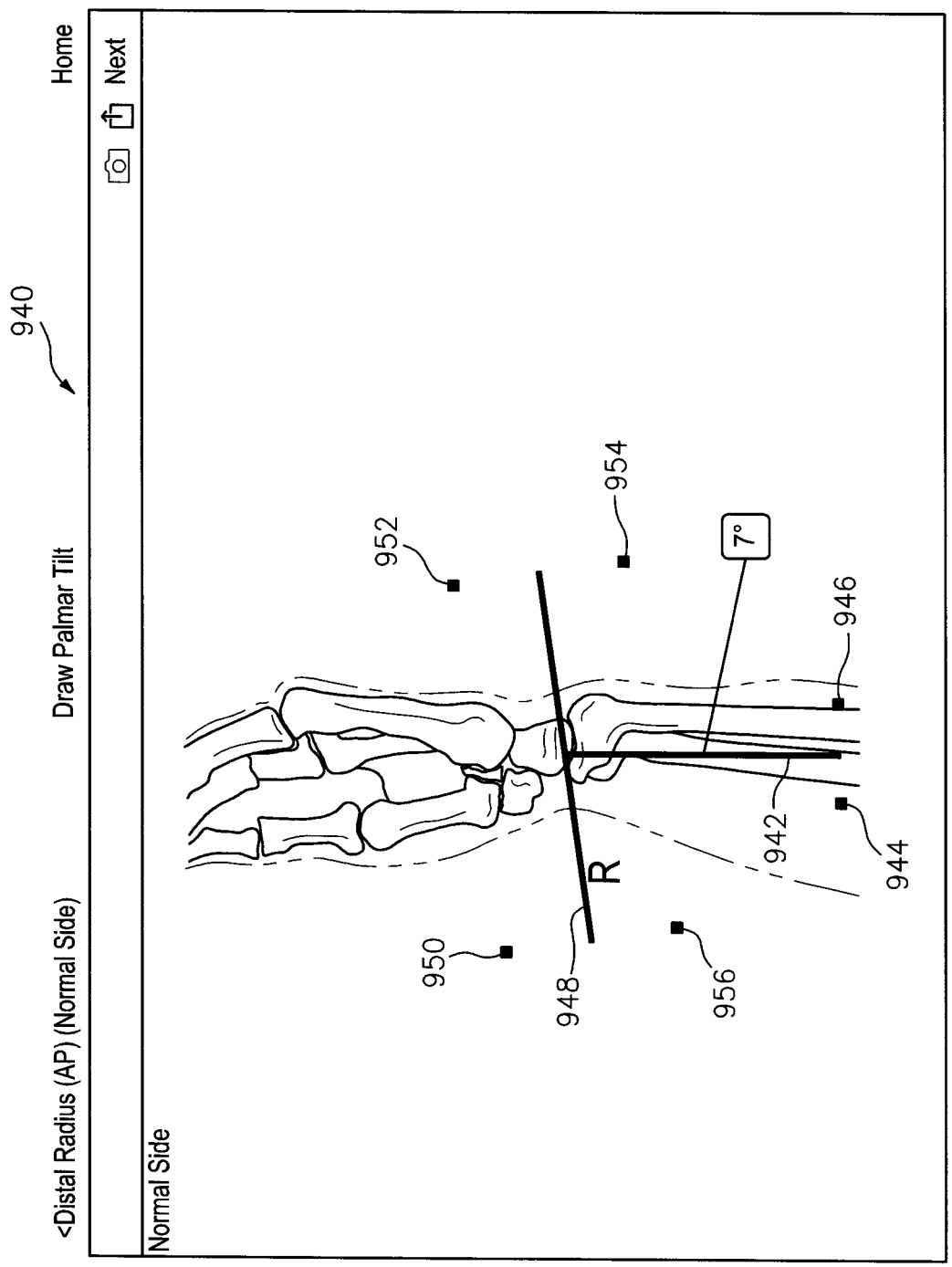
FIG. 46 is a view of an image of the normal wrist rotated to draw Palmar Tilt.
Figure 50:
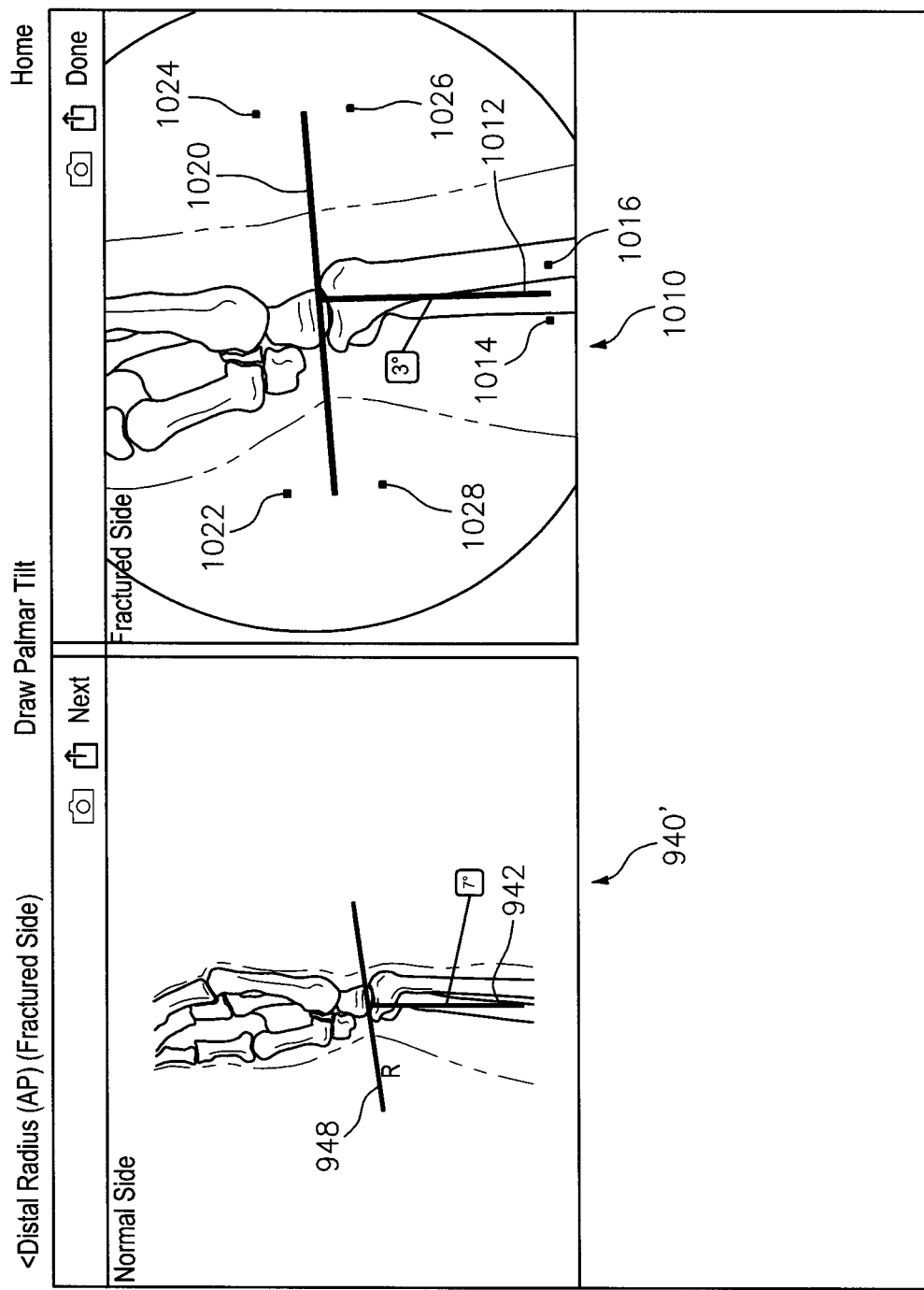
FIG. 50 is a screen view with the left-hand image similar to FIG. 46 and a right-hand image of the fractured wrist rotated to draw Palmar Tilt.

Flowchart S, FIG. 41, depicts Palmar Slope Reduction Guidance. This procedure begins, step 850, and an image of the contralateral, normal wrist is captured, step 852. The Palmar slope or tilt is measured, step 854, such as shown in FIG. 46. A lateral image of the affected wrist is captured, step 856, and the Palmar slope of the affected wrist is measured, step 858, such as shown in FIG. 50. Data and images for the affected and contralateral wrist are displayed, step 860, such as shown in FIG. 51. The procedure ends, step 862, and the technique returns to step 810, FIG. 39.

Figure 42:
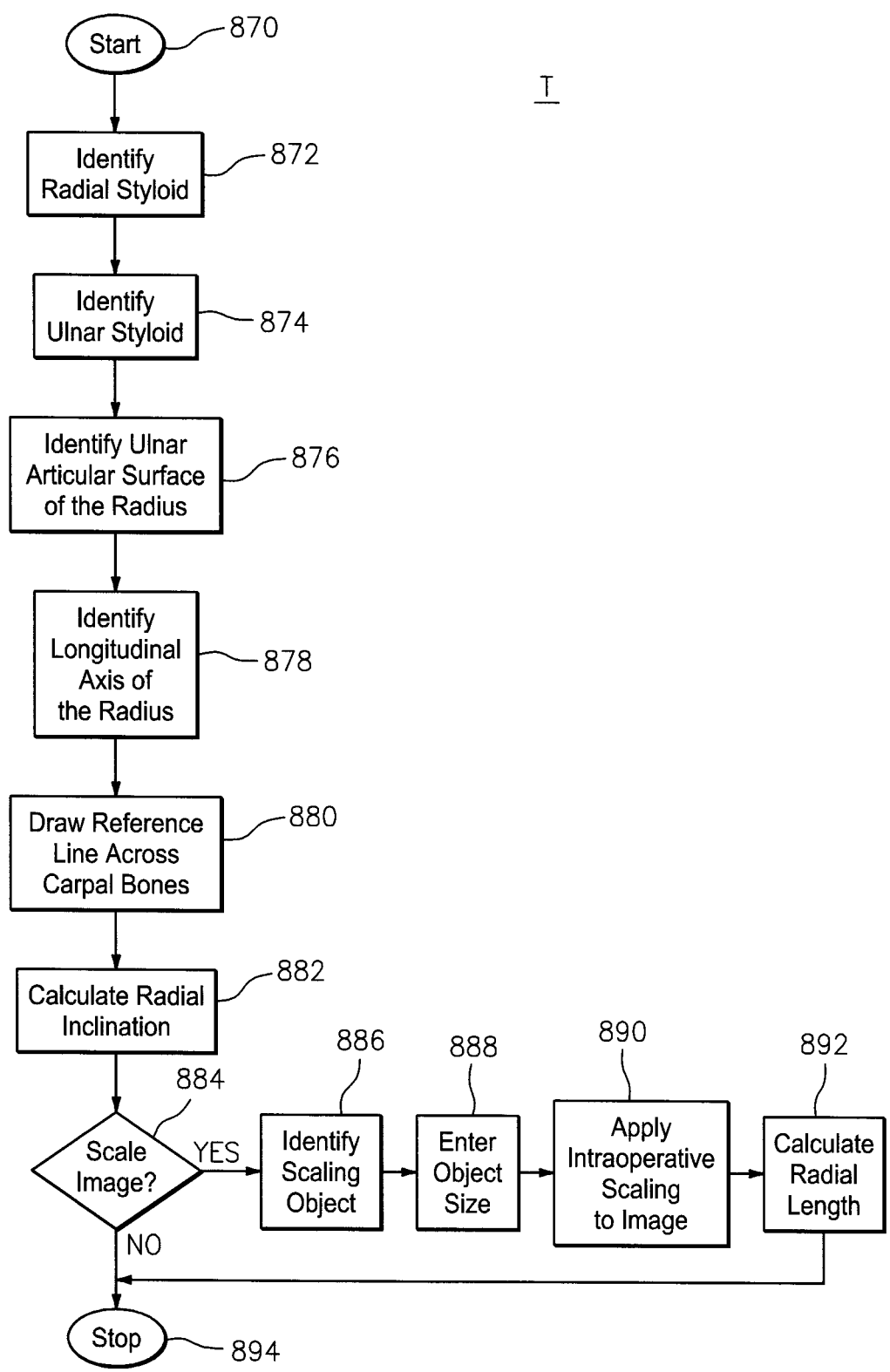
FIG. 42 is Flowchart T showing identification of various anatomical features in the wrist and image processing.
Figure 47:
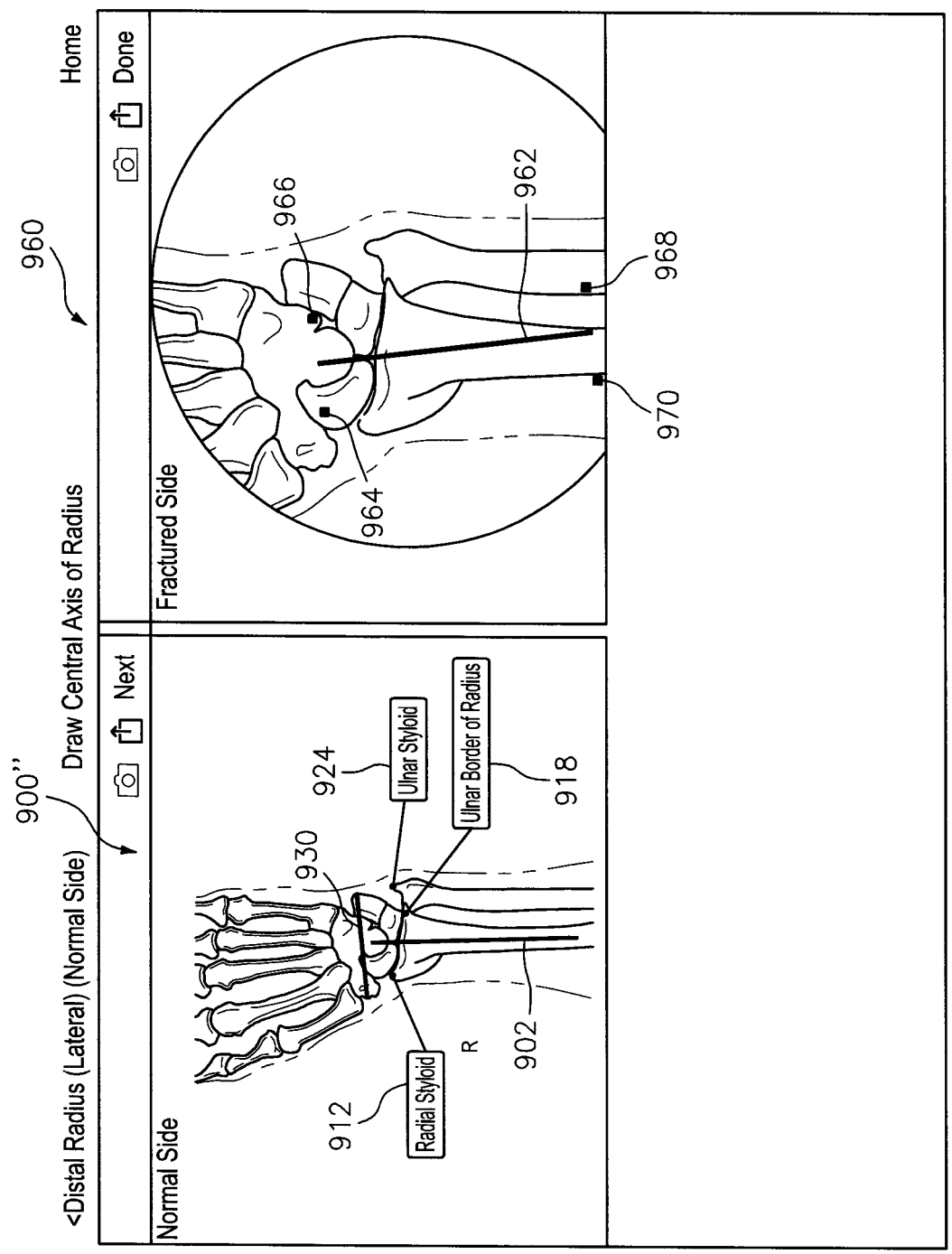
FIG. 47 is a screen view with the left-hand image similar to FIG. 45 and a right-hand image of the fractured side of the patient, showing marking of the central axis of the radius on the fractured side.

Flowchart T, FIG. 42, shows identification of various anatomical features in the wrist and image processing. It commences, step 870, and a radial styloid is identified, step 872, such as shown in FIG. 44. The ulnar styloid is identified, step 874, and the ulnar articular surface of the radius is identified, step 876. The longitudinal axis of the radius is identified, step 878, such as shown in FIGS. 43 and 47 for the normal and affected images, respectively.

Figure 45:
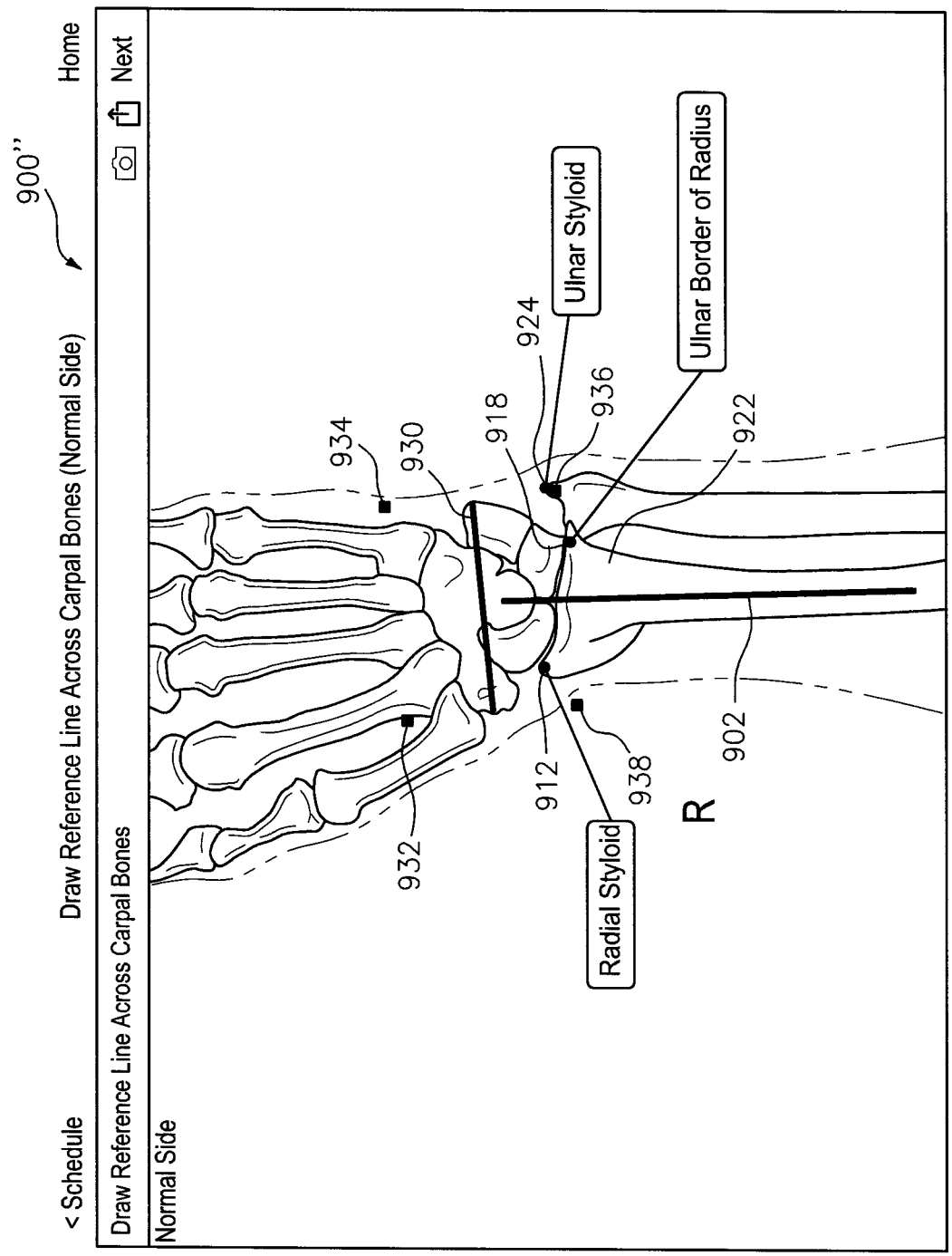
FIG. 45 is a view similar to FIG. 44 with a reference line drawn across the carpal bones to provide a stationary base reference.

A stationary base reference line is drawn across the carpal bones in this construction, step 880, such as shown in FIG. 45. The radial inclination is calculated, step 882. If the image is to be scaled, step 884, then at least one scaling object is identified, step 886, and the object size is entered, step 888. Intraoperative scaling is applied to the image, step 890, and radial length is calculated, step 892. Once completed, or if scaling is not desired, the procedure ends, step 894, and the technique returns to steps 828 or 832 of FIG. 40 as appropriate.

Figure 43:
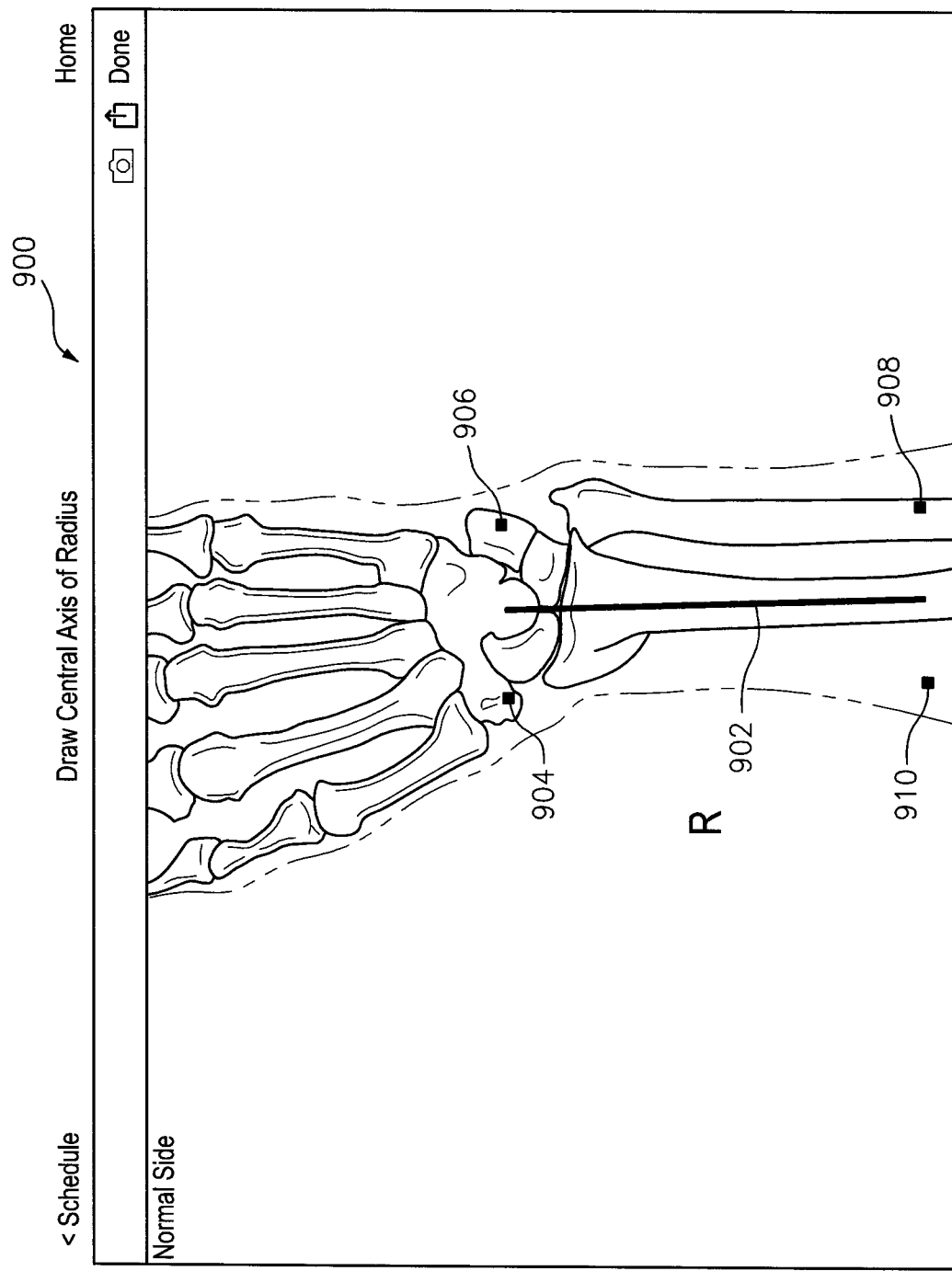
FIG. 43 represents a screen view of an image of a "normal" wrist of a patient with a line drawn on the radius to indicate its central axis.
Figure 44:
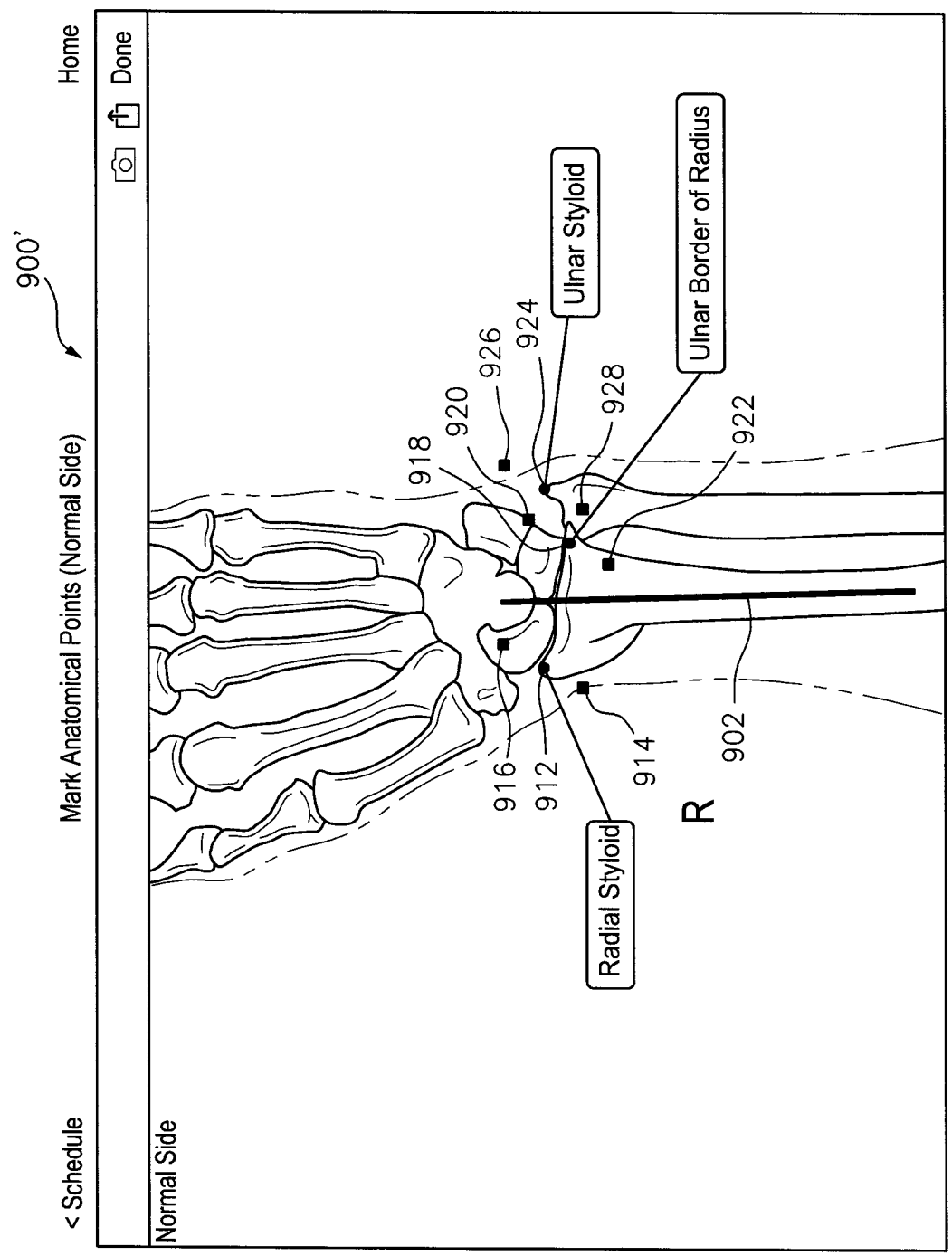
FIG. 44 is a view similar to FIG. 43 with marking of selected anatomical points.

FIG. 43 represents a screen view of an image 900 of a "normal" wrist of a patient with a line 900 drawn on the radius to indicate its central axis, guided by reference squares 904, 906, 908 and 910. FIG. 44 is a view 900" similar to FIG. 43 with marking of selected anatomical points: Radial Styloid 912, guided by reference squares 914 and 916; Ulnar Border of Radius 918, guided by reference squares 920 and 922; and Ulnar Styloid 924, guided by reference squares 926 and 928. FIG. 45 is a view 900'" similar to FIG. 44 with a reference line 930 drawn across the carpal bones to provide a stationary base reference, as guided by reference squares 932, 934, 936 and 938.

FIG. 46 is a view of an image 940 of the normal wrist rotated to draw Palmar Tilt with longitudinal reference line 942, guided by reference squares 944 and 946, and lateral reference line 948, guided by reference squares 950, 952, 954 and 956, with a calculated Tilt of 7 degrees in this example.

Figure 48:
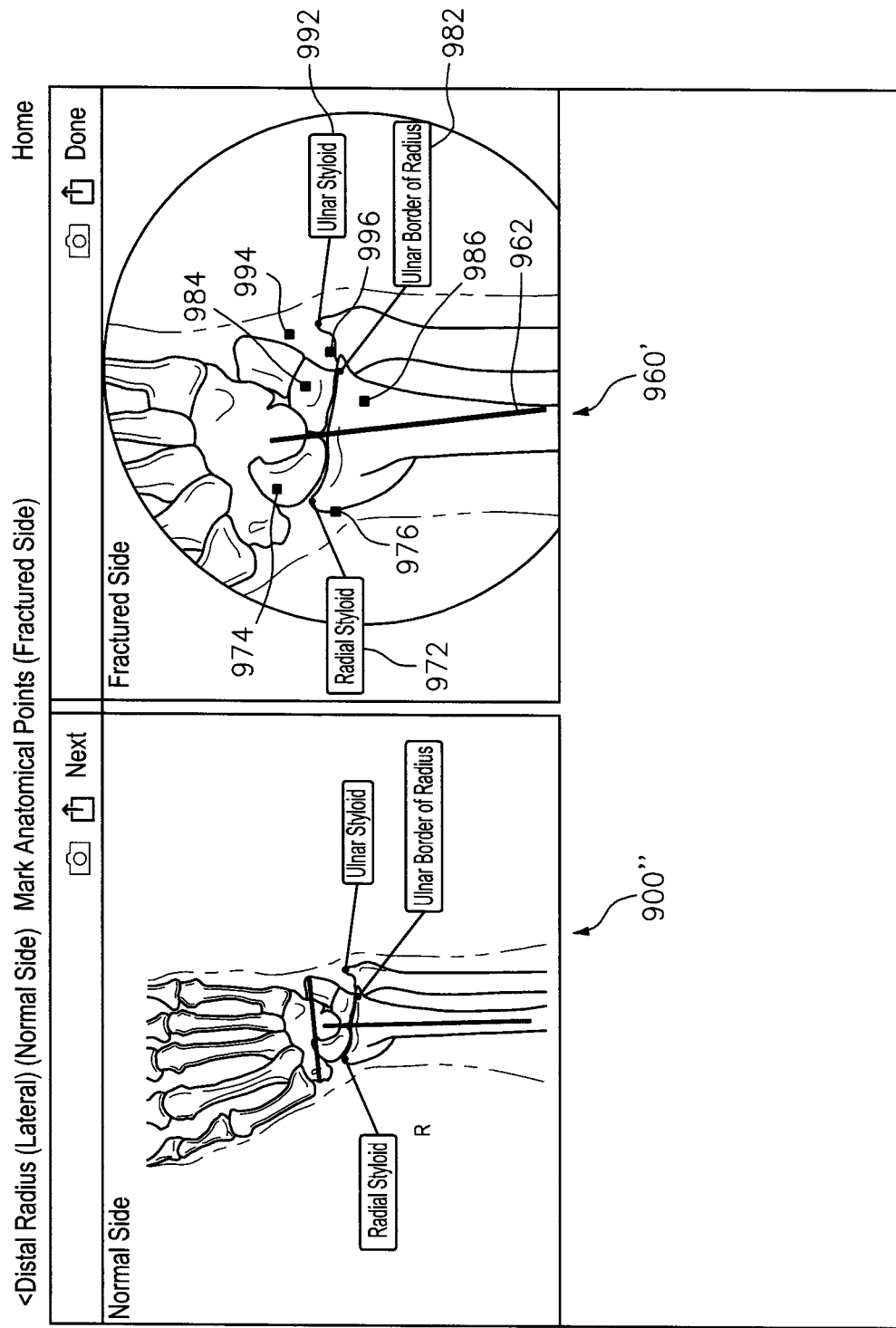
FIG. 48 is a view similar to FIG. 47 showing marking of anatomical points on the fractured side.
Figure 49:
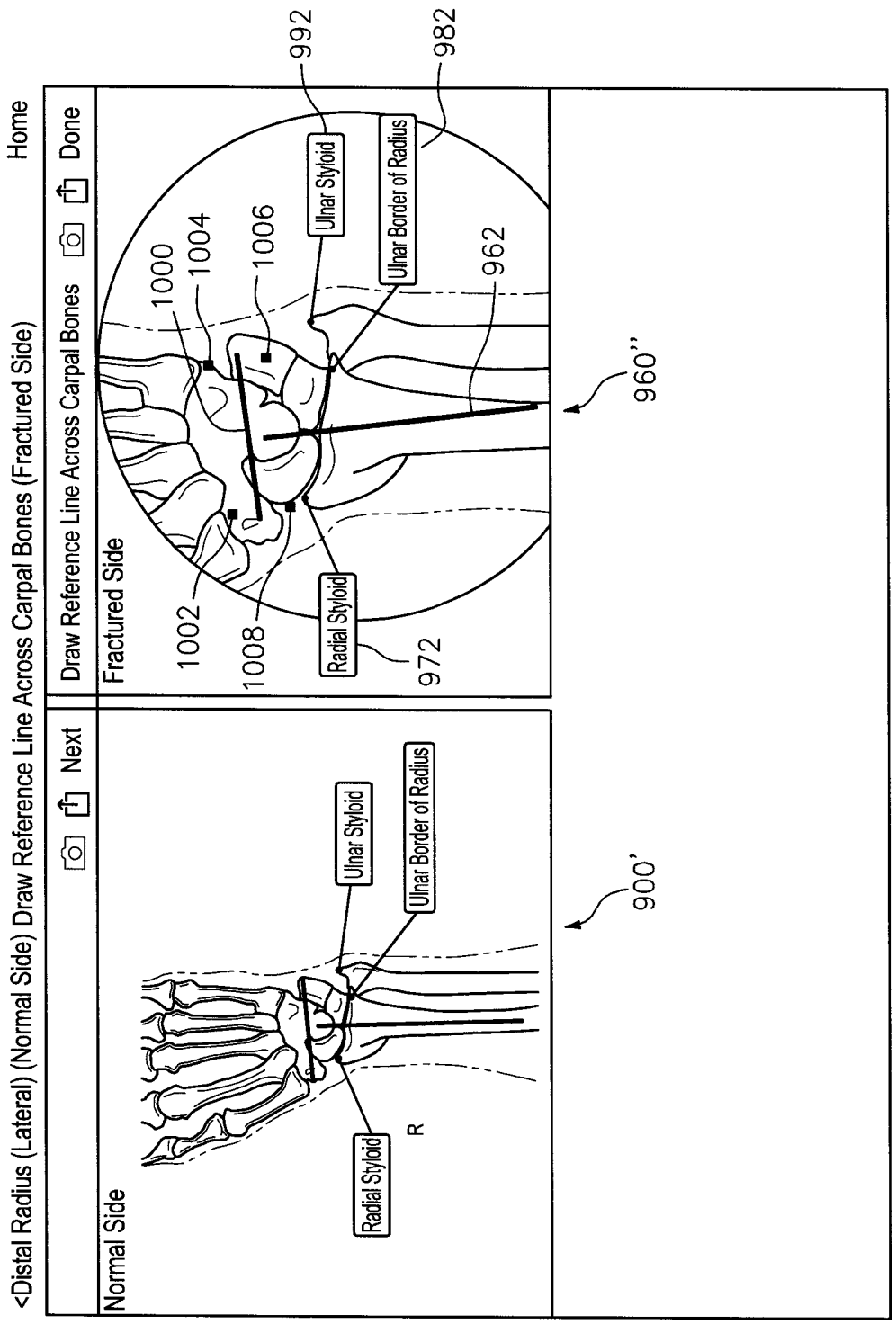
FIG. 49 is a view similar to FIG. 48 with a reference line drawn across the carpal bones on the fractured side.

FIG. 47 is a screen view with the left-hand image 900'" similar to FIG. 45 and a right-hand image 960 of the fractured side of the patient, showing marking of the central axis 962 of the radius on the fractured side, guided by reference squares 964, 966, 968 and 970. FIG. 48 includes a screen view image 960' similar to image 960, FIG. 47, showing marking of anatomical points on the fractured side: Radial Styloid 972, guided by reference squares 974 and 976; Ulnar Border of Radius 982, guided by squares 984 and 986; and Ulnar Styloid 992, guided by squares 994 and 996. FIG. 49 is a view 960" similar to FIG. 48 with a reference line 1000 drawn across the carpal bones on the fractured side, guided by reference squares 1002, 1004, 1006 and 1008. In this constructions, a user touches one of the squares with a finger or a mouse cursor, and utilizes the square, such as by 'dragging' it, to move a marker to a desired location. This enables manipulation without blocking the location of interest.

FIG. 50 is a screen view with the left-hand image 940' similar to FIG. 46 and a right-hand image 1010 of the fractured wrist rotated to draw Palmar Tilt with longitudinal reference line 1012, guided by reference squares 1014 and 1016, and lateral reference line 1020, guided by reference squares 1022, 1024, 1026 and 1028, with a calculated Tilt of 3 degrees in this example. FIG. 51 is a combined view as a Distal Radius Report according to the present invention, after the fractured side has been reduced, that is, after a surgical operation has been performed on the fractured side. The "Normal" image is an inverted contralateral image of the opposite wrist-bones of the patient. Although not illustrated, one or more plates or other implants may be utilized before and/or after analysis according to the present invention to reduce fractures as part of the surgical procedures to restore orthopaedic functionality at the surgical site. Upper-left Image 1030 is an AP Overlay of Radial Inclination to analyze radial bone fracture reduction with specific regard to angle in AP orientation. Contralateral or 'Normal' Radial Inclination is 2.4 degrees in this example and the Fractured Radial Inclination is 10.5 degrees. Radial inclination reference lines for the normal wrist-bones are shown in dashed lines while reference lines for the fractured wrist-bones are shown in solid lines. Preferably, an overlay line passing through the carpal bones in the each of images is utilized as stationary bases to generate images 1030 and 1050, although these overlay lines are not shown in images 1030 and 1050. Lower-left Image 1040 is an AP image of Reduced Fracture, after reduction has been analyzed by the system, to confirm image capture for future reference and digital record-keeping.

Upper-right Image 1050 in FIG. 51 is an AP Overlay of Radial Length to compare analysis of reduced radial bone location, with two sets 1052 and 1054 of substantially parallel lines, also with dashed lines for Normal and solid lines for Fractured wrist-bones. The distance between the two sets 1053, 1054 of lines indicates radial length measurement. Radial length lines are drawn using radial styloid and ulnar styloid location information. The quality of the fracture reduction is thereby analyzed; changes in radial length may indicate an orthopaedic problem. Image 1050 enables the user to visually inspect and analyze the quality of the fracture reduction and, therefore, numerical values are not provided in image 1050 in this construction. Lower-right Image 1060 is a Lateral View of Distal Radius Fracture after Reduction to provide Palmar Tilt analysis that compares fractured Palmar Tilt angle of 3 degrees in this example to the contralateral or 'Normal' Palmar Tilt angle of 7 degrees, although only the fractured wrist-bones are shown in image 1060 in this construction.

FIGS. 52 and 53 are described above.

Figure 54:
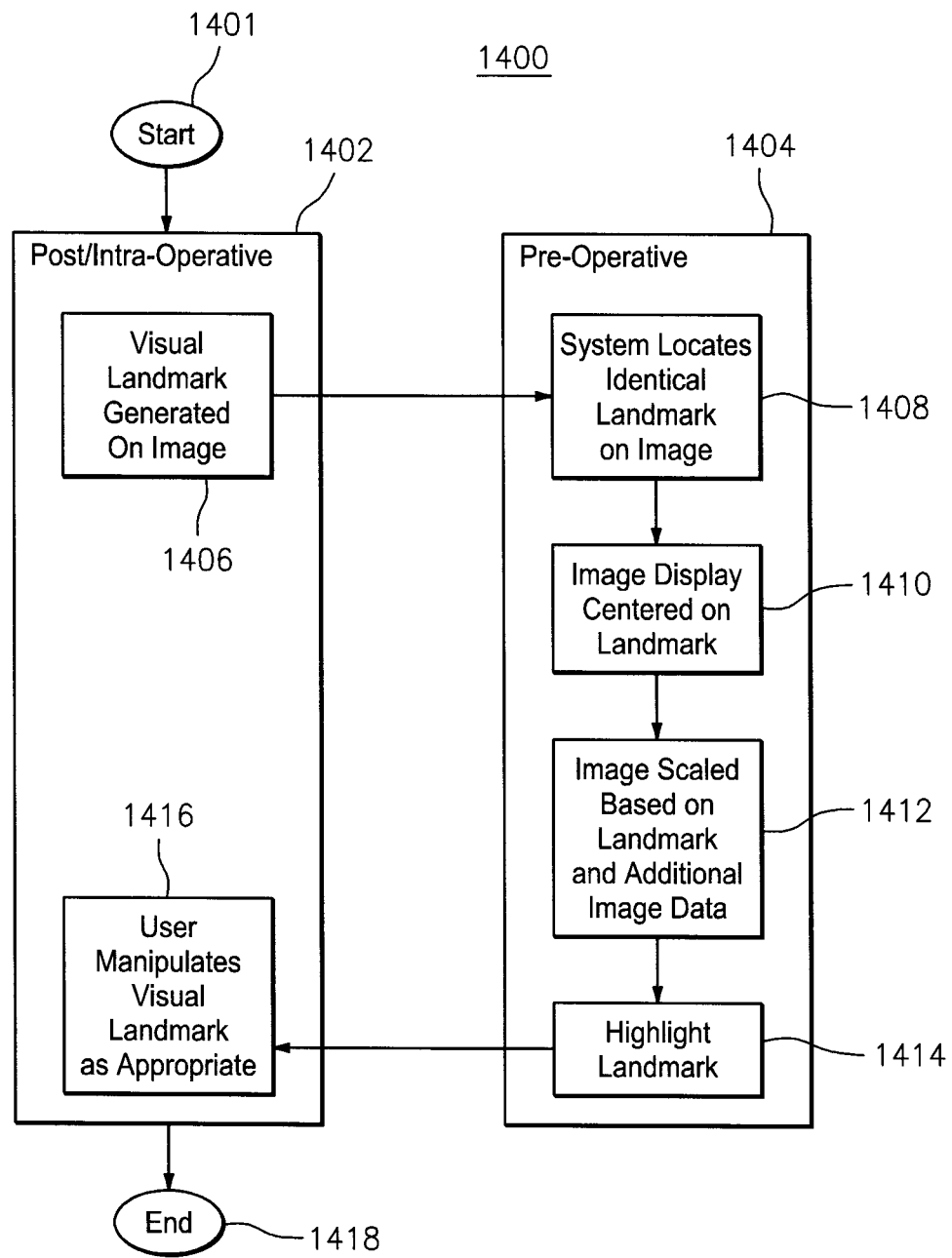
FIG. 54 is a schematic combined block diagram and flow chart of an identification guidance module utilized according to the present invention.

In some constructions, a guidance system is provided to adjust the viewing area of one image on a screen to track actions made by a user to another image on the screen, such as to focus or zoom in on selected landmarks in each image. This feature is also referred to as an automatic 'centering' function: as a user moves a cursor to 'mark' a feature on one image, such as placing a point for a landmark or a stationary base on an intraoperative image, the other image on the screen is centered by the system to focus on identical points of interest so that both images on the screen are focused on the same anatomical site. FIG. 54 is a schematic combined block diagram and flow chart of an identification guidance module 1400 utilized in one construction to assist a user to select landmarks when comparing a post- or intra-operative results image, box 1402, with a reference image, box 1404. The module is initiated with a Start 1401 and terminates with an End 1418. When a visual landmark is added to a post-operative image, box 1406, the module 1400 locates all landmarks "1" on the pre-operative reference image, box 1408, and calculates the visible area "v" within the pre-operative image in which to scale, such as by using Equation 11:

$$v=[\max x(1)-\min x(1),\max y(1)-\min y(1)] \quad \text{EQ.11}$$

The identical landmark on the pre-operative image is located and its center-point "c" is determined, box 1410. The identical landmark on the pre-operative image is highlighted in one construction to increase its visual distinctiveness, box 1414. The pre-operative image is centered, box 1410, and scaled, box 1412, such as by utilizing the following Equations 12 and 13, respectively:

$$\text{Center}=c-(v)(0.5) \quad \text{EQ.12}$$

$$\text{Scale}=i/v \quad \text{EQ.13}$$

The user manipulates one or more visual landmarks in the results image, box 1416, as desired and/or as appropriate. In some constructions, the user manually ends the guidance activities, box 1418 and, in other constructions, the system automatically discontinues the guidance algorithm.

In certain constructions, image recognition capabilities provide "automatic", system-generated matching and alignment, with a reduced need for user input. Currently utilized image recognition provides automatic detection of selected items including: the spherical ball marker frequently utilized in preoperative digital templating; the acetabular cup in digital templates and in trial prosthetics; and the Cobb Angle line, also referred to as abduction angle.

Note that "PostOp" typically indicates post-insertion of a trial prosthesis during the surgical procedure, and is preferably intra-operative. The PostOp image can also be taken and analysis conducted after a "final" prosthesis is implanted. "PreOp" designates an image preferably taken before any surgical incision is made at the surgical site. In some situations, the image is taken at an earlier time, such as a prior visit to the medical facility and, in other situations, especially in emergency rooms and other critical care situations, the "PreOp" image is taken at the beginning of the surgical procedure. Ball markers BM are shown but are not utilized for alignment because ball markers can move relative to the patient's anatomy. Further PreOp and PostOp icons are provided to adjust viewing features such as contrast and transparency. Preferably, at least one icon enables rotation in one construction and, in another construction, "swaps" the images so that the underlying image becomes the overlying image.

In certain constructions, intraoperative analysis and guidance is also provided to a user for one or more individual components of an implant such as an acetabular cup of a hip implant. System 1500, FIG. 55, analyzes the orientation, including abduction angle and anteversion, of an acetabular cup in this construction. System 1500 includes Image Selection Module 1502, Image Recognition Module 1504, Landmark Identification Module 1506, Acetabular Cup Bottom Identification Module 1508 and Abduction Angle and Anteversion Calculation Module 1510 in this construction, with system operation and technique described below in relation to FIGS. 56-59.

Figure 56:
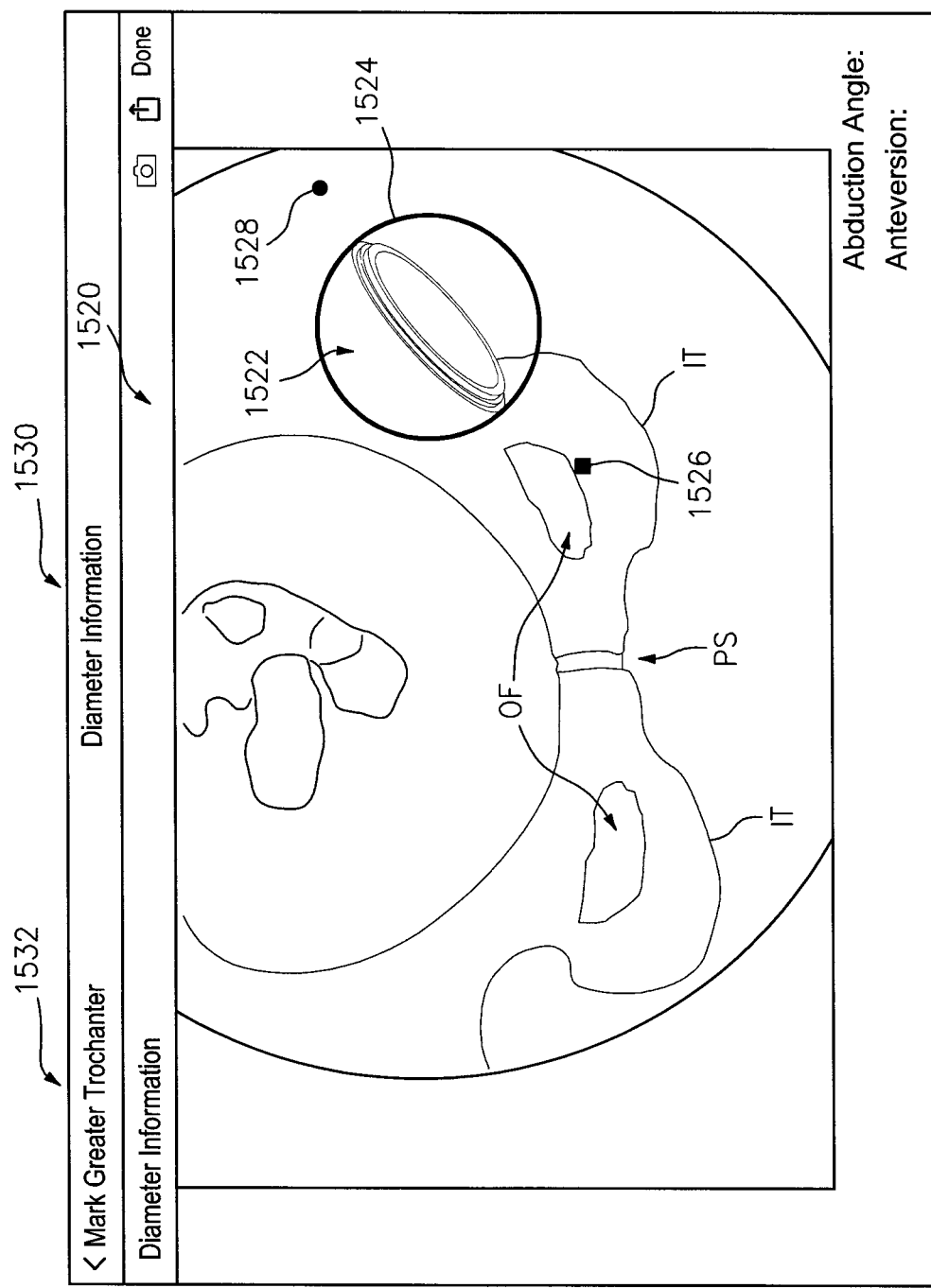
FIG. 56 is an image of an acetabular cup positioned in the left acetabulum of a patient with a circle drawn around its hemispherical surface to provide diameter information.

FIG. 56 is an image 1520 of an acetabular cup 1522 positioned in the left acetabulum of a patient with a circle 1524 drawn around its outer hemispherical surface to provide diameter information for the component. In some constructions, a user initiates component analysis by touching a finger or a stylus to the "Diameter Information" field 1532. At any time, as described in relation to FIG. 59 below, the user preferably is able to return to a previous action such as by touching or clicking another field 1532, for example "Mark Greater Trochanter". In one construction, an image recognition algorithm in Image Recognition Module 1504 automatically operates to identify the acetabular cup 1522 in the image 1520 of FIG. 56 and surround it with the circle 1524, bracketed by small guide dots 1526, 1528, as indicated by the prompt "Diameter information" 1532 at the top of image 1520. In some constructions, the guide dots or squares serve as "navigation handles" to enable the user to manipulate one or more features designated by the handles, such as by touching or clicking and dragging the handles to move the designated features. This screen 1520 relates to step 1608 in flowchart X, algorithm 1600, FIG. 59 below. If the initial, auto-generated circle is not acceptable, then the user manually adjusts the position and/or size of circle as appropriate, step 1610.

Figure 57:
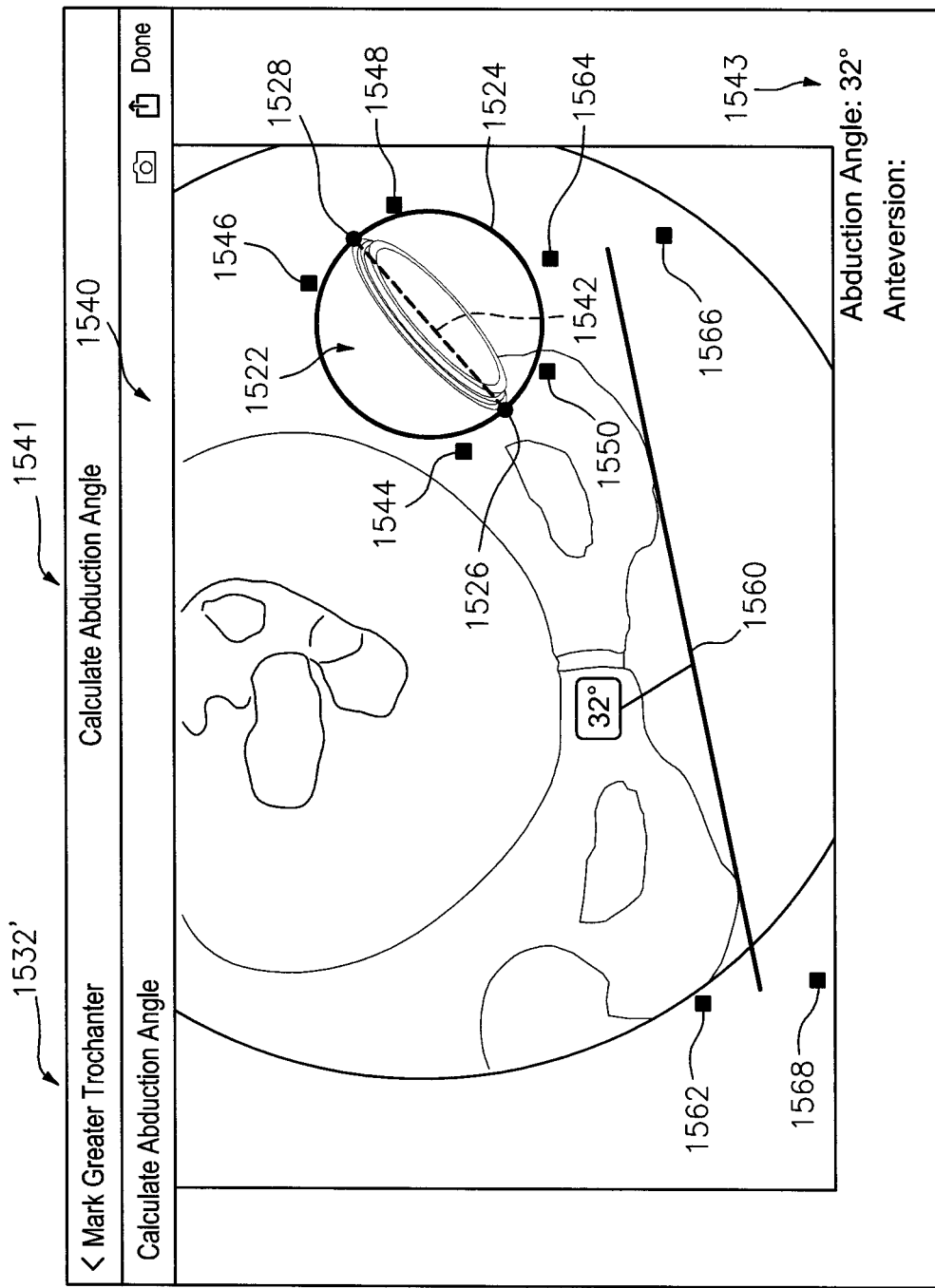
FIG. 57 is an image similar to that of FIG. 56 with a line segment drawn under the cup to calculate abduction angle relative to a neutral axis line.

FIG. 57 is an image 1540 similar to that of FIG. 56 with two lines 1542 and 1560 drawn to calculate abduction angle. The user accesses screen 1540, having a heading or prompt 1541 of "Calculate Abduction Angle", for example, to fit in the abduction angle landmarks for calculation. The terms "abduction" and "abduction angle" are also known as "inclination". The "User positions neutral axis" step 1612 in flowchart X, FIG. 59 below relates to screen 1540, FIG. 57, in which neutral axis line 1560 is placed to touch the two ischial tuberosities of the pelvic girdle. Guide squares 1562, 1564, 1566 and 1568 enable the user to manipulate the neutral axis line 1560. Abduction angle line segment 1542 is auto-positioned across circle 1524 using image recognition, step 1614, FIG. 59, wherein the system automatically detects where the acetabular cup 1522 is positioned, FIG. 57, and the system places the line segment 1542 across the abduction angle on the cup as accurately as it can do so. The abduction line segment 1542 preferably is a diameter line of the circle; when segment 1542 is extended virtually by the system to intersect the neutral axis line 1560, the abduction angle is generated and measured at that intersection. In one construction, the abduction line defaults to about 45 degrees from the neutral line 1560 until more accurate auto recognition occurs. The guide square "handles" 1544, 1546, 1548 and 1550 around the abduction line segment 1542 enable the user to rotate the abduction line segment 1542, but the abduction line continues to look like a diameter line so that it remains properly aligned with the actual orientation of the acetabular cup 1522.

Figure 59:
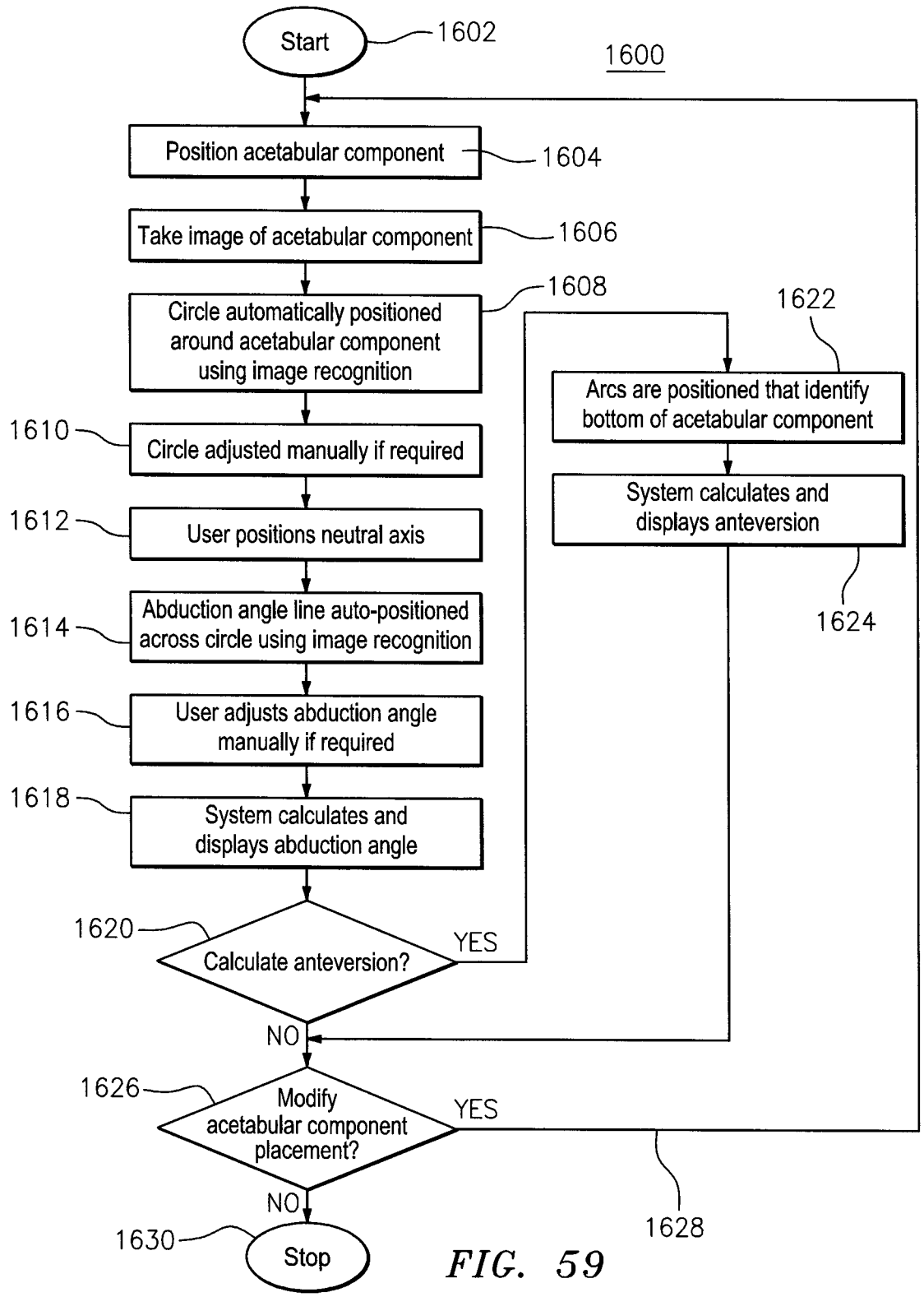
FIG. 59 is a Flowchart X of abduction angle and anteversion analysis by the modules of FIG. 55 relative to the images of FIGS. 56-58

During the "User adjusts abduction angle manually if required", step 1616, FIG. 59, the user can use the navigation handles 1544, 1546, 1548 and 1550, FIG. 57, after the image recognition has run, to make the abduction angle substantially perfect. In "System calculates and displays abduction angle", step 1618, the neutral axis 1560 is mathematically compared to the abduction line segment 1542 to determine the angle. In this construction, the abduction angle data of "32°", for example, is displayed in lower right field 1543 in FIG. 57.

Figure 58:
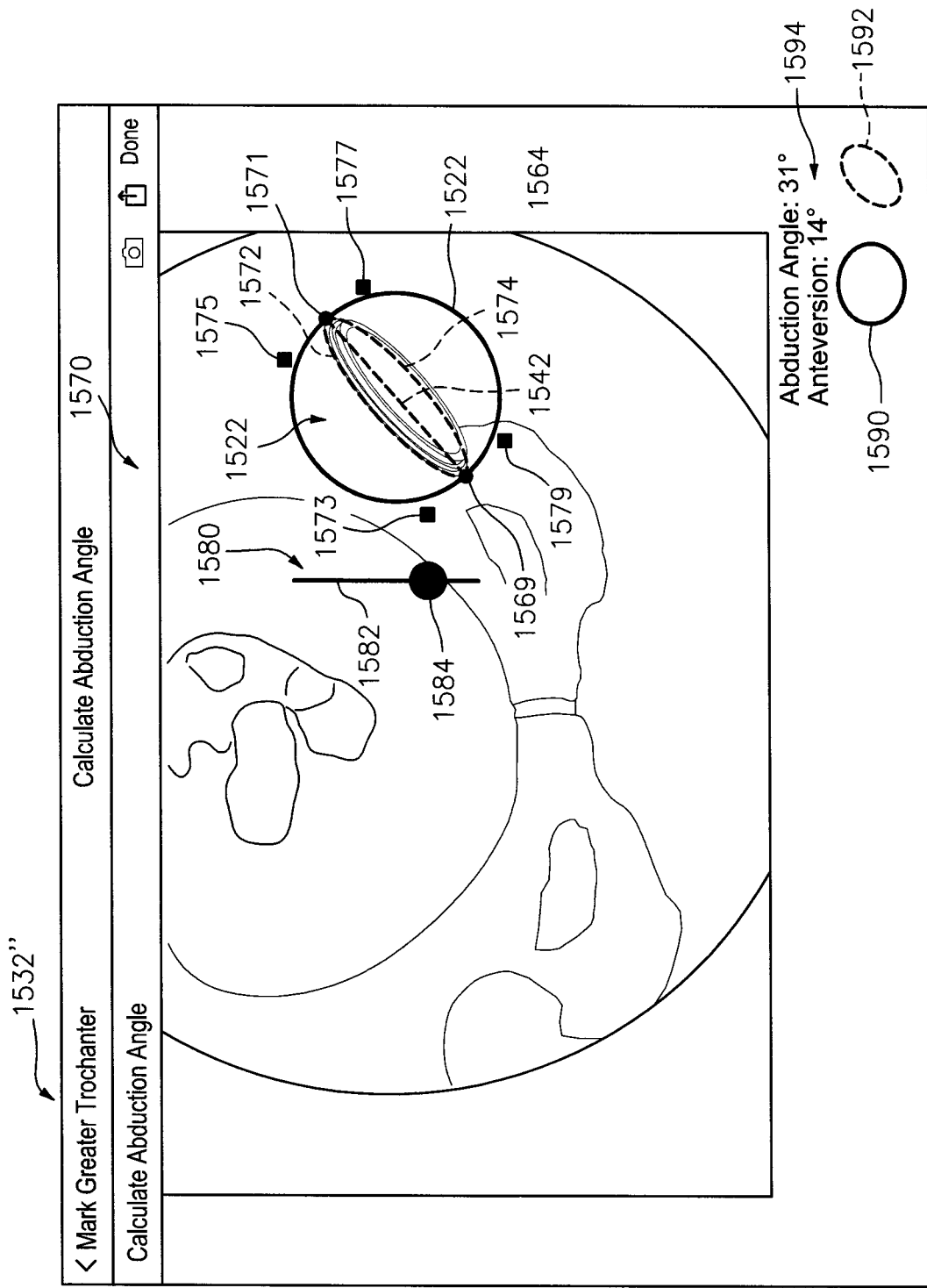
FIG. 58 is an image similar to that of FIG. 57 with arcs drawn at the bottom of the acetabular cup to assist calculation of anteversion.

If the user wants anteversion information, then at step 1620, FIG. 59, "YES" is selected and arcs 1572, 1574, FIG. 58, are positioned that identify the bottom of the acetabular component 1522 in step 1622. The system then calculates and displays the anteversion angle, which relates to the z-plane rotation of the acetabular component 1522. Some users may only want to use abduction angle data and will then skip anteversion at step 1620 and proceed to step 1626 where it is decided whether to modify placement of the acetabular component intraoperatively. If "yes" is selected, then the algorithm proceeds as indicated by path 1628 to re-position the acetabular component, step 1604 et seq. Once the user is satisfied with the placement, then algorithm 1600 terminates, step 1630, and the system resumes from where step 1602 was initiated.

FIG. 58 is an image 1570 similar to that of FIG. 57 with arcs drawn at the bottom of the acetabular cup 1522 to assist calculation of anteversion in the z-plane. Image 1570 includes a vertically-oriented "slider control" 1580 in this construction, with vertical line 1582 and a movable setting knob 1584, to enable a user to easily increase or decrease the size of arcs 1572 and 1574. Vertical slider control 1580 increases or decrease the size of the arcs 1572, 1574. These arc lines 1572, 1574 are mirror images of one another relative to the abduction line segment 1542 and are used to identify the location of the bottom of the cup 1522 in the image 1570. Sliding knob 1584 all the way to '0' will cause the arcs 1572, 1574 to overlay the abduction angle line segment 1542. Sliding all the way to '100' will cause the arcs to overlay the existing circle 1524. This relates to "Arcs are positioned that identify bottom of acetabular component", step 1622, FIG. 59. Guide handles 1569 and 1571, FIG. 58, are provided for at least one of arcs 1572 and 1574 as described in relation to FIG. 59 below.

During the next step 1624, "System Calculates and Displays Anteversion", any updates that are applied to the arcs 1572, 1574 via slider 1580 will lead to re-calculation and updated display of anteversion value such as "14°" in field 1594. Note how the guide handles 1573, 1575, 1577 and 1579 in FIG. 58 allow the precise location of the abduction angle to still be updated if required, via manipulation of abduction line segment 1542, which is especially useful if the user continues positioning the arcs, to more closely achieve actual orientation values. Soft-button icons 1590 and 1592 for "Abduction Angle" and "Anteversion", respectively illustrated with solid and dashed lines, serve as "toggles" when touched or clicked by a user to selectively activate which screen features may be manipulated by the user. In one construction, the functionality of one or more of guide handles 1573, 1575, 1577 and/or 1579 is altered according to which of icons 1590 and 1592 is selected, to adjust features relating to abduction and anteversion, respectively.

Figure 55:
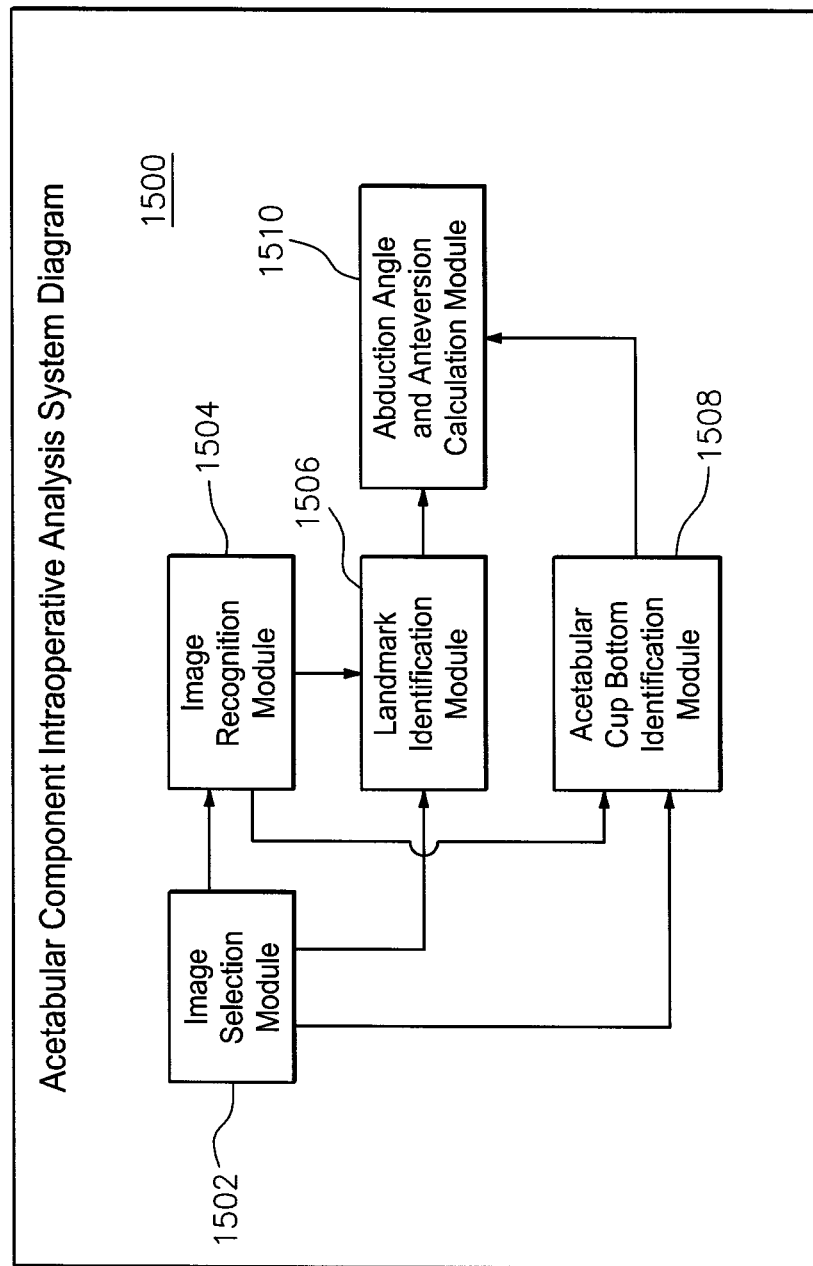
FIG. 55 is a schematic block diagram of modules that analyze the orientation of a component such as an acetabular cup to generate abduction angle and anteversion information.

FIG. 59 is a flowchart of anteversion and abduction analysis by the modules of FIG. 55. Flowchart X, algorithm 1600, FIG. 59, is activated when a user selects "Cup Check" icon or text to initiate cup analysis. In some constructions, this prompt will persist somewhere on the navigation screen throughout the workflow. This is a 'forked' or loop workflow which will start, step 1602, from wherever it is initiated and then return to the same place upon finish of the fork. First action of "Position Acetabular Component", step 1604, is conducted by a surgeon. The "acetabular component" in this situation of "pre-stem insertion", can be a number of components: a standard acetabular cup, a reamer, or a trial acetabular cup. The actual component analyzed depends on what the surgeon would like to have analyzed by the system according to the present invention.

After initial installation of a component, a prompt such as "Take image of acetabular component", step 1606, guides the user to take a picture of an AP Pelvis view with implanted cup, such as illustrated in FIG. 56. Alternatively, a prompt of "Select from Library" or other guidance can be provided to the user, in a manner similar to other techniques described above. Steps 1608-1616 are described above in relation to FIGS. 56-57 in which a circle is established around the acetabular cup and diameter information of the circle is generated.

Initiation of step 1618, FIG. 59, "System calculates and displays abduction angle", causes two lines to appear, the pelvic reference line 1560 and abduction angle line segment 1542, FIG. 57, in a manner that is similar to abduction angle analysis on simulated AP Pelvis described above. Pelvic reference line 1560 is also referred to as the "neutral axis" line, step 1612. Alternatively, a "T" or other geometric shape appears on the screen when a soft button "toggle" is activated. The pelvic reference line 1560 is a line across image 1540, placed by default horizontally on image 1540 and approximately 75 percent of the way down the image (in a y-coordinate system). This is similar to the Cobb Angle functionality discussed above.

For the abduction angle line, the user draws the line segment 1542 as precisely as possible across the cup 1522. In some constructions, an image detection/recognition algorithm is provided to assist this process. Abduction angle preferably is calculated in real time and displayed in this step. In one construction, the abduction angle continues to be displayed to the user throughout the additional steps in this process. Determining the abduction angle is a straightforward calculation, calculated as the angle between the neutral axis 1560 and abduction line segment 1542, FIG. 57, similar to how it works in AP Pelvis reconstruction. When a user such as a surgeon wants to get return to operating on the patient and not continue with anteversion, then the user selects "No" in steps 1620 and 1626, FIG. 59, the system "saves" the calculated information, and returns to where algorithm 1600 was initiated while the surgeon resumes surgery on the patient.

For step 1622, the user works with two inner arcs to analyze anteversion. The system keeps the acetabular component circle visible from the earlier step, but it is now non-modifiable. The abduction line preferably is removed from the visual display. Preferably the circle appears to be "paper thin" (and even slightly transparent) in this screen. End points 1526 and 1528, FIG. 57, are added on each side of the circle 1524 where the abduction line 1542 transected the visual circle 1524.

Now the system proceeds to modify the two arcs 1572 and 1574, FIG. 58, that are contained within the circle 1524. Each arc is on one of the sides of the abduction line segment 1542. These arcs are mirror images of one another relative to the abduction line. Each arc should default to a distance of 35% of the circle radius; for example, if the radius is 28 mm (or 28x pixels, whatever it may be, as scaling is not needed for this process), the distance of the midpoint of the arc from the abduction line should be approx. 9 mm (or 9x pixels). One of the arcs, such as the lower one 1574, has navigation controls or handles 1569 and 1571 on it, or directly at the center of the arc 1574. The other arc will move in tandem with this arc in a "captured" manner. Navigation control for this object will be a slider control (similar to a transparency control, but longer and vertical). As described above for one construction, at a setting of 100 percent on the slider, the arc will be directly on the cup, while at 0 percent on the slider, the arc will be directly on the abduction angle line. Preferably an initial default setting of 35 percent is provided. Also preferably, the slider control 1580 is movable on the screen, and is initially positioned by the system in the middle of the screen.

Anteversion is calculated in real-time and displayed as arcs 1572 and 1574 are modified. A larger display is desired for both abduction angle and anteversion. Anteversion is calculated in one construction according to Liaw et al., "A New Tool for Measuring Cup Orientation in Total Hip Arthroplasties from Plain Radiographs", Clinical Orthopaedics and Related Research No. 451, pp. 134-139 (2006) currently available at: http://www.csie.ntu.edu.tw/~fuh/personal/ANewToolforMeasuringCupOrientation.pdf.

As described on Page 136 of the Liaw et al. article, FIG. 2-B shows calculation of 'true anteversion' angle: Point F is known, as the midpoint of the diameter line, and Point E can be identified from circle surround the cup. The highest point on the cup is point E, which has the same x-coordinate as Point F and a y-coordinate equal to (y coordinate of Point F+radius of circle diameter). Point G is a point on the 'arc' horizontal from Point F. Angle Beta(t), which represents true anteversion, can be calculated from this data.

Finally, the user can Capture/Save this analysis for later review and then 'Go Back' to standard workflow. High Level Workflow Functionality Summary: preferably, the system provides the user with the ability to Save, Exit Cup Check, return to previous screen, and view after the final overlay. In some constructions, the system captures anteversion on the reconstructed AP Pelvis as well, in addition to the abduction angle calculation that already exists. A soft button with a designation such as "Calculate Anteversion" is provided for the user to click or touch at the end of 'abduction angle' process in simulated AP. If selected, then process continues, else process stops.

In some techniques, the Abduction Angle can be altered if user decides to keep a physical handle attached to the acetabular cup. The handle will appear on an x-ray image or fluoro image, and can be used to determine abduction. A perpendicular line to the cup handle line that intersects the Ischial Tub line will produce a very accurate Abduction Angle. Finally in Flowchart X, FIG. 59, is the user satisfied with the results? If not, the user can reposition the acetabular cup, retake a fluoro shot, and begin the process again as shown in the flowchart. Thus, a software-controlled solution is achieved according to the present invention, anatomically disconnected from the patient, to provide intraoperative data that improves clinical decision-making during surgery without increasing trauma to the patient.

In certain constructions, a system and method according to the present invention includes an inventive alternative methodology for analyzing intraoperative leg length and/or offset changes using a different application of the stationary base, intraoperative scaling and anatomical landmark identification techniques. Referred to herein as 'Reverse Templating", the system and method combines the use of intraoperative data, gathered from intraoperative image analysis, with intraoperative templating on a preoperative ipsilateral image. The process begins in some constructions by (1) acquiring preoperative ipsilateral and intraoperative images and (2) scaling and aligning these images by using identifiable features on the pelvis to serve as a stationary base, together with intraoperative data of the acetabular component. The system initially displays the preoperative and intraoperative images next to one another, with the system aligning and scaling the images relative to one another by using the identified stationary bases in each image. The absolute scale, that is, objective scaling according to a measurement system such as in millimeters, at least for the intraoperative image, is determined by visually identifying the prosthetic implant device itself while entering the known metric size for at least one dimension of the device. Both images are scaled in some constructions using their respective stationary bases and, in other constructions, each image is scaled independently, such as by using a ball marker for the preoperative image and the known dimension of the implant for the intraoperative image.

In preferred implementations of this Reverse Templating method, the user is guided to identify one or more landmark points (i.e. the tear drop anatomical feature of the pelvis) on each image and is then guided by the system to position templates that directly overlay the acetabular component and femoral stem implants visible in the intraoperative image. In other words, a first, acetabular template is superimposed over the acetabular component and a second, femoral template is superimposed over the femoral stem of the implant during certain preferred implementations of the present overlay technique. This template overlay in the intraoperative image does not calculate any offset or leg length data directly, but it provides other intraoperative data (i.e. abduction angle) that enables the system and user to precisely position the acetabular component and femoral stem templates on the preoperative image. The use of intraoperative data in the preoperative image, as gathered from overlaying templates in the intraoperative image, transforms this approach from an "estimation" technique to one that provides extremely precise calculations of intraoperative offset and leg length changes. The technique's use of templates additionally allows the surgeon to proactively analyse how intraoperative changes to implant selection will affect leg length and offset.

Figure 65:
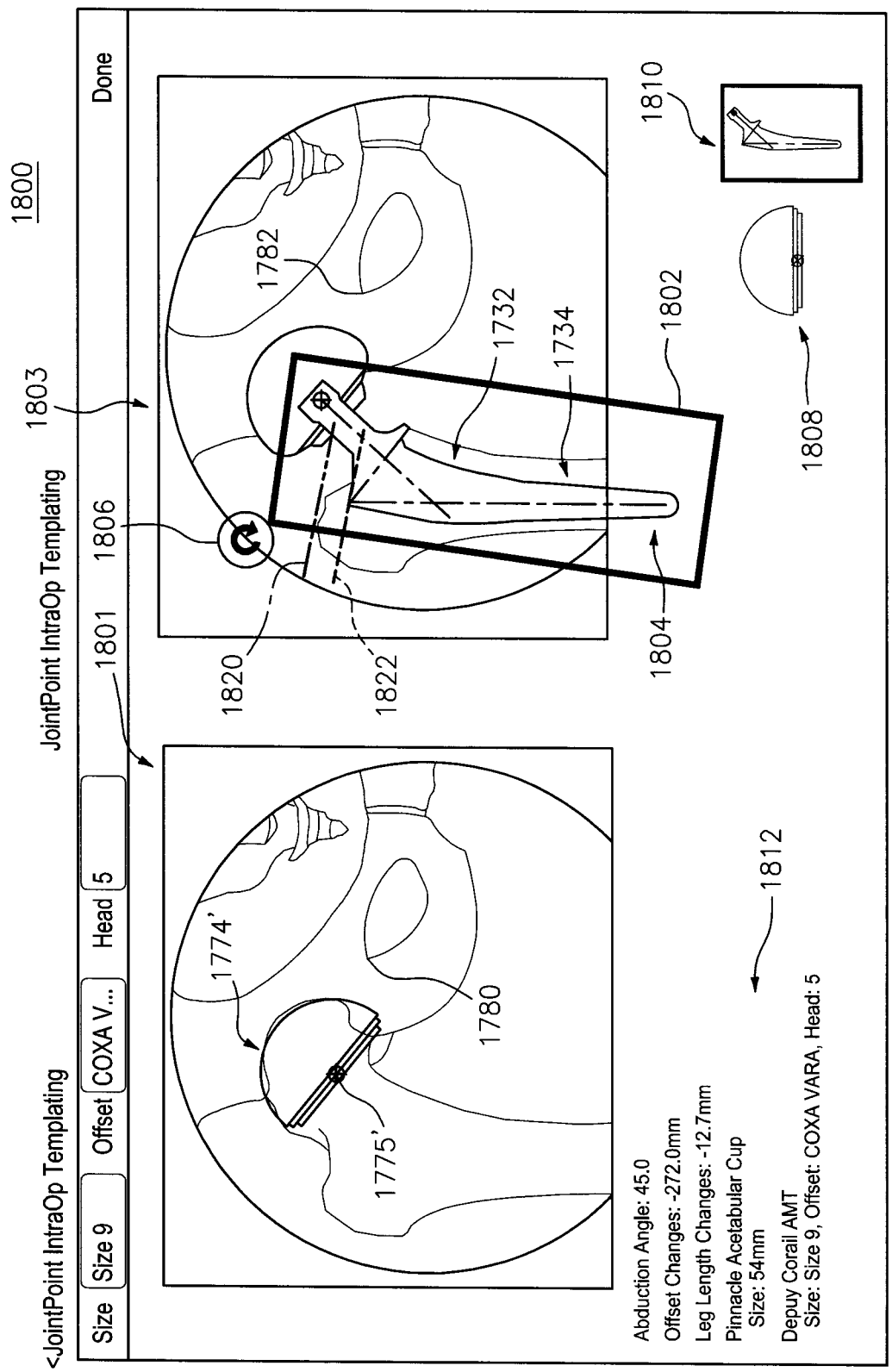
FIG. 65 is a schematic screen view similar to FIG. 64 showing the acetabular component outline overlaid on the femoral head on the left-hand, preoperative image with an overlay image of the prosthesis superimposed and aligned with the femoral stem of the prosthesis in the right-hand, intra-operative image.
Figure 66:
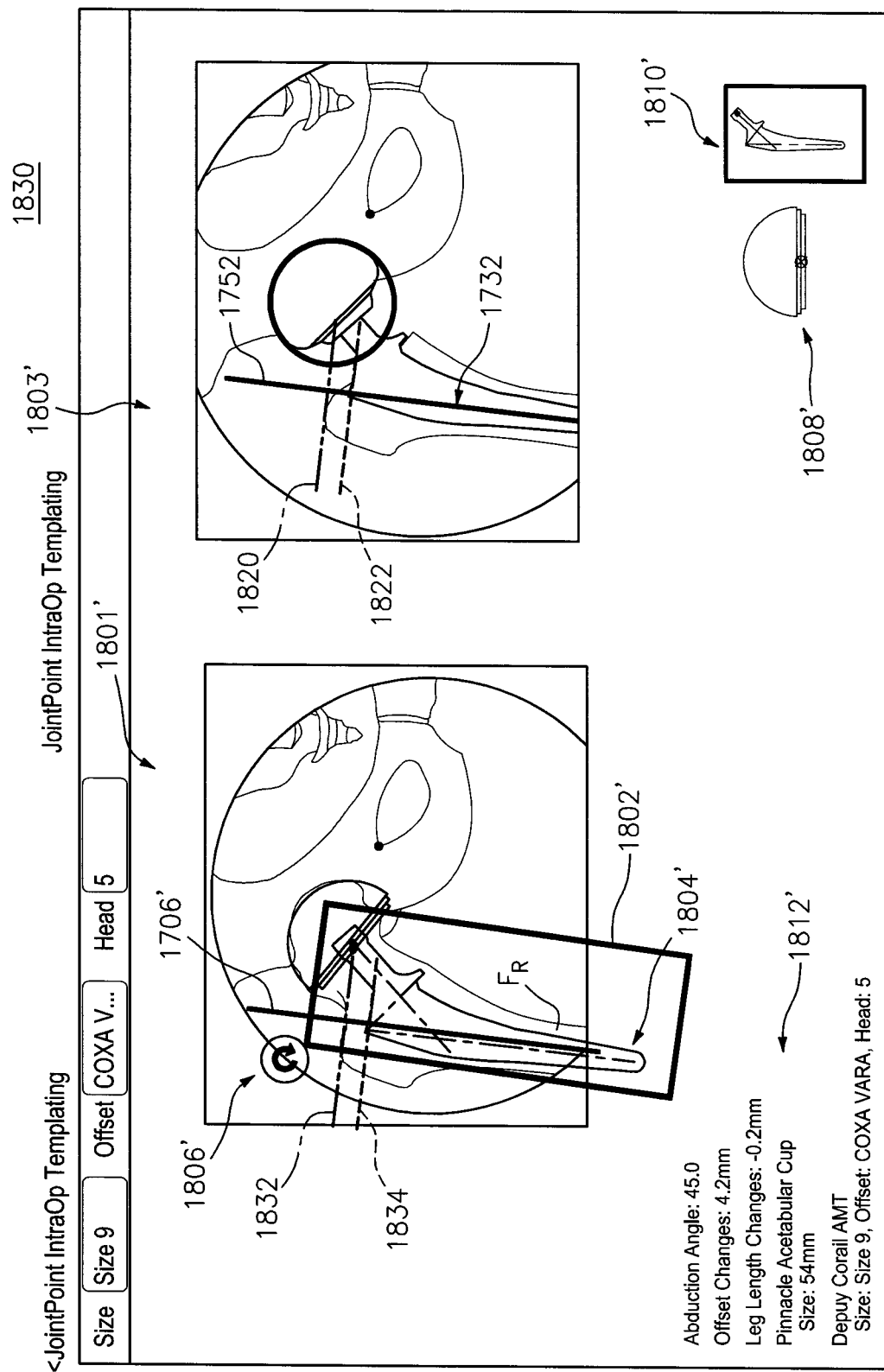
FIG. 66 is a schematic screen view similar to FIG. 65 showing the femoral stem template placed on the pre-operative image, utilizing intraoperative data gathered in the step represented by FIG. 65, with intraoperative Offset and Leg Length calculations.
Figure 67:
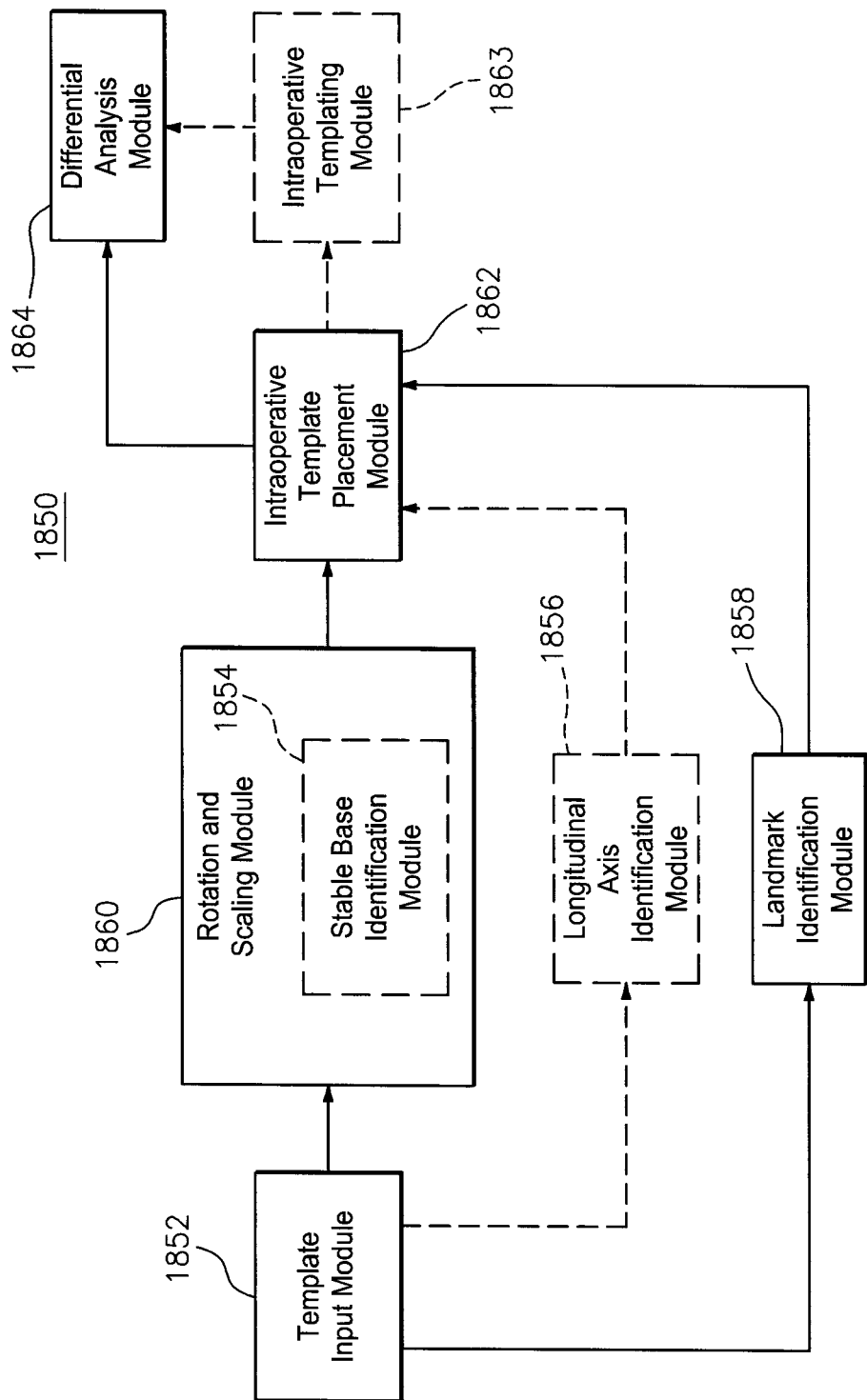
FIG. 67 is a schematic diagram of an Intra-operative Analysis Module according to the present invention to implement the Templating Technique generating images as shown above in FIGS. 60-66.

One system that implements this intraoperative Reverse Templating technique is shown in Intra-operative Analysis Module 1850 in FIG. 67. The method for one construction of the system is depicted in flowchart segments 1870 and 1872, FIGS. 68A and 68B, that comprise a Flowchart U depicting Intraoperative Templating Flow. The system and method that implements this Intraoperative Templating technique generates images such as shown in FIGS. 60-66.

In one construction, intra-operative Analysis Module 1850 according to the present invention, FIG. 67, includes Image Selection Module 1852 which communicates with a Rotation and Scaling Module 1860 that preferably includes an optional Stable Base Identification Module 1854, shown in phantom. In this construction, Template Input Module 1852 further communicates with an optional Longitudinal Axis Identification Module 1856, shown in phantom, that provides femoral axis identification in this construction which is particularly useful if the first and second images are not taken in virtually the same position, that is, along the same viewing angle, and a Landmark Identification Module 1858. All three of modules 1860, 1856 and 1858 provide inputs to Intraoperative Template Placement Module 1862; in this construction, Stable Base Identification Module 1854 generates a stable base, also referred to as a stationary base formed from two or more points selected on a patient's anatomy, as part of Rotation and Scaling Module 1860, whose results are then provided to Intraoperative Template Placement Module 1862. In one construction, Module 1862 facilitates placement of digital templates of acetabular and femoral components onto a preoperative image using intraoperative data including templating data from the intraoperative image. After templating, information is provided to the Differential Analysis Module 1864 for further calculations and analysis, including offset and leg length calculations in some constructions. One or more of the modules 1852-1864 can interface with a display or other interactive communication with a user. Another optional component is an Intraoperative Templating Module 1863, shown in phantom, which provides further processing of the output of Intraoperative Template Placement Module 1862, such as performing "what if" planning analysis or to modify one or more of the digital templates, before providing the results to Differential Analysis Module 1864.

Figures 68A, 69:
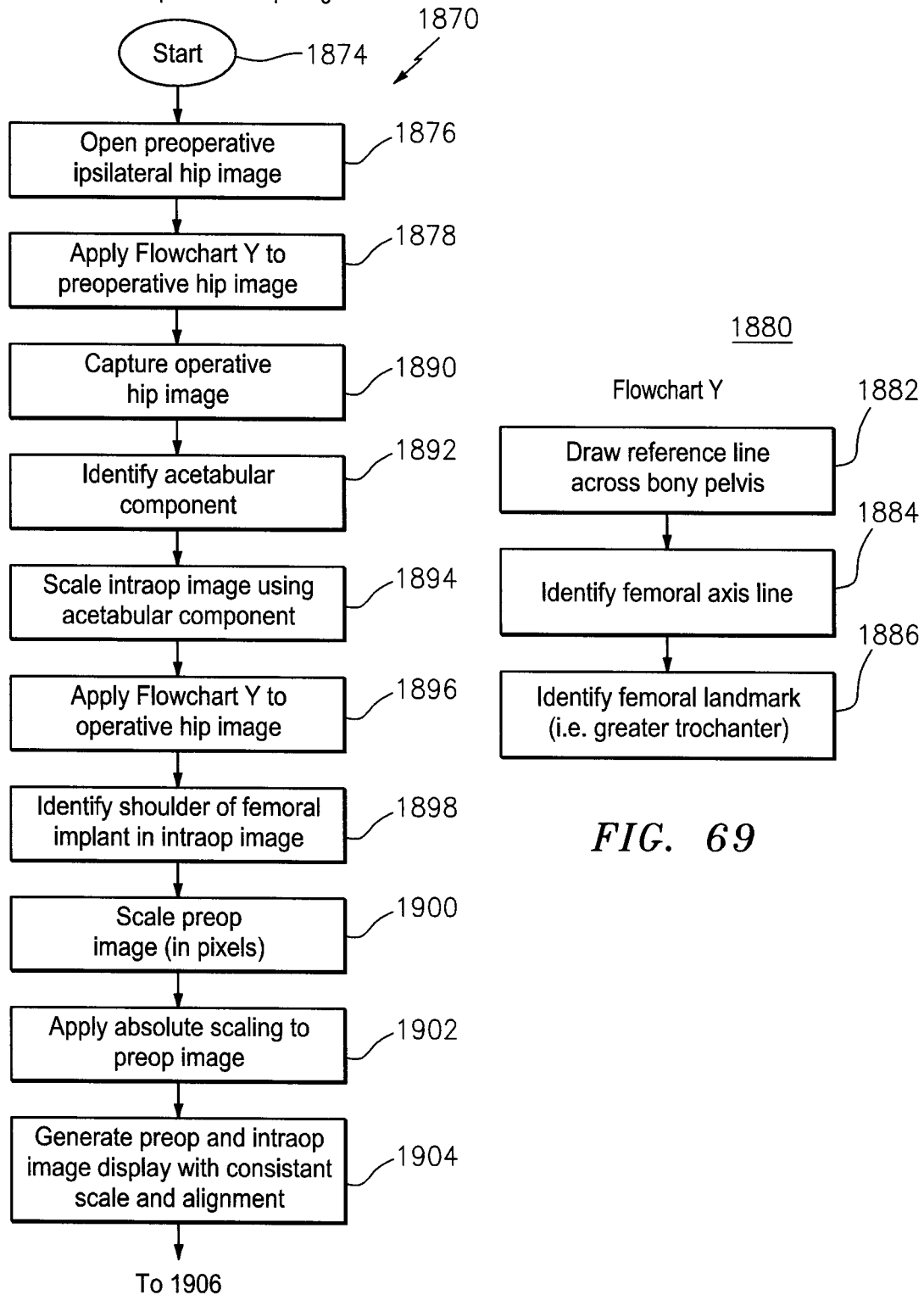
FIGS. 68A and 68B are a Flowchart U showing Intraoperative Templating Flow within the Module of FIG. 67.
FIG. 69 is a Flowchart Y showing functions applied to the pre-operative and intraoperative hip images for Intraoperative Templating of Flowchart U.

All references to "module" in relation to FIGS. 68A-69 refers to the modules of Intraoperative Analysis Module 1850, FIG. 67, with "ID" referring to "Identification". Further, the order in which the preoperative, reference image and the intraoperative, results image are marked or scaled among steps 1876 to 1902 can be interchanged in other implementations. In other alternative constructions, analysis is conducted utilizing a contra-lateral image instead of or in addition to an ipsa-lateral image as described below.

Figure 60:
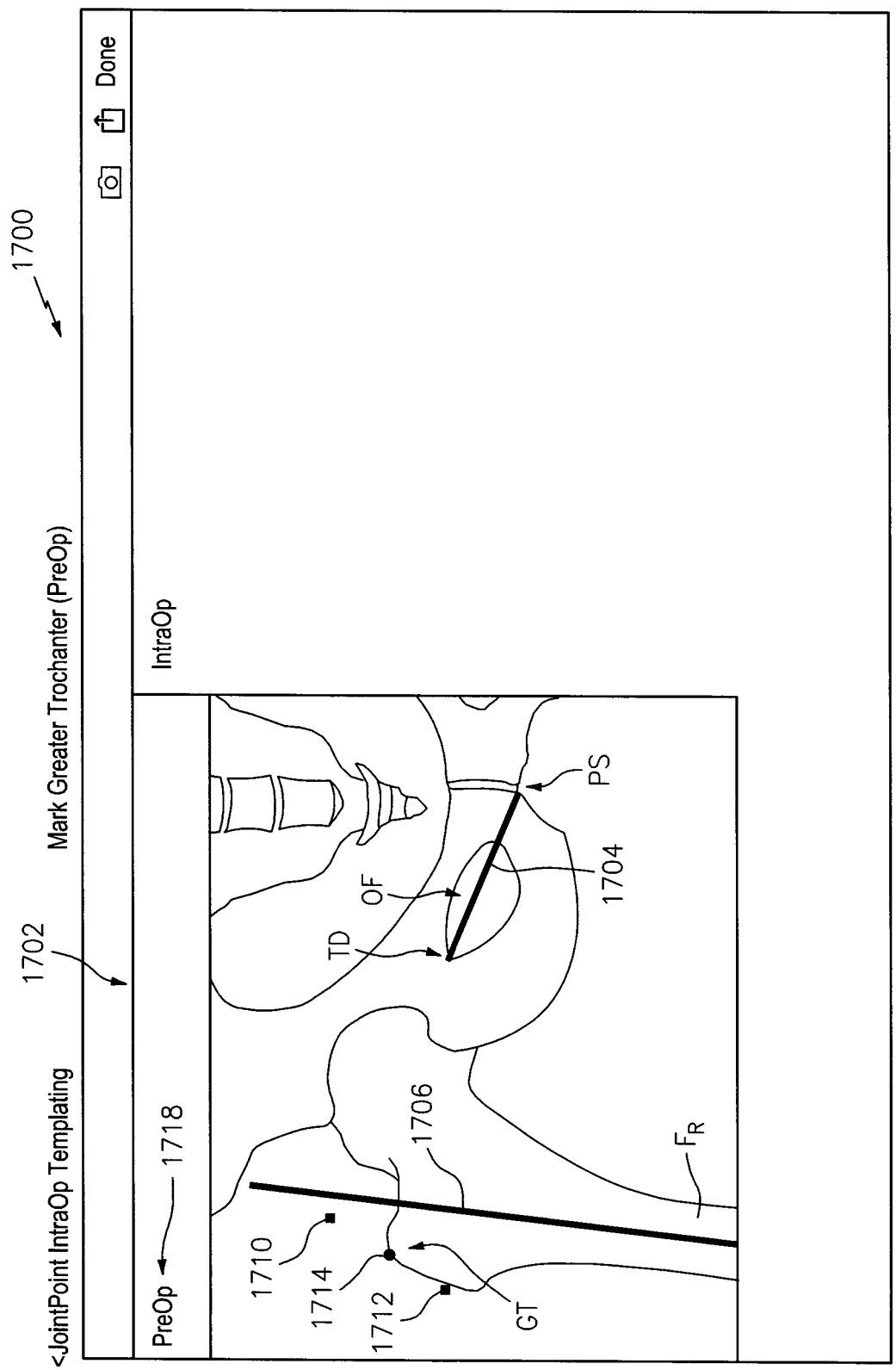
FIG. 60 is a schematic screen view of an image of the right side of a patient's hip prior to an operation and showing a mark placed on the greater trochanter as a landmark or reference point according to the present invention.

The method begins in one construction with initiation, step 1874, FIG. 68A, and a user-selected preoperative ipsilateral hip image is opened for display, step 1876, by Image Selection Module 1852. The system guides the user to indicate whether the image is a right or left hip. A screen view 1700, FIG. 60, depicts the selected image 1702 of the right side of a patient's hip prior to an operation, with pubic symphysis PS, obturator foramen OF and right femur F$_R$. The image 1702 can be acquired by directly interfacing with an imaging system or otherwise by taking a picture of a radiographic image using an iPhone camera or similar technology. A label 1718 of "PreOp" indicates that it is a pre-operative image.

The method continues with the preoperative hip image being processed, step 1878, by the technique of flowchart 1880, FIG. 69, which is a Flowchart Y showing functions applied to the pre-operative hip image for Intraoperative Templating of Flowchart U. The specific functions include identification of a 'stable base' (sometimes referred to as a 'stationary base') according to the present invention, identification of the femoral axis, and identification of the greater trochanter in this construction. At step 1882, FIG. 69, a reference line is drawn by the Stable Base ID Module 1854 across the bony pelvis, as illustrated by the "stable base" line 1704 in FIG. 60 which is shown extending from the teardrop TD to the lower portion of the pubic symphysis PS. A femoral axis line 1706, representing the longitudinal axis of the femur, is then identified in step 1884, FIG. 69, by the Longitudinal Axis ID Module 1856. A femoral landmark such as the greater trochanter is identified, step 1886, by Landmark ID Module 1858; in other constructions, one or more alternative femoral landmarks such as the lesser trochanter are identified. As guided by step 1886, guide squares 1710 and 1712, FIG. 60, assist the user in placing a marker 1714 on the greater trochanter GT as a landmark or reference point. In some constructions, the "stable base" line 1704, "femoral axis" line 1706, and marker 1714 on the greater trochanter (or other femoral landmark) may be automatically placed in appropriate locations by the system's image recognition capabilities and then may be modified by the user. In other constructions, the user is prompted to place these lines and markers without system intervention.

Figure 61:
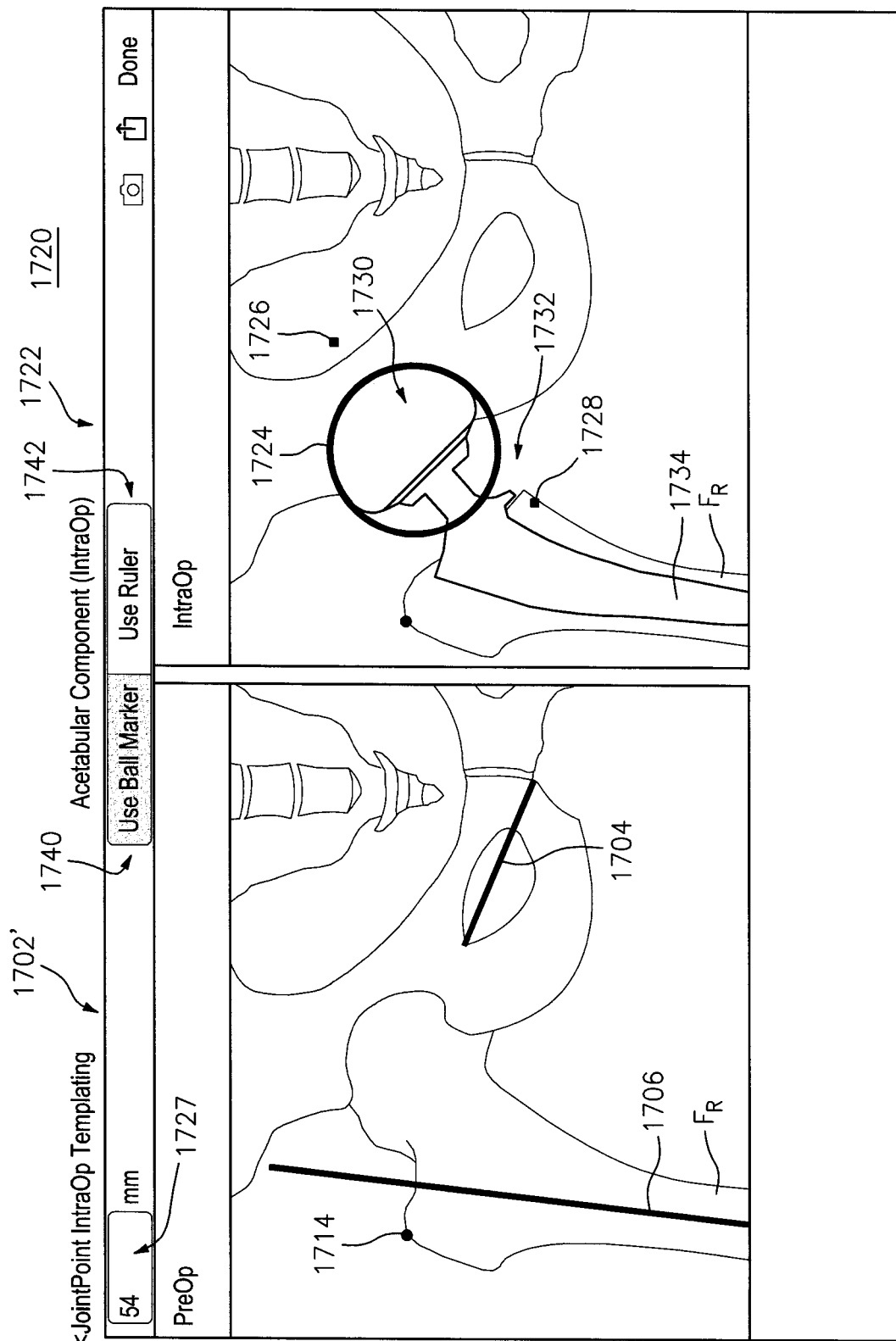
FIG. 61 represents a screen viewable by the user during a surgical procedure guided according to the present invention showing two images, the left-hand image representing a pre-operative view similar to FIG. 60 and the right-hand image representing an intra-operative view with a circle placed around the acetabular component of an implant to enable scaling or rescaling of that image based on an object of known size.

Continuing with step 1890, FIG. 68A, the technique captures the operative hip image, that is, an image is obtained of the patient's hip during surgery, utilizing the Image Selection Module 1852. The operative hip image may be captured through various methods, such as through a direct connection with a fluoroscopy machine, a DICOM file upload, or by the user taking a camera picture of the radiographic image using an iPad or other mobile computing device. After capturing the operative hip image, the acetabular component is identified in step 1892 by the Rotation and Scaling Module 1860, such as shown in FIG. 61. The intraoperative image is scaled, step 1894, by entering the size of the acetabular component into the system, which is processed by Rotation and Scaling Module 1860.

FIG. 61 represents a screen 1720 viewable by the user during a surgical procedure guided according to the present invention showing two images in split screen view, the left-hand image 1702' representing a pre-operative view similar to FIG. 60, and the right-hand image 1722 representing an intra-operative view with a circle 1724 placed around the acetabular component 1730 of an implant 1732 to enable rescaling of that image. In some constructions, the system attempts to automatically place the circle 1724 around the acetabular component 1730 using image recognition algorithms. In other constructions, the user is prompted to place the circle around the acetabular component without system guidance. The user may use guide squares 1726 and 1728, if required, to alter the size and position of circle 1724 so that it precisely encircles the acetabular component 1730. In one construction, the user enters the diameter of circle 1724, such as "54 mm", using data entry box 1727. This enables the system to generate absolute scaling in the intraoperative image by taking the diameter in pixels of the acetabular component and combining that with the known diameter in millimeters. Other prompts to guide the user include the choice of soft-key 1740 for "Use Ball Marker" and soft-key 1742 for "Use Ruler", to allow the user to accomplish intraoperative scaling using other anatomical features or observable devices if desired.

Figure 62:
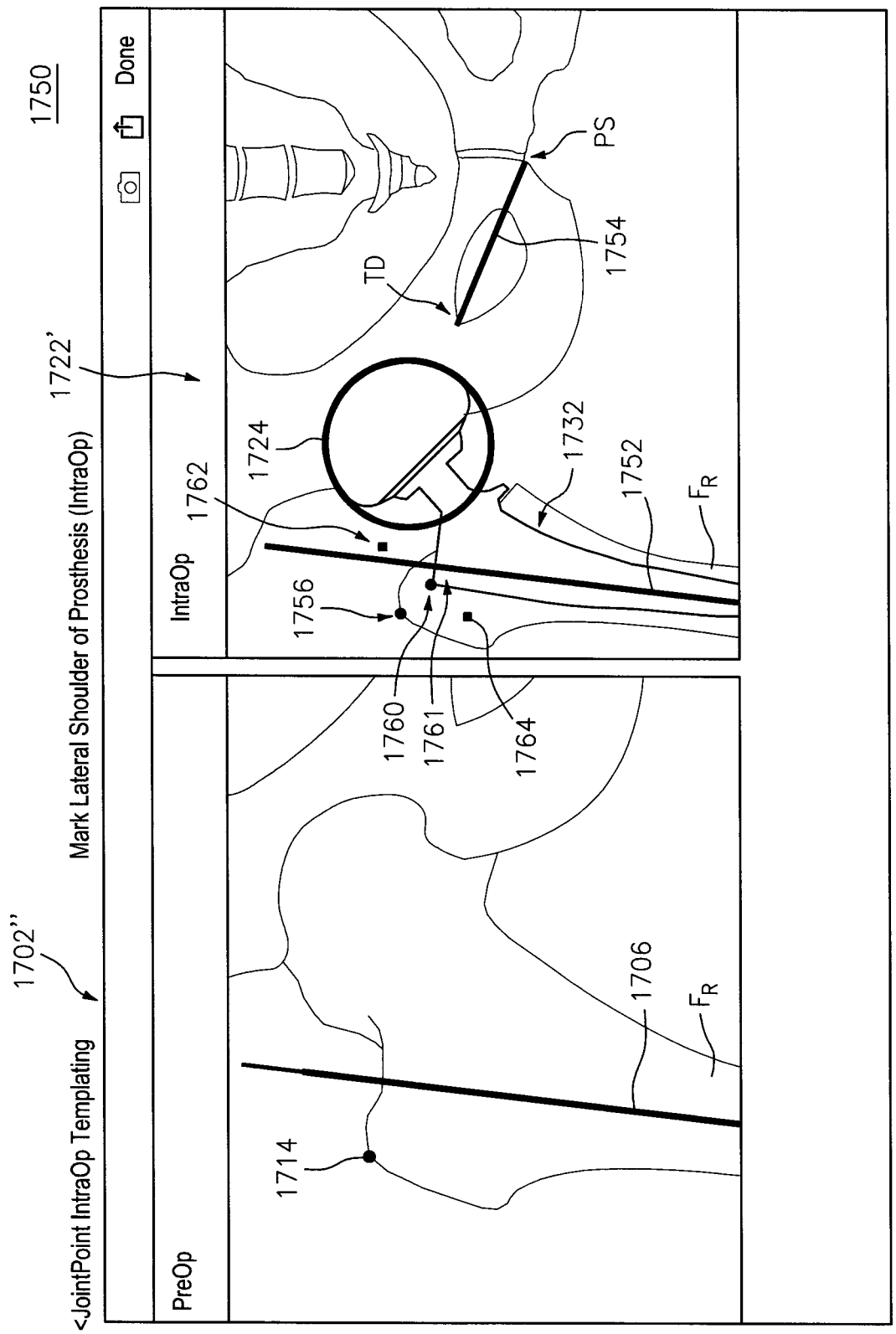
FIG. 62 is a schematic screen view similar to FIG. 61 indicating marking of the lateral shoulder of the prosthesis of the right-hand, intra-operative image, also with the greater trochanter marked in both images as a femoral landmark.

The method continues with step 1896, FIG. 68A, by applying Flowchart Y, FIG. 69, to the operative hip, including steps 1882-1886 as described above, in order to identify the "stable base", "femoral axis" and greater trochanter in the operative hip image, as illustrated in FIG. 62. The shoulder of the femoral implant is identified, step 1898, in the intraop image by Landmark ID Module 1858, which is also illustrated in FIG. 62.

FIG. 62 is a schematic screen view 1750 similar to FIG. 61 with pre-operative image 1702" and indicating placement of a mark 1760 of the lateral shoulder 1761 of the prosthesis 1732 of the right-hand, intra-operative image 1722', as guided by guide squares 1762 and 1764. Also shown is the greater trochanter having mark 1756 as a femoral landmark and a stable base line 1754 connecting the tear drop TD to the lower portion of the pubic symphysis PS. Alternative constructions may use a stable base line 1754 that connects a different set of 2 or more anatomical landmarks across the pelvis, but the landmarks must be placed on consistent points across the preoperative and intraoperative images. Similarly, alternative constructions may replace the greater trochanter with a different femoral landmark (i.e. lesser trochanter) that can be identified in both preoperative and intraoperative images. In some constructions, the system will attempt to auto-generate placement of the mark 1760 at the lateral should 1761 of the prosthesis, the mark 1756 on the greater trochanter, and stable base 1754 across pelvic landmarks, and then allow the user to modify placement. Other constructions will prompt the user to determine placement of this data without automated guidance.

The identification of consistent stationary bases in the preoperative image and intraoperative images can be combined with the absolute scaling data in the intraoperative image to apply absolute scaling to the preoperative image. To accomplish this, the method continues in step 1900, FIG. 68A, by scaling the preoperative image in pixels by Rotation and Scaling Module 1860, which scales the lines across the bony pelvis in both the preoperative and intraoperative images so that they are of identical size in pixels, such as by using stable base line 1704, FIG. 61, and stable base line 1754, FIG. 62.

Continuing with step 1902, FIG. 68A, absolute scaling is applied to the preoperative image by using the known size of the acetabular component in the intraoperative image. Because both images are scaled according to an identical stationary base, the absolute scale ratio in the intraoperative image, determined by acetabular component diameter, can be applied to the preoperative image. This unique technique provides precise scaling to the preoperative image by using objects of known size in the intraoperative image and applying this scaling to the preoperative image. The result is that a significantly more precise absolute scaling can be determined in the preoperative image, as compared to traditional preoperative image scaling techniques that utilize ball markers or similar techniques.

Alternative constructions may alternatively apply absolute scaling to the preoperative and intraoperative images directly in each image, and without the need for a stationary base. For example, each image may be scaled by a ball marker or other scaling device, known magnification ratios of a radiographic device, or direct measurements of anatomical points (such as a direct measurement, via callipers, of the extracted femoral head, which can be used to scale the preoperative image).

Alternative constructions may also replace the 'stationary base' with various other techniques that could be used to scale and align the preoperative and intraoperative images relative to one another. One example of such a construction would involve overlaying two images and displaying them with some transparency so that they could both be viewed on top of one another. The user would then be prompted to rotate and change their sizing, so that the pelvic anatomy in the two images were overlaid as closely as possible.

A "side by side" display is generated by the Rotation and Scaling Module 1860, step 1904, which is consistently rotated and scaled based on the stable base line across the bony pelvis. In some constructions, a single image that combines preoperative and intraoperative picture renderings side by side will be displayed. Other constructions will maintain the preoperative and intraoperative images as separate images. All constructions will rotate and scale the images relative to one another using the stationary bases across the pelvis.

Figure 63:
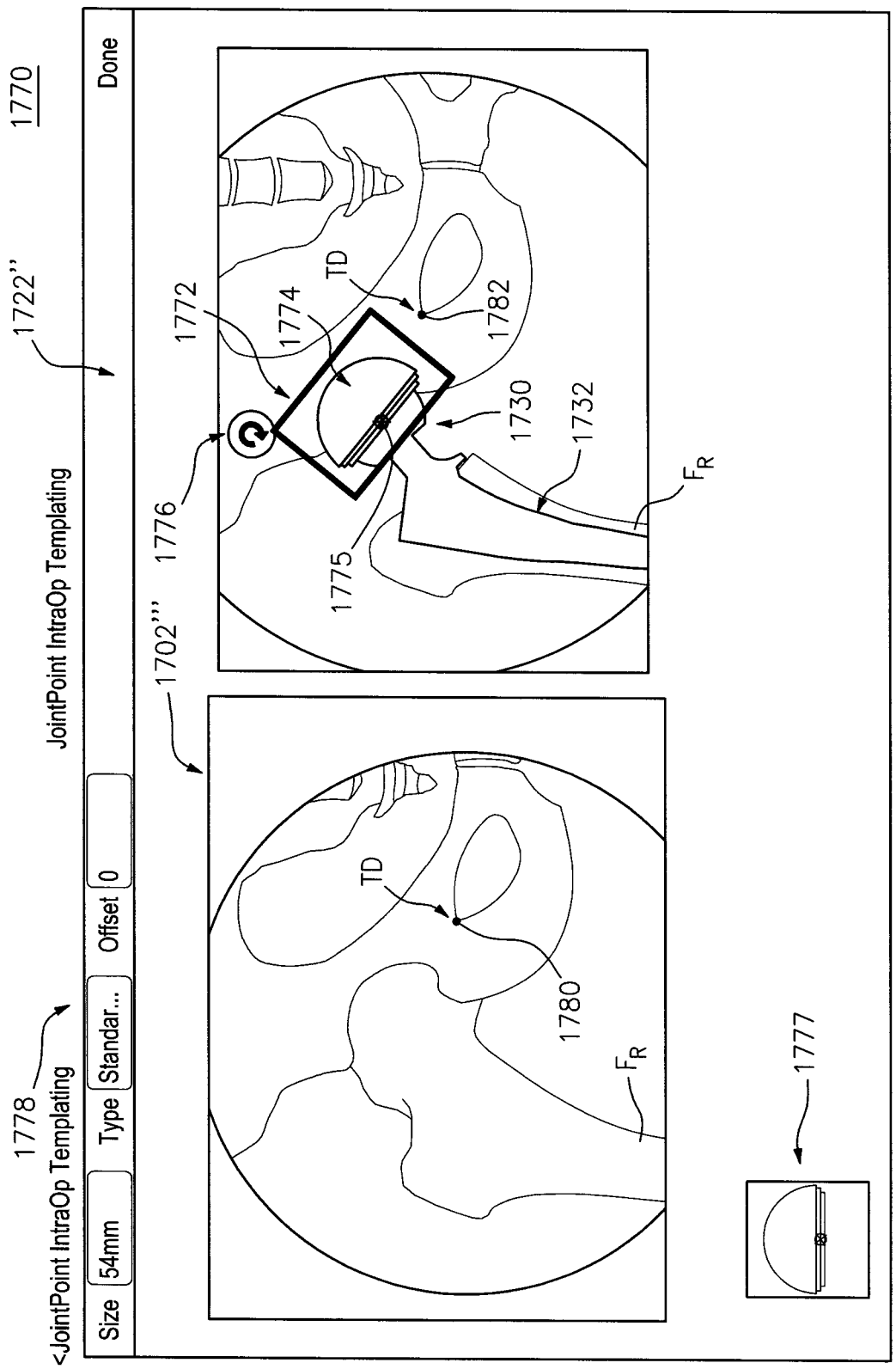
FIG. 63 is a schematic screen view similar to FIG. 62 with a reference box indicating an acetabular template generated on top of the acetabular component of the prosthesis on the intra-operative femur in the right-hand view.
Figure 68B:
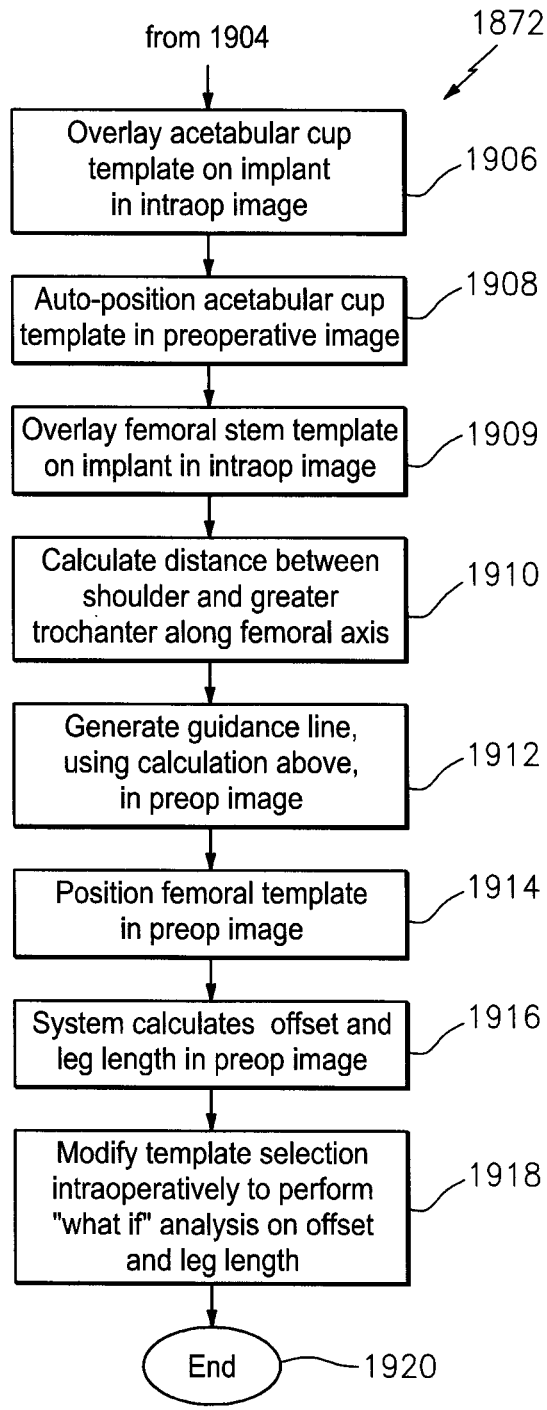

After aligning the preoperative and intraoperative images, the method continues with step 1906, FIG. 68B, with the user or system drawing an acetabular cup template directly on top of the implant in the intraoperative image, such as shown in FIG. 63. The acetabular cup template is placed to match the actual abduction angle by Intraoperative Templating Module 1862. FIG. 63 is a schematic screen view 1770 similar to FIG. 62 with a reference rectangle 1772, also referred to as a "box" or "frame", indicating an acetabular component template 1774, with a central point 1775, placed directly above the acetabular component of the prosthesis on the intra-operative femur in the right-hand view. In some constructions, the system combines known anatomical data (i.e. the circle 1724 placed around the acetabular component in FIG. 61) and image recognition to generate the initial placement of the acetabular component template on the intraoperative image. In an alternative construction, the acetabular component template is placed at a default abduction angle and modified by the user. In either construction, the user can modify the template abduction angle to match the actual acetabular component abduction angle by using movement control icon 1776, also referred to as a "rotation handle", similar to the icon 527 shown in FIG. 21 above. This assists "touch" or "click and drag" control used to facilitate repositioning and adjustment of the template 1774 relative to the image of the acetabular component 1730 of implant 1732. In one construction, icon 1777 is clicked or touched to "activate" rectangle 1772, template 1774 and/or movement control icon 1776 to enable movement thereof by the user. Additional information is provided to the user by fields 1778 such as "Size 54 mm", "Type Standard", and "Offset 0" as illustrated. Markers 1780 and 1782 have been placed in images 1702''' and 1722", respectively, to designate the location of tear drop TD in each image. In some constructions, the system may automatically generate markers 1780 and 1782 because the teardrop TD has already been identified, for example in a situation when the teardrop is used to create a stationary base and can be readily identified.

In step 1908, FIG. 68B, the system positions the acetabular cup template in identical position, relative to the pelvis, in the preoperative image as compared to the placement on the intraoperative image described above. This is illustrated in FIG. 64 using known teardrop locations in the pre- and intra-operative images.

Figure 64:
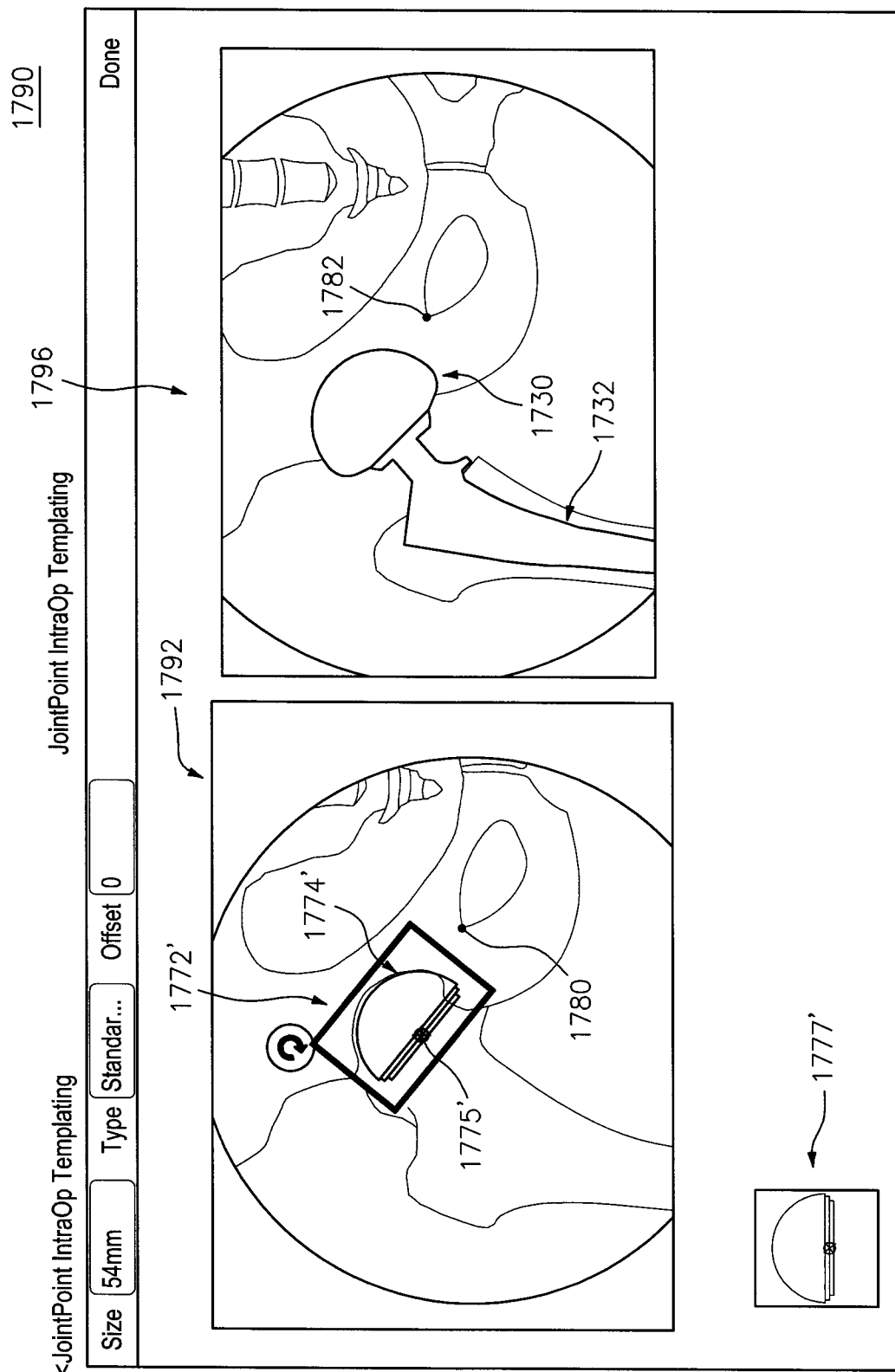
FIG. 64 is a schematic screen view similar to FIG. 63 with the acetabular template now rendered in a precise location across the femoral head in the preoperative view, using intraoperative data gathered during the step represented by FIG. 63.

FIG. 64 is a schematic screen view 1790 similar to FIG. 63 but with the acetabular template 1774', with a central point 1775', now re-positioned on top of the femoral head in the preoperative view 1792. The acetabular template positioning in the preoperative image, as shown in this figure, is auto-generated by the system using intraoperative image data gathered from the placement of the acetabular template in the intraoperative image. Specifically, the system calculates the x and y distances from the teardrop to the acetabular prosthesis in the intraoperative image display, and auto-generates the acetabular template position in the preoperative image by maintaining the distance from the teardrop to the acetabular template in the preoperative image. The system also maintains the abduction angle obtained by maintaining the acetabular template abduction angle that was analysed in the intraoperative image. This process ensures that the acetabular template is placed in the preoperative image in a position, relative to the pelvis, that precisely matches the acetabular component position in the intraoperative image. The method effectively transforms the templating exercise from one of preoperative estimation and planning to one of precision-guided intraoperative analysis. The acetabular component placement is facilitated by the scaling and alignment of the preoperative and intraoperative images described above.

In alternative constructions, a physical device, sensors, caliper measurement of directly observable anatomical landmarks, or some other form of mechanical and electrical hardware may be used to create image scaling as a substitute for scaling based on the acetabular component. One example of an alternative construction (although not as precise) would be to measure the extracted femoral head using calipers, and then to scale the image by marking the femoral head in the preoperative image. In this method, absolute scaling is initially created in the preoperative image, and then propagated to the intraoperative image by scaling and aligning consistent stationary bases.

The process continues with step 1909, FIG. 68B, by Intraoperative Templating Module 1862, with the system or user positioning a femoral stem template directly on top of the femoral stem in the intraoperative image. As with the acetabular component template process described above, this step is used to determine intraoperative data that will be used later in the method. FIG. 65 is a schematic screen view 1800 similar to FIG. 64, demonstrating positioning of the femoral stem template in the intraoperative image. The figure shows the acetabular component outline 1774' overlaid on the femoral head on the left-hand, preoperative image 1801. The user selects the femoral stem template used in surgery, identified for this implant 1732 as "Depuy Corail AMT Size: Size 9, Offset: COXA VARA, Head: 5", and the system renders the template for this model on the screen. The user or system overlays the template image 1804, within rectangle 1802, of the prosthesis 1732, directly on top of the observed femoral component in the intra-operative image 1803. Initial calculations of Offset Changes and Leg Length Changes are not yet relevant, but are displayed in one corner of screen 1800 by indicia 1812 including "Offset Changes: −272.0 mm", and "Leg Length Changes: −12.7 mm", along with "Abduction Angle: 45.0". Control icon 1808 for the acetabular cup and an icon 1810 for the femoral stem template 1802 and 1804 are provided in another portion of screen view 1800.

Note dashed 1820 extending from the neck of the implant 1732 over the greater trochanter, and a parallel dashed line 1822 which touches the shoulder of implant 1732. (The user identified the shoulder of the femoral prosthesis 1732, also referred to as the superolateral border of the femoral prosthesis, in the intraoperative image illustrated in FIG. 62 above.) The system draws both lines 1820 and 1822 perpendicular to the femoral axis and is guided by user positioning of markers that identify the greater trochanter and shoulder implant.

In step 1910, FIG. 68B, the system identifies the distance between the shoulder of the implant and the greater trochanter along the femoral axis line, as shown in FIG. 65. In one construction, this process is supported by dashed reference lines 1820 and 1822 which are generated to be perpendicular to femoral axis line 1752, identified earlier in the process and displayed in FIG. 66. The calculated distance between lines 1820 and 1822, along the femoral stem axis, is intraoperative data that will be applied to the placement of the femoral stem template in the preoperative image.

In step 1912, the system takes the calculated distance described above and generates a line in the preoperative image that is perpendicular to the femoral axis line and is the same distance away from the greater trochanter, as shown in FIG. 66. For step 1914, the system places the femoral stem template in the preoperative image, using the line generated in step 1912.

FIG. 66 is a schematic screen view 1830 similar to FIG. 65 showing the femoral stem template 1804', within a rectangle 1802', placed on the pre-operative image 1801' superimposed and aligned with the femur $F_R$. The system automatically repositions the femoral stem template 1804' in preoperative image 1801' by using intraoperative data gathered from the placement of the same template in the intraoperative image. Specifically, the system draws guidance lines and determines the implant position on the femur in the preoperative image through the following steps:

- The system draws dashed line 1832 through the greater trochanter point (as previously identified by a marker) and perpendicular to the femoral axis in the preoperative image (which may be different than the intraoperative femoral axis).
- The system takes the calculated distance, along the femoral axis, between the greater trochanter and the shoulder of the implant from the intraoperative image. The system generates dashed line 1834 in the preoperative image below the greater trochanter line 1832, and perpendicular to the femoral axis, based on the distance calculated in the intraoperative image.
- Line 1834 is generated as a visual guide for the user or system to position the femoral stem template by placing the shoulder of the femoral stem template on this line.
- The system calculates the difference between the greater trochanter and the shoulder of the prosthesis in the intraoperative image along the femoral axis and perpendicular to the femoral axis. The system then generates the location of the femoral stem template in the preoperative image by replicating the distance relative to the greater trochanter and placing the shoulder of the prosthetic at that location.
- Additionally, the femoral stem is automatically rotated so that it maintains consistent angle relative to the femoral axis in both images. For example, if the femoral axis is 15 degrees in the intraoperative image and 10 degrees in the preoperative image, the system will automatically rotate the femoral stem template by 5 degrees when it moves it to the preoperative image. Finally, the femoral stem template may be adjusted, either by the user or automatically by the system, to match the location of the femoral canal (i.e. movement of the femoral stem template perpendicular to the femoral axis).
- Having combined intraoperative data with preoperative imaging, the system now precisely calculates, in step 1916 and Differential Analysis Module 1864, the offset and leg length differences based on the positioning of the femoral stem and acetabular cup templates in the preoperative image.
- Finally, the user can now modify, in step 1918, implant template selections in the system to perform "what if analysis" and to proactively analyze how intraoperative implant changes will affect offset and leg length calculations, allowing intraoperative changes and decision making to be based on calculations made even before inserting a different implant during surgery. The system or user will then place the new implant selection using dashed line 1834 and other guidelines, and will automatically calculate anticipated offset and leg length changes by combining the template technique with the intraoperative data being used.

The Offset and Leg Length change calculations are displayed in one corner of screen 1830 by indicia 1812' including "Abduction Angle: 45.0", "Offset Changes: 4.2 mm", and "Leg Length Changes: −0.2 mm". Also identified is "Pinnacle Acetabular Cup Size: 54 mm" and "Depuy Corail AMT Size: Size 9, Offset: COXA VARA, Head: 5" for implant 1732 in this example. Control icon 1808' for the acetabular cup and an icon 1810' for the femoral stem template 1802' and 1804' are provided in another portion of screen view 1830. In one construction, dashed reference lines 1832 and 1834 are generated to be perpendicular to femoral axis line 1706'.

In some constructions, the system will begin with the JointPoint Anterior process and finish with the Reverse Templating system. Most of the data required to do Reverse Templating can be carried over from JointPoint Anterior by the system so that very few steps are required by the system to process the Reverse Templating technique.

FIG. 70 is an overlay image 2000 of a preoperative hip image 2001 and an intraoperative hip image 2003 having a trial implant 2002 in a hip with the acetabular component 2004 transacted by stationary base lines 2006 and 2007 extending between a first point 2008 on the obturator foramen OF and a second point 2010 on the anterior inferior iliac spine AIIS of the ileum. Also shown are two error analysis triangles 2020 (solid lines) and 2030 (dashed lines). Circles 2022 and 2032 in this construction represent a landmark point on the greater trochanter in images 2001 and 2003, respectively. Image 2000 is a representation of preoperative and intraoperative hip images 2001 and 2003 overlaid according to stationary base lines 2006 and 2007, respectively. Three identical pelvic points 2024, 2026, 2028 and 2034, 2036, 2038 in images 2001 and 2003, respectively, have been identified, with the system 200, FIGS. 4C-4F, generating triangles 2020 and 2030 for each image as represented by FIG. 70. The triangles 2020 and 2030 can be visually compared to analyze the error in the anatomic area containing the stationary bases which, in this case, is the pelvis. A numerical confidence score or other normalized numeric error analysis value may also be calculated and displayed in the system by calculating the distance between points, comparing them to the length of the triangle vectors, and then normalizing the data, possibly using a log or other such nonlinear algorithm. The visual display and/or numerical confidence score provides efficacy analysis in the construction. In other words, error analysis and correction is provided in some constructions for at least one image, such as providing a confidence score or other normalized numeric error analysis, and/or a visual representation of at least one error value or error factor, such as relative alignment of one or more geometric shapes, e.g. triangles, or symbols in two or more images.

In some constructions of the various alternative systems and techniques according to the present invention, visual and/or audible user instructions are sequentially generated by the system to guide the user such as "Draw line along Pubic Symphysis". Guidance for surgery utilizing other types of implants, and for other surgical procedures, including partial or total knee or shoulder replacements and foot surgery as well as wrist surgery, will occur to those skilled in the art after reading this disclosure. Also, other types of medical imaging using energy other than visible light, such as ultrasound, may be utilized according to the present invention instead of actual X-rays. Moreover, if a computer interface tool, such as a stylus or light pen, is provided to the user in a sterile condition, than the user can remain within a sterile field of surgery while operating a computing device programmed according to the present invention.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated.

It is also to be understood that the drawings are not necessarily drawn to scale, but that they are merely conceptual in nature. Other embodiments will occur to those skilled in the art and are within the scope of the present disclosure.

What is claimed is:

1. A system comprising one or more computers to analyze images at a surgical site within a patient, the one or more computers performing the following steps:
   acquiring a preoperative image of the surgical site;
   acquiring an interoperative image of the surgical site, wherein the intraoperative image depicts at least a portion of a first implanted device at a first implanted location and a first implanted orientation;
   selecting a first digital template image of the first implanted device, wherein the first digital template image comprises a digital representation of the first implanted device;
   superimposing the first digital template image over the intraoperative image so that the first digital template image directly overlays the first implanted device shown in the intraoperative image;
   determining a first anatomical landmark point in the intraoperative image and a corresponding first anatomical landmark point in the preoperative image; and
   superimposing the first digital template image over the preoperative image and orienting the superimposed first digital template image with respect to the first anatomical landmark so that a location of the first digital template image and an orientation of the first digital template image in the preoperative image correspond to the first implanted location and the first implanted orientation, respectively, of the first implanted device depicted in the intraoperative image.

2. The system of claim 1, further comprising the step of analyzing an effect of the first implanted device on at least one parameter of at least one bone of the patient.

3. The system of claim 1, further comprising the step of determining a first stationary base point on a first anatomical feature that is present in the preoperative image and a corresponding first stationary base point on the first anatomical feature in the intraoperative image.

4. The system of claim 3, further comprising the step of determining a second stationary base point on a second anatomical feature that is present in the preoperative image and a corresponding second stationary base point on the second anatomical feature in the intraoperative image.

5. The system of claim 4, further comprising the steps of scaling and rotating the preoperative image and the intraoperative image so that when the preoperative image and the intraoperative image are overlaid, (a) the first stationary base point and the corresponding first stationary base point are aligned, and (b) the second stationary base point and the corresponding second stationary base point are aligned.

6. The system of claim 1, further comprising the step of determining a first line extending across two or more anatomical features present in the preoperative image and a corresponding first line extending across two or more corresponding anatomical features in the intraoperative image.

7. The system of claim 1, further comprising the steps of:
selecting a second digital template image of a second implanted device depicted in the intraoperative image at a second implanted location and a second implanted orientation;
superimposing the second digital template image on the intraoperative image, such that the second digital template image directly overlays the second implanted device shown at the second implanted location in the intraoperative image;
determining a second anatomical landmark point in the intraoperative image and a corresponding second anatomical landmark point in the preoperative image; [[and]]
superimposing the second digital template image over the preoperative image and orienting the superimposed second digital template image with respect to the second anatomical landmark point, such that the location and orientation of the second digital template image in the preoperative image correspond to the second implanted location and the second implanted orientation, respectively, of the second implanted device depicted in the intraoperative image; and
analyzing an effect of the second implanted device on the at least one parameter of the at least one bone of the patient.

8. The system of claim 7, further comprising the step of substituting, for the superimposed second digital template image, a digital template of a comparable implantable device to estimate changes to the effect of the at least one parameter of the at least one bone of the patient when the comparable implantable device is used in place of the second implanted device.

9. The system of claim 1, further comprising the step of substituting, for the first digital template image of the first implanted device superimposed on the preoperative image, a digital template of a comparable implantable device to estimate changes to an effect of at least one parameter of the at least one bone of the patient when the comparable implantable device is used in place of the first implanted device.

* * * * *

UNITED STATES PATENT AND TRADEMARK OFFICE
CERTIFICATE OF CORRECTION

PATENT NO. : 10,758,198 B2
APPLICATION NO. : 14/630300
DATED : September 1, 2020
INVENTOR(S) : Noah D. Wollowick et al.

Page 1 of 1

It is certified that error appears in the above-identified patent and that said Letters Patent is hereby corrected as shown below:

In the Claims

In Column 40, Line 29, in Claim 1, delete "interoperative" and replace by inserting --intraoperative--.

In Column 41, Line 24, in Claim 7, delete "[[and]]".

Signed and Sealed this
Twenty-second Day of December, 2020

Andrei Iancu
*Director of the United States Patent and Trademark Office*